United States Patent [19]

Smyth

[11] Patent Number: 5,583,795
[45] Date of Patent: Dec. 10, 1996

[54] APPARATUS FOR MEASURING EYE GAZE AND FIXATION DURATION, AND METHOD THEREFOR

[75] Inventor: Christopher C. Smyth, Fallston, Md.

[73] Assignee: The United States of America as represented by the Secretary of the Army, Washington, D.C.

[21] Appl. No.: 407,142

[22] Filed: Mar. 17, 1995

[51] Int. Cl.$^6$ ................................................. A61B 03/14
[52] U.S. Cl. ........................... 364/516.444; 364/571.414; 364/559.444
[58] Field of Search .................................. 351/209, 211, 351/212, 246; 340/825.19; 348/15; 345/7; 356/139.03; 364/516, 571.01, 559

[56] References Cited

U.S. PATENT DOCUMENTS

| | | | |
|---|---|---|---|
| 3,986,030 | 10/1976 | Teltscher | 250/349 |
| 4,034,401 | 7/1977 | Mann | 358/93 |
| 4,109,145 | 8/1978 | Graf | 250/221 |
| 4,209,255 | 6/1980 | Heynau et al. | 356/141.3 |
| 4,623,230 | 11/1986 | Weinblatt | 354/318 |
| 4,648,052 | 3/1987 | Friedman et al. | 364/550 |
| 4,761,071 | 8/1988 | Baron | 351/212 |
| 4,852,988 | 8/1989 | Velaz et al. | 351/210 |
| 4,973,149 | 11/1990 | Hutchinson | 351/210 |
| 5,035,500 | 7/1991 | Rorabaugh et al. | 351/226 |
| 5,170,153 | 12/1992 | Migozzi et al. | 345/8 |
| 5,220,361 | 6/1993 | Lehmer et al. | 351/226 |
| 5,231,674 | 7/1993 | Cleveland et al. | 382/6 |
| 5,345,281 | 9/1994 | Taboada et al. | 351/210 |
| 5,386,258 | 1/1995 | Nagano | 354/400 |
| 5,410,376 | 4/1995 | Cornsweet et al. | 351/210 |

OTHER PUBLICATIONS

Adams, Charlotte (Mar. 1990). "If Looks Could Kill: The Eyes Have It", Military & Aerospace Electronics, pp. 35–37.
Monty et al, "Eye Movements and Psychological Processes", Hillsdale, pp. 185–199.
Calhoun et al, "Proceedings of the Human Factors Society 30th Annual Meeting," (1986).
Goode, "Eye Directed View", 21st Space Conference, Kennedy Space Center (1984).
Jacob, "What you see is what you get: the use of eye movements in human–computer interaction techniques", (1989) Naval Research Laboratory.
Smyth et al, "Comparison of oculometer and head–fixed reticle with voice or switch and touch panel for data entry on a generic tactical air combat display (Technical Memorandum 21–89)," (1989), Aberdeen Proving Ground, U.S. Armu Human Engineering Laboratory.

Primary Examiner—Emanuel T. Voeltz
Assistant Examiner—Craig Steven Miller
Attorney, Agent, or Firm—Freda L. Krosnick; Frank J. Dynda

[57] ABSTRACT

The invention is an apparatus for measuring eye gaze and fixation duration employing an electronic video display array as sequential sources of eye illumination. The video display of the apparatus may be task related or near infrared light sources used merely to track the user's eye. The apparatus of the invention is based on an opto-transistor array, a comparator array and an encoder and latch clocked by the raster-scan pulses of the display driver, which are configured to construct a pairing table of sequential source corneal reflections to sensor activations over the display field refresh cycle. An accurate three dimensional ocular model is computed from opthalmometric techiniques from which the viewing direction and fixation duration are derived. The apparatus is easily extended to the simultaneous tracking of both eyes and is designed to be used with head-mounted video displays. The accuracy of the apparatus is independent of shifts of the helmet on the user's head. Additionally, the apparatus is readily incorporated into panel mounted displays and head-free sensor arrays. The apparatus can be used as an eyetracker to control computerized machinery by ocular gaze point of regard and fixation duration.

10 Claims, 13 Drawing Sheets

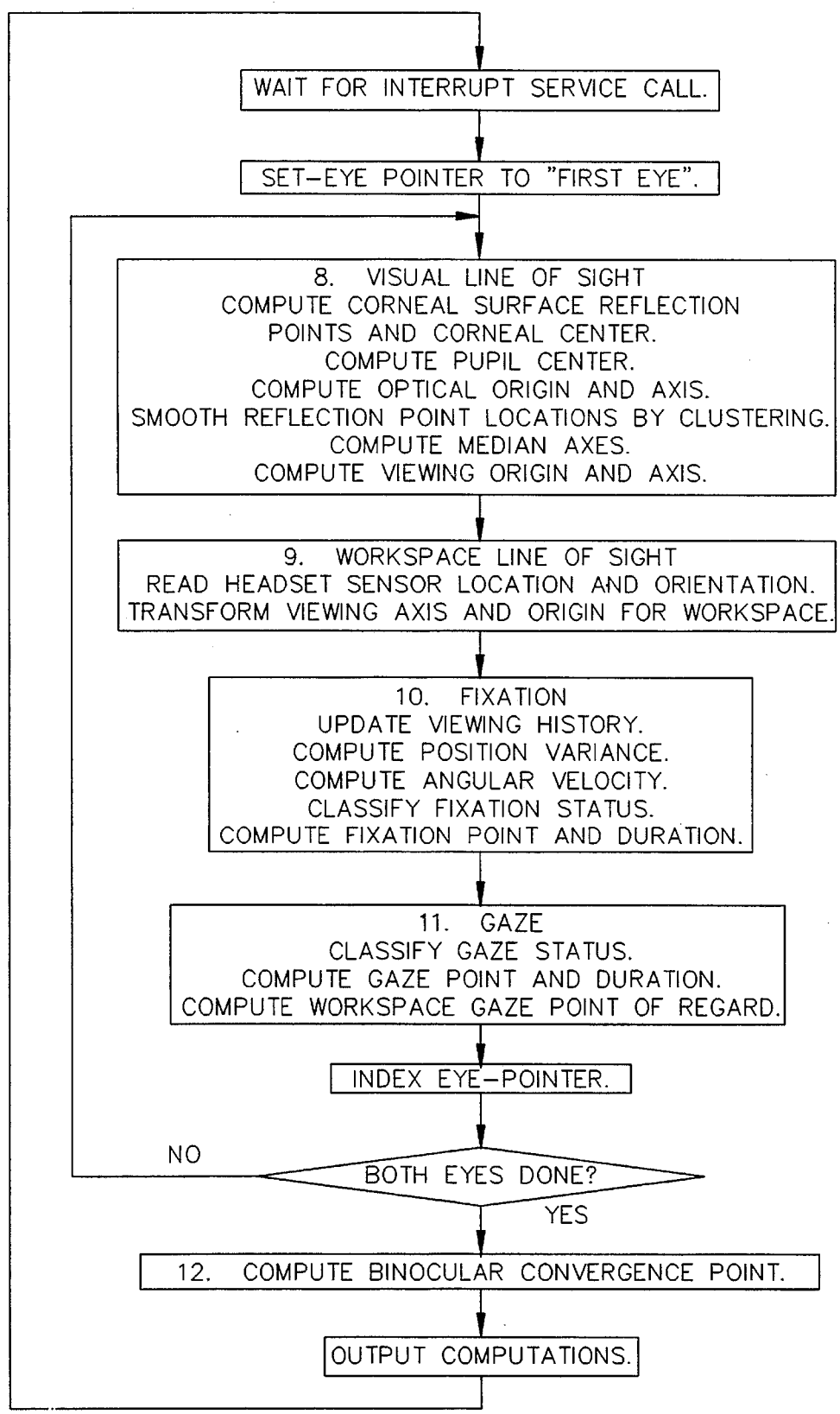
FIGURE 6. FLOWCHART FOR DIGITAL COMPUTER ROUTINES

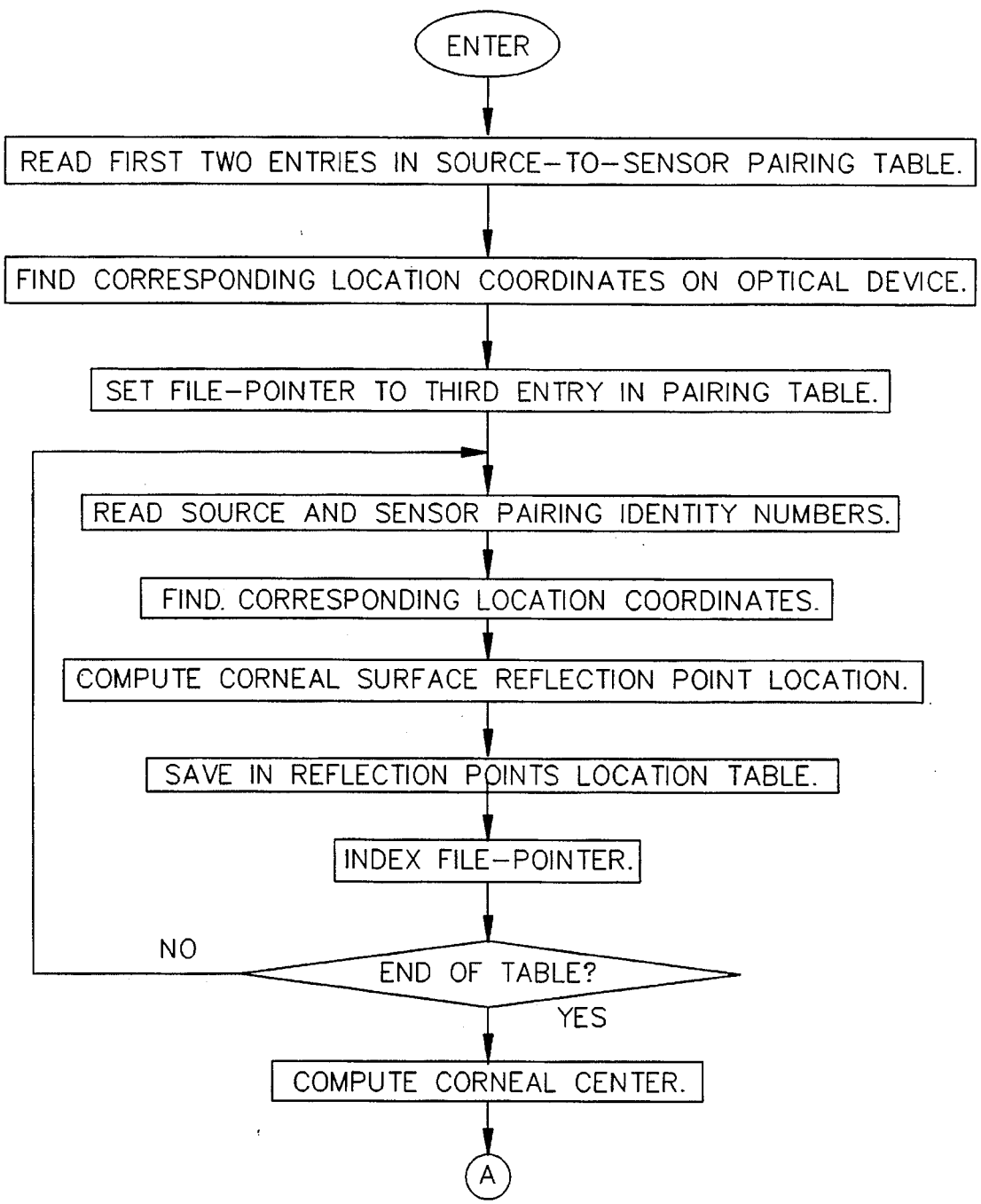
FIGURE 7A. FLOWCHART FOR DIGITAL COMPUTER ROUTINE 8

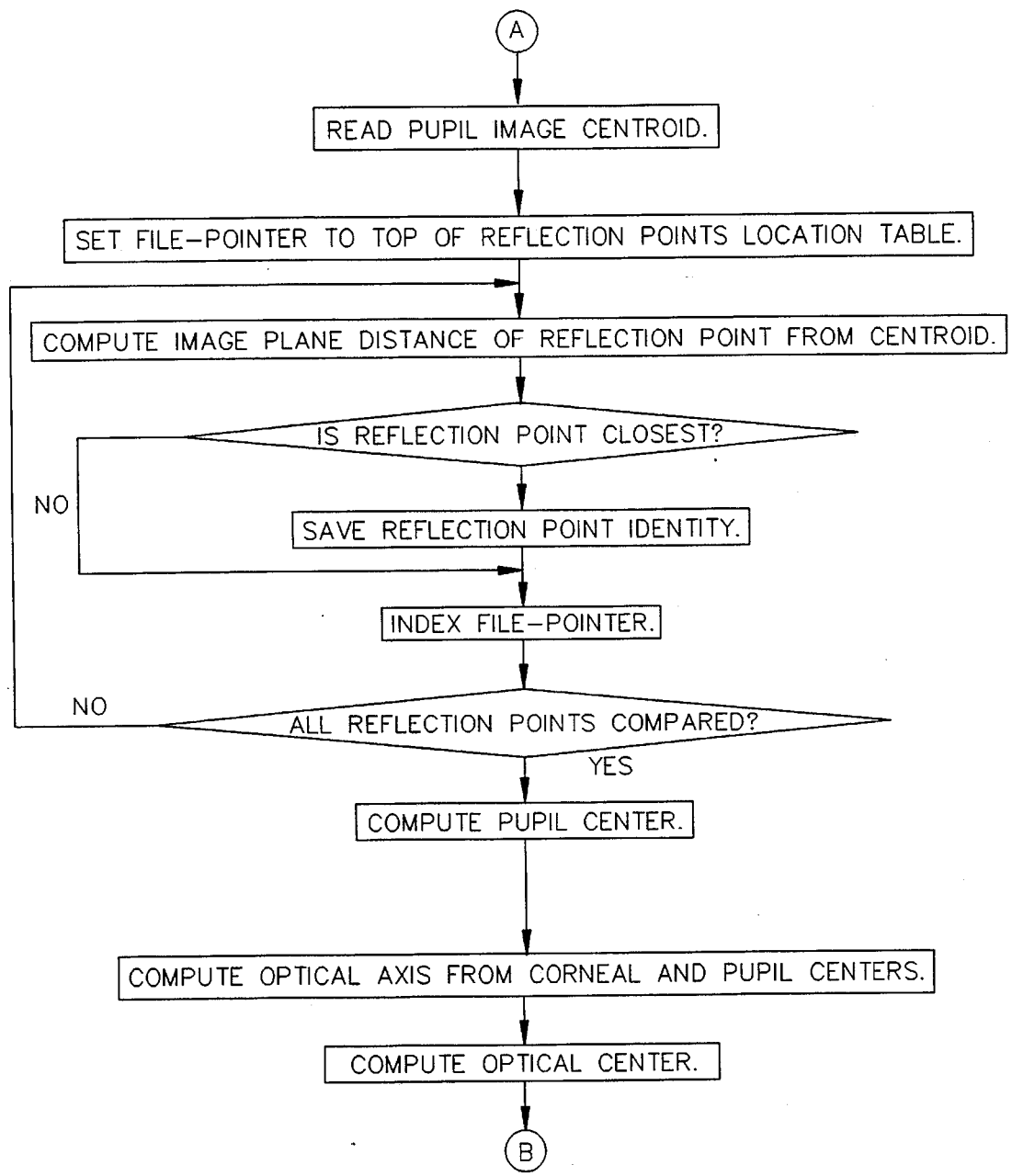
FIGURE 7B. FLOWCHART FOR DIGITAL COMPUTER ROUTINE 8

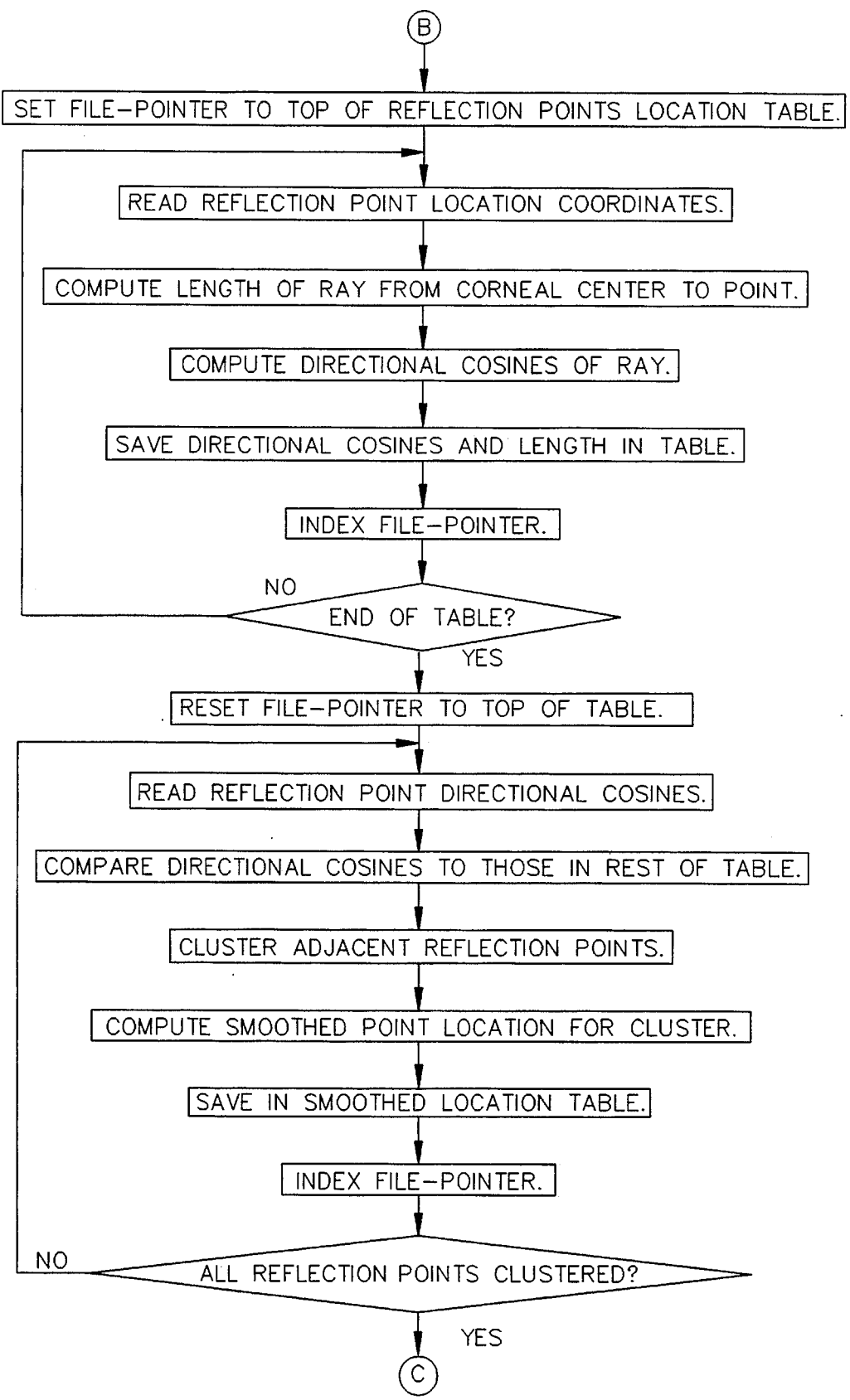
FIGURE 7C. FLOWCHART FOR DIGITAL COMPUTER ROUTINE 8

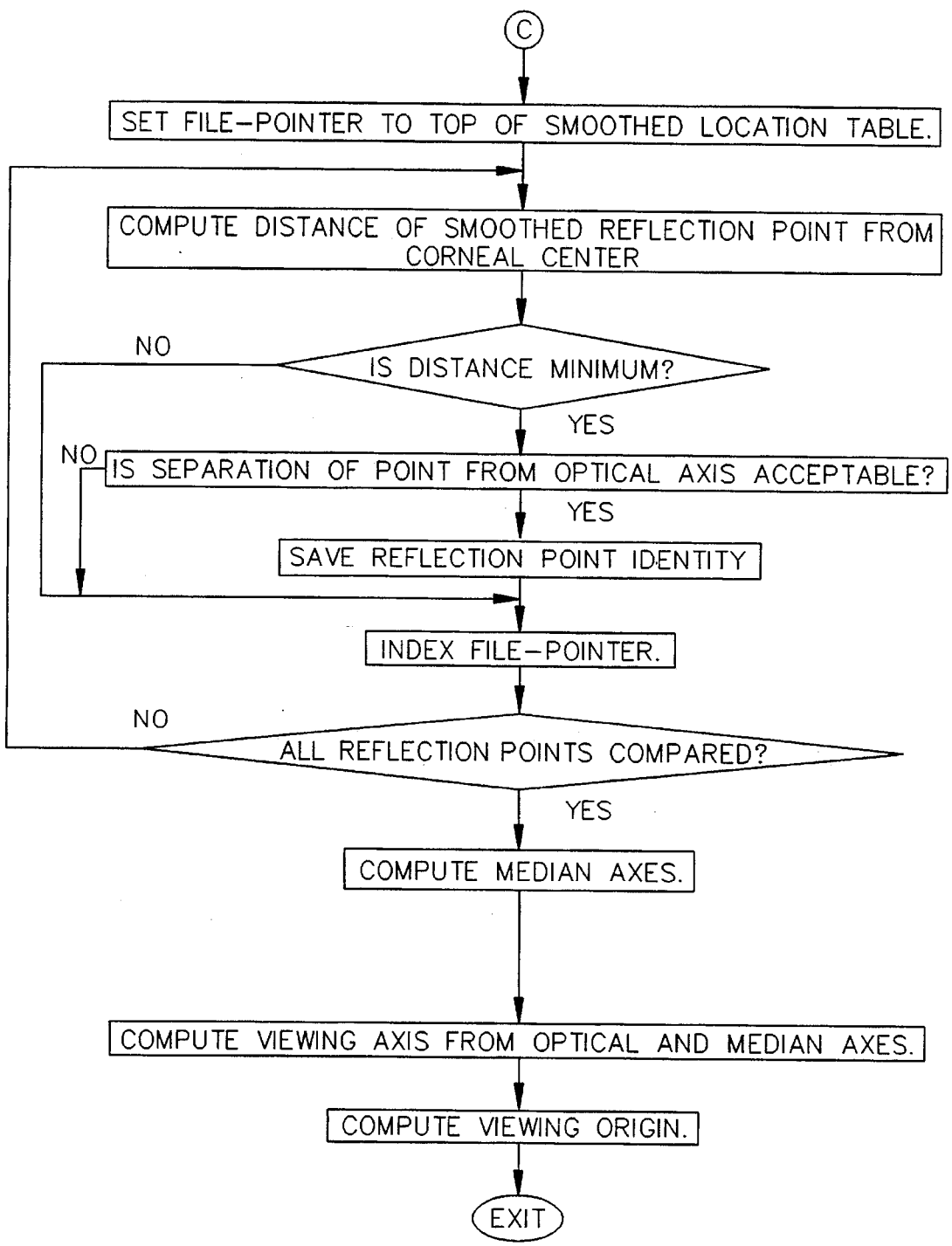
FIGURE 7D. FLOWCHART FOR DIGITAL COMPUTER ROUTINE 8

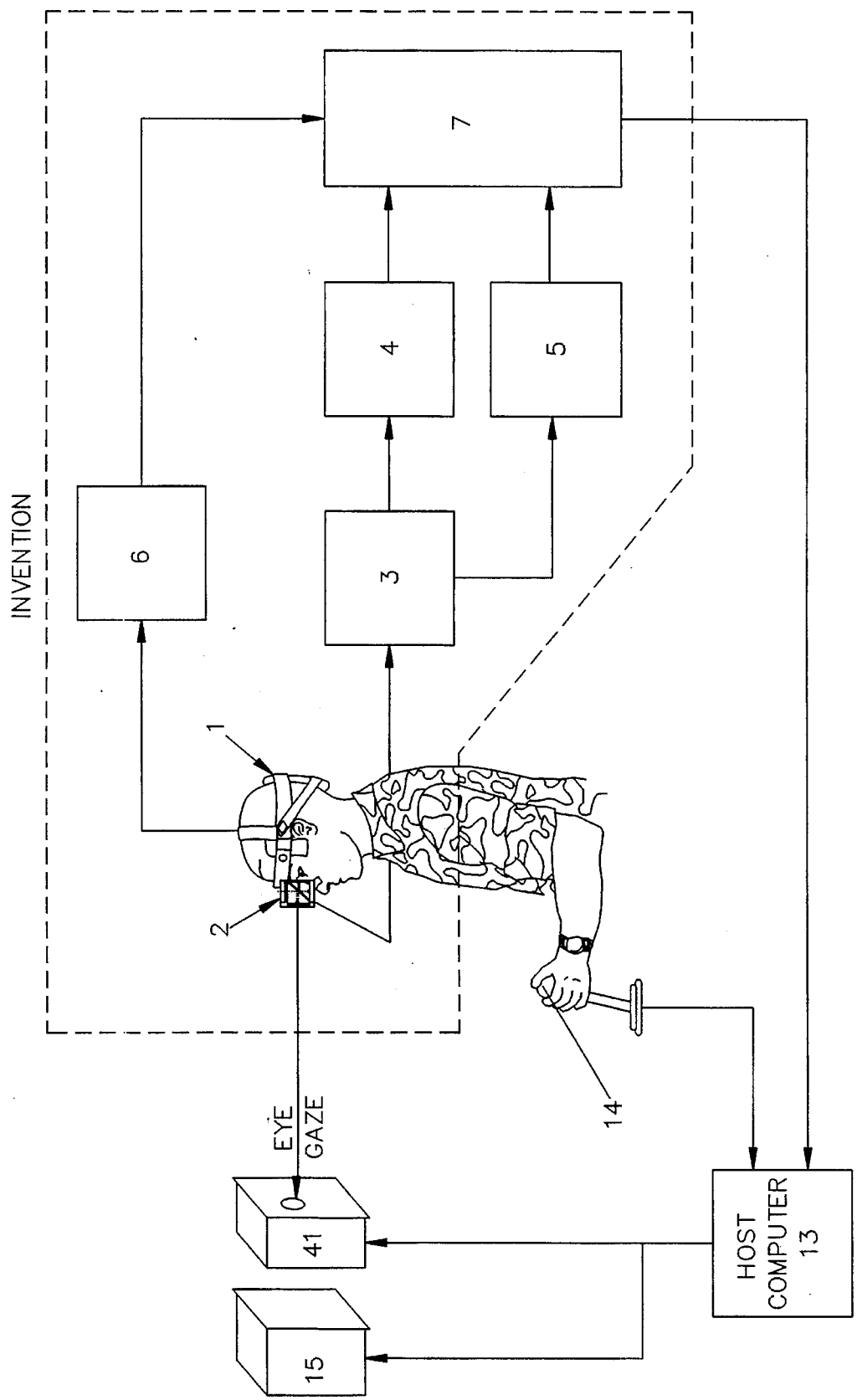

5,583,795

APPARATUS FOR MEASURING EYE GAZE AND FIXATION DURATION, AND METHOD THEREFOR

BACKGROUND OF THE INVENTION

(i) Technical Field of Invention

The invention is a form of oculometer and as such can be used to measure eye gaze and fixation duration as well as the dual eye binocular convergence point, and as such has potential applications in the medical, scientific, engineering, manufacturing, military, and entertainment fields. The apparatus may be used as a tool for medical diagnosis of ocular functions, as an aid to the paraplegic or handicapped, for the measurement of ocular functions and workload in human factors studies, as a measure of subject training, as a tool for fatigue monitoring, as part of an electronic safety net to detect performance degradation due to pilot incapacitation in piloted and teleoperated vehicles, as a component of an electronic intelligent pilot-vehicle interface used for situation awareness aiding in piloted and teleoperated vehicles, for task scan analysis including measuring situation awareness, for human operator control of machines and computer games, and for advertisement and usability analysis.

The invention is used with head-mounted video displays such as those developed for virtual reality, stereographic displays, monocular or binocular vision helmet mounted displays, and night vision goggles used in piloted helicopters, vehicles, and teleoperated robotics control stations. The invention can be used as an eyetracker to control computerized machines from an electronic video display by the ocular gaze point of regard and fixation duration.

Examples of machine control by ocular functions include updating computer generated information displays, selecting panel switches and instruments, controlling the fidelity of computer generated imagery scene inserts in simulations, controlling the viewing direction of remotely located cameras, controlling the movement of teleoperated robotics platforms or vehicles, selecting display subareas for automated scene analysis in aided target recognition, designating targets from direct sight or from a sensor display, and weapon system pointing.

The invention has particular applications to time shared concurrent tasks where the hands are involved in a continual time critical pilotage task and the eyes may be used intermittently to control a discrete task. The use of this invention enables both tasks to share a common visual working area with overlaid visual images. In this way, task interference is reduced by dedicating eye-movements and visual attention to the same working surface.

An example of such an application would be single pilot nap-of-earth low-level helicopter flight while updating onboard heads-up displays. A similar application is teleoperations of remote vehicles from video displays with camera control. Another such application is to the operation of completely enclosed armored vehicles with "transparent" or "see through" armor where the operator sees a video projection of the outside scene as recorded by externally mounted cameras and relayed to internal monitors; the operator would use the invention to control displays overlaid on the scene projection while concurrently performing the vehicle pilotage task. Similar comments apply to the piloting of "glass cockpit" designs for completely enclosed high performance aircraft.

(ii) Description of the Prior Art

The existing technology for oculometers is based upon the optical measurement of reflected infrared light from the human eye, and is more than thirty years old in concept. In its present form, an oculometer contains a single infrared light source which is directed at the eye and the reflected light is imaged onto a charge-injection (CID) or charge-coupled device (CCD) sensor array. The image of the eye is then electronically processed to determine the corneal reflection, the pupil centroid orientation, or both. These parameters are used to determine the angular location of the eye relative to the camera within a fair degree of accuracy. The technology is either head-mounted or mounted in a panel in front of the user.

The head mounted systems are awkward to wear. The accompanying optics are bulky and heavy, limited in field of view, and induce neck and shoulder muscle fatigue. The infrared light source is placed next to the eye; a filter shields the source, eye, and sensor from the ambient light. The arrangement limits and interfere with the visual field. The boresight established in calibration, is easily perturbed by head movement or vibration induced disturbances in the head support system. In addition, adjustment difficulties may occur with individuals having a large nose bridge, deep lying eyes, bulging eyes, jutting eye lids, or other extreme deviations in facial structure.

These limitations become apparent when integrating the present technology with helmet mounted displays. Recent advances in display technology have produced extremely light weight helmet mounted displays comparable in size to bulky sunglasses. The eye relief distance is specified in millimeters and there is little room between the display and the eye for placing the infrared sources and fiber optics probes used with the present technology.

The optics for the panel mounted system are mounted in front of the user and directed toward his face. The panel mounted system is limited to low ambient light levels and objects that the user may need to work with can not be placed between his face and the optics. A servomechanism is used to keep the optics aligned on the user's eye, and the servomechanism adjustment is noticeable to users following head movement. Excessive head movements and interference of the optical path by facial features such as the user's nose, are not tolerated.

The oculometer determines the angular location of the eye relative to the sensor array within a fair degree of accuracy. The measurement of head position and orientation for the head-mounted system allows the determination of eye position and orientation in the workspace, and therefore the computation of eye point of regard. Similarly, the determination of the range from the sensor to the eye by either ultrasonic or image focusing allows the computation of eye point of regard for the panel system. The accuracy of the technology is roughly about +/− one degree in practice; a lower limit appears to be about +/− 0.75 degree.

The oculometer is used to determine the location of the user's visual attention; it can be used to select display icons in machine control. The user may be looking over a display or scene to acquire task related information in preparation to initiating machine control. Some other means is usually required for the subject to indicate that a particular display element or scene feature has been selected by him for machine action. For example, the user may perform a motor function in conjunction with a forced gaze at a selected item, by pressing a switch or speaking a voice command to an automatic speech recognizer.

Exemplary of existing technology include U.S. Pat. No. 3,986,030 to Teltscher which discloses eye-motion operable keyboard-accessory includes light source means for directing a light ray at the eye of an operator, for obtaining a light reflection there from, and a plurality of light-responsive sensors selectively actuable by the operator reflected light ray. U.S. Pat. No. 4,109,145 to Graf discloses an apparatus that is controlled by movement of the eye which using a line of sight detecting apparatus such as an oculometer produces signals indicative of the direction along which an operator is looking and positions a display for viewing by the operator. U.S. Pat. No. 4,209,255 to Heynau et al. disclose single source aiming point locator using a single source light emitting diode (LED) mounted on the helmet of a pilot in an aircraft, which can be used to designate a point on a display from photodiodes located adjacent to the display. U.S. Pat. No. 4,623,230 to Weinblatt discloses media survey apparatus and method using thermal imagery to monitor visual observation of a transitionally viewed display by directing infrared radiation from behind the display into the path of travel of a moving observer and detecting the retinal eye reflections from the observer when he is viewing the display. U.S. Pat. No. 4,648,052 to Friedman et al. discloses an eye-tracker communication system based on a system for computer vision comprising a source of digitized video signals and a frame encoder circuit which encodes threshold crossing events in eye fixations on a two dimensional area within the frame and stores the results in a cache memory. U.S. Pat. No. 4,761,071 to Baron discloses an apparatus and method for determining the corneal and scleral topography by a plurality of triangulations each made to determine the elevation of a different location on the surface of the eye from a positive sensitive detector of known orientation and an incident narrow beam of light with known position and direction, which illuminates a fluorescent substance instilled on the surface of the eye. U.S. Pat. No. 4,973,149 to Hutchinson discloses an eye movement detector utilizing an infrared light emitting diode mounted coaxially in front of the lens of an infrared sensitive video camera for remotely making images of the eye of a computer operator. U.S. Pat. No. 5,035,500 to Rorabaugh et al. disclose an automated ocular perimetry, particularly kinetic perimetry, which using a single visual light source moved with a x-y plotter under computer control to discrete positions within the visual field of a subject, has the subject indicate detection of other light sources positioned in a regular array and momentarily illuminated at various times, while the subject is fixating the first light source. U.S. Pat. No. 5,170,153 to Migozzi et al. disclose an optical device for the display of light data collimated to infinity which uses an oculometer to determine the pupil center of the eye and an automatic control circuit to adjust the position of the display image so that it is centered over the pupil. U.S. Pat. No. 5,220,361 to Lehmer et al. disclose gaze tracking for field analyzer through automated video surveillance of the patient's eye from an infrared source mounted in the center of the test screen to the front of the patient, and the video measurement of corneal reflected light and the computation of the pupil chord to determine the gaze direction. Adams, C. (1990). "If looks could kill: the eyes have it". *Military & Aerospace Electronics.* (Mar) 35–37. Reviews infrared light source oculometers and the potential for use by pilots of military aircraft in designating targets by eye gaze. Anliker, J. (1976). Eye movements: on-line measurements, analysis, and control. In R. A. Monty & J. W. Senders (Eds.), *Eye Movements and Psychological Processes.* (185–199), Hillsdale, N.J.: Lawrence Erlbaum Associates. Describes automatic fixation and saccade detector classification schemes. Calhoun, G., Janson, W., & Arbak, C. (1986). "Use of eye control to select switches". *Proceedings of the Human Factors Society 30th Annual Meeting,* Dayton, Ohio. Describes the experimental results and limitations of pilots using a head mounted infrared light source oculometer for selection of panel switches in a fighter aircraft simulator. Goode, P. W. (1984). "Eye Directed View". 21*st Space Conference,* Kennedy Space Center. Describes experimental results of using an infrared light source oculometer for control of remote camera viewing direction. Jacob, R. J. K. (1989). "What you see is what you get: the use of eye movements in human-computer interaction techniques". Washington, D.C.: Naval Research Laboratory. Describes techniques and limitations of using a panel mounted infrared light source oculometer for control of computer driven displays by eye fixation and gaze duration. Smyth, C. C. & Dominessy, M. E. (1989). *Comparison of oculometer and head-fixed reticle with voice or switch and touch panel for data entry on a generic tactical air combat display* (Technical Memorandum 21–89). Aberdeen Proving Ground, Md.: U.S. Army Human Engineering Laboratory. Describes the experimental results and limitations of using a head mounted infrared light source oculometer for control of computer driven displays by eye fixation and switch or voice commands.

SUMMARY OF THE INVENTION

It is an objective of the invention to provide an apparatus that can be used as an eyetracker to control computerized machinery by ocular gaze point of regard and fixation duration, this parameter may be used to pre-select a display element causing it to be illuminated as feedback to the user. The user confirms the selection with a consent motor response or waits for the selection to time out. The ocular fixation dwell time tends to be longer for display element of interest.

It is an objective of the invention to overcome disadvantages of existing technological by incorporating oculometers into head mounted electronic video displays at a lower cost, increased accuracy, rapid response, slight bulk, light weight, relatively free field of view, and increased ease of application and calibration.

It is yet another objective of this invention to provide an apparatus that is auto-calibrating thus allowing the user to quickly and accurately go through a calibration procedure that correlates visual fixation position with line of sight.

It is yet another objective of this invention to provide an apparatus whose accuracy is independent of shifts of the helmet on the user's head; theses shifts are caused by changes in facial expression and head movement dynamics. This is due to the ability to compute an exact eye model from the locations of the light sources and the sensors which are fixed by the helmet-construction. Measurements of the helmet location and orientation are used to relate the visual axes to the user's three dimensional workspace.

It is another objective of the invention to provide an apparatus that uses an electronic video display array as an accurate and rapid sequence of point light sources. This reduces the components needed for eye-tracking since the light imaging system is used to illuminate the eye in a controlled manner.

It is yet another objective of the invention to utilize a video imaging system that may be active emitter (CRT, thin-film electroluminescence phosphor, plasma panel) or passive (Liquid crystal) including active matrix. In all of these cases, the oculometer makes use of the initial flare of illumination common all of these sources either due to emission or crystal realignment, that occurs as each display pixel is refreshed in an orderly sequence. In a similar manner, the apparatus of the invention may instead use an array of near-infrared light emitting diodes turned on and off in sequence as an illuminating source.

It is yet another objective of the invention to provide an apparatus that employs a realistic model of the eye, derived from physiologic optics, to accurately determine the optical axes and the corresponding visual line of sight. The computations needed for this derivation are based on the measurements of the multiple sequence of light reflections from the cornea and internal components of the eye.

It is yet another objective of the invention to replace the sensor image focusing and processing used in prior technology with a simple array of photo-transistor light sensors and amplifiers directed toward the cornea of the eye. The objective further includes using this opto-transistor array, a comparator array and an encoder and latch clocked by the raster-scan pulses of the display driver, to construct a pairing table of sequential source corneal reflections to sensor activations over the display field refresh cycle. The pairing table listings of reflections is used to compute an accurate three dimensional ocular model which for each display field refresh cycle, locates the corneal center and optical axis as well as the corneal orientation from the major and minor axes. The visual origin and axis is then computed from these parameters.

It is yet another objective of the invention to easily integrate the apparatus with a miniaturized CID/CCD video camera coupled with image processing to acquire an eye image. Ophthalmometric techniques are used to locate the pupil center as an additional parameter for the computation of the optical axis. In addition, the pupil diameter can be measured for workload measurements.

It is yet another objective of the invention to provide an apparatus that can easily extend to simultaneously track both eyes, thereby allowing measurement of the optical convergence point in the user's three dimensional workspace (real or virtual).

It is yet another objective of the invention to provide an apparatus and method that is particularly attractive for measuring ocular functions with virtual image displays such as helmet mounted displays and night vision goggles. However, the invention is readily incorporated into panel mounted displays and head-free sensor arrays.

BRIEF DESCRIPTION OF THE DRAWINGS

FIG. 6 is a flowchart for the digital computer routines.

FIGS. 7a–d are flowcharts for the computer routine used to compute visual line of sight.

FIG. 8 is a schematic showing a method for using the invention as a computerized machine controller.

DETAILED DESCRIPTION OF THE PREFERRED EMBODIMENTS

Figure 1:
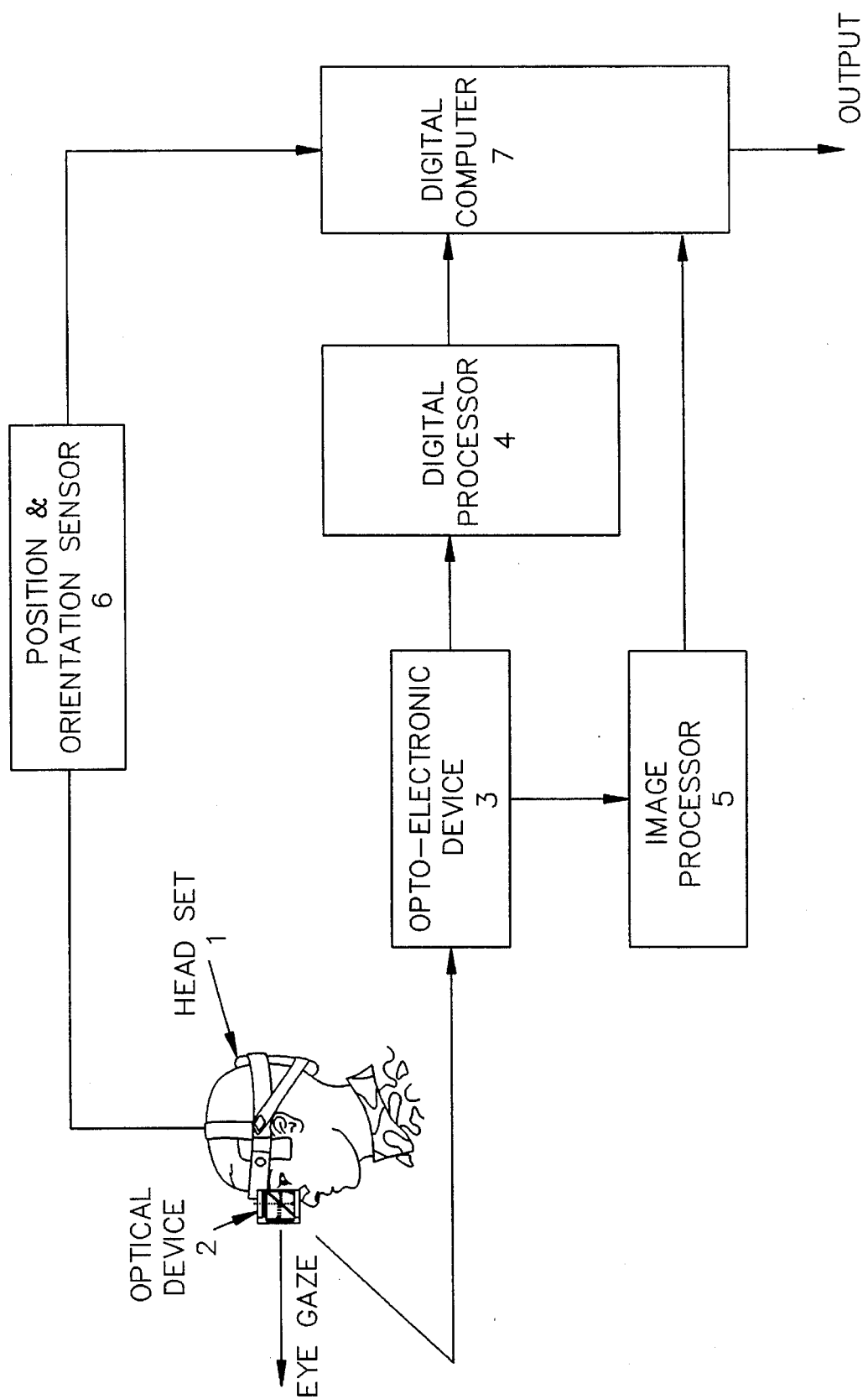
FIG. 1 is a schematic drawing of the invention showing the hardware components.
Figure 2:
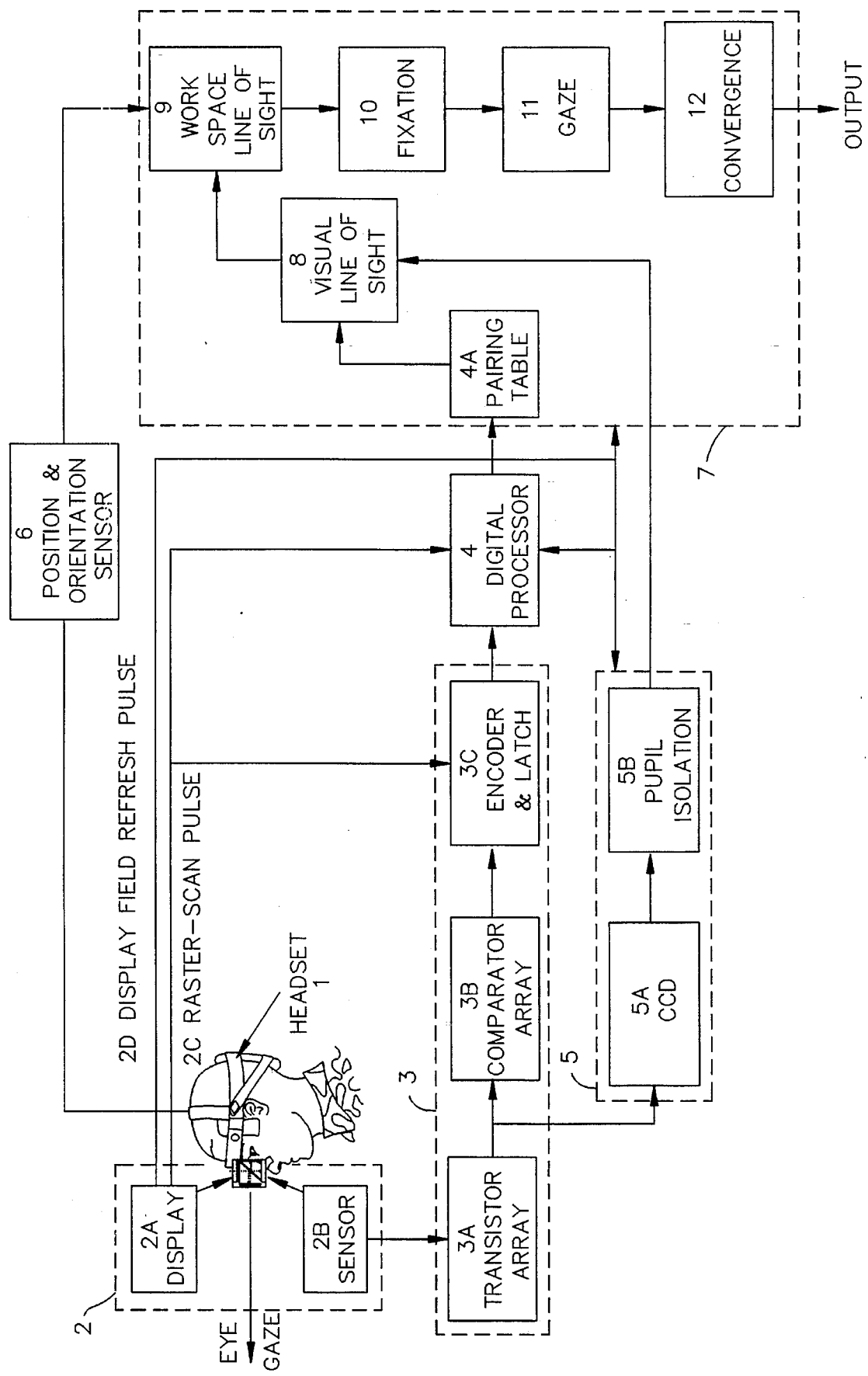
FIG. 2 is a detailed drawing of the enhanced schematic showing the electronic hardware and software components.

The invention consists of a headset 1, a video device 2 mounted on the headset, an opto-electronic device 3, a digital processor 4, an image processor 5, a headset position and orientation sensor 6 and a digital computer 7. Video device 2 holds a video display 2a and an sensor system 2b. Video display 2a illuminates the user's eye while the sensor system 2b detects the reflections from the eye. The optical output of the sensor system 2b is the input to the opto-amplifier array 3a of opto-electronic device 3. The electrical output of the array 3a is the input to comparator array 3b which in turn provides electrical input to encoder and latch 3c. The electrical output of encoder and latch 3c is the electrical input to digital processor 4. Comparator array 3b isolates amplifier element 3a responding to the instantaneously illuminated element of video display 2a, and processor 4 writes the encoded address from latch 3c to a double buffered digital memory shared with digital computer 7, on the clocked raster-scan pulse 2c from the video display 2a. The electrical output of the array 3a is also input to the charge-coupled device (hereinafter referred to as CCD) 5a of image processor 5. The user's pupil centroid is isolated by processor 5b on clocked display-field refresh pulse 2d from video display 2a, and the electrical output is digital input to the digital computer 7. The electrical output of the headset position and orientation sensor 6 is digital input to the computer. The digital computer runs several processes which are released from hibernation upon the clocked display-field refresh cycle pulse 2d from the video display 2a; these are routines to compute: the visual line of sight 8, the workspace line of sight 9, fixations 10, gaze points 11 and finally the binocular convergence point 12 for the dual eye system.

The invention uses electronic video display 2a to illuminate the eye in a controlled manner. The sequence of momentary flares in display pixel brightness, generated during the electronic refresh sweep of display 2a, provides an accurate and rapid sequence of point light sources. This use of video imaging system reduces the components needed for eye-tracking. The video imaging system 2 may be active emitter such as a cathode ray tube, solid phosphor thin-film electroluminescence, gas discharge plasma panel or passive emitter such as a liquid crystal display including active matrix. The invention makes use of the initial flare of illumination common to all of these sources due either to emission or crystal realignment, that occurs as each display pixel is refreshed in an orderly sequence. Furthermore, the invention may be extended to light emitting diode displays where the display elements are re-drawn sequentially at a video rate. The only requirement is that an momentary increase in brightness occur during electronic refresh of the display pixel element. The momentary flare in brightness detected by electronic sensor systems is not noticed by the human eye, which averages out transients in brightness less than 0.10 seconds.

The display 2a refresh illuminance conditions depend upon the display medium such as the CRT display phosphors, LCDs or LEDs. The CRT display phosphors generally have a electron beam refresh excitation rise time on the order of several hundred nanoseconds, a fall time on the order of several microseconds, and a decay time on the order of a millisecond. However, more than 90 percent of the illuminance energy is emitted within the first few microseconds and each pixel is dark most of the time. The CRT display is point addressable to maintain pixel spatial compactness. Similar comments apply to thin-film electroluminescence phosphor displays. In contrast, the rise and fall times of liquid crystal displays to electrostatic refresh is on the order of several milliseconds. LCDs are generally interspaced matrix line addressable in which all display elements in a row are refreshed as the column lines are set at the appropriate voltages. Whereas most display designs set the column lines on the same refresh clock pulse, they with little difficulty could be set sequentially at a video sweep rate with no display degradation. Finally, light emitting diodes used in display matrixes have an on-rise time and off-fall time on the order of several hundred nanoseconds. Again LED displays could be refreshed on and off in a vertical and horizontal synchronized manner.

Figure 4:
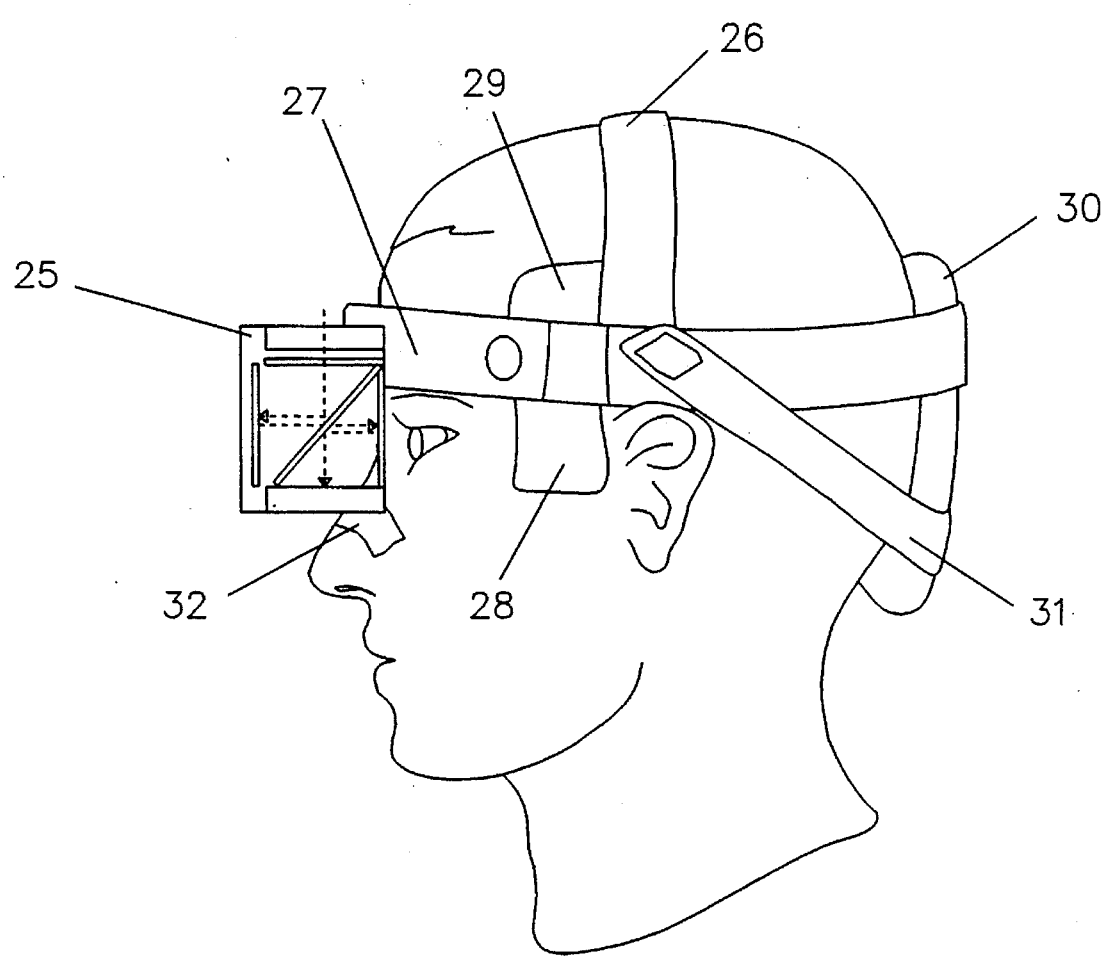
FIG. 4 is a drawing showing headset design.

The video display 2a may be incorporated into a head mounted display system; FIG. 4 shows a headset 1 design for a virtual reality display. The user is wearing a head-mounted electronic video display 2a and a periocular array of light sensors 2b all packaged as a complete unit 25. In this case, the unit 25 is supported by a headset 1 which is designed for stability with headbands 26 and hatbands 27 each having contact pads 28 through 31 located on the load bearing portions of the face and head. The load bearing portions of the face and head include cheek bones, having contact pad 28, temporal regions having contact pad 29, the back of the head having contact pad 30, and the inion budge at the rear of the skull having contact pad 31. These skin surfaces are essentially devoid of flesh and muscle unlike the rest of the human face which is extremely pliable forming an unstable base. Contact pad 29 forces hat band 27 to stand off of the forehead. This in done to prevent eyebrow movement from disturbing the settings. Unit 25 houses display 2a optics and sensors 2b, which is supported on the nose bridge 32 by pivot joints located at the sides of hatbands 27. Unit 25 can be rotated up out of the user's field of view.

Figure 5A:
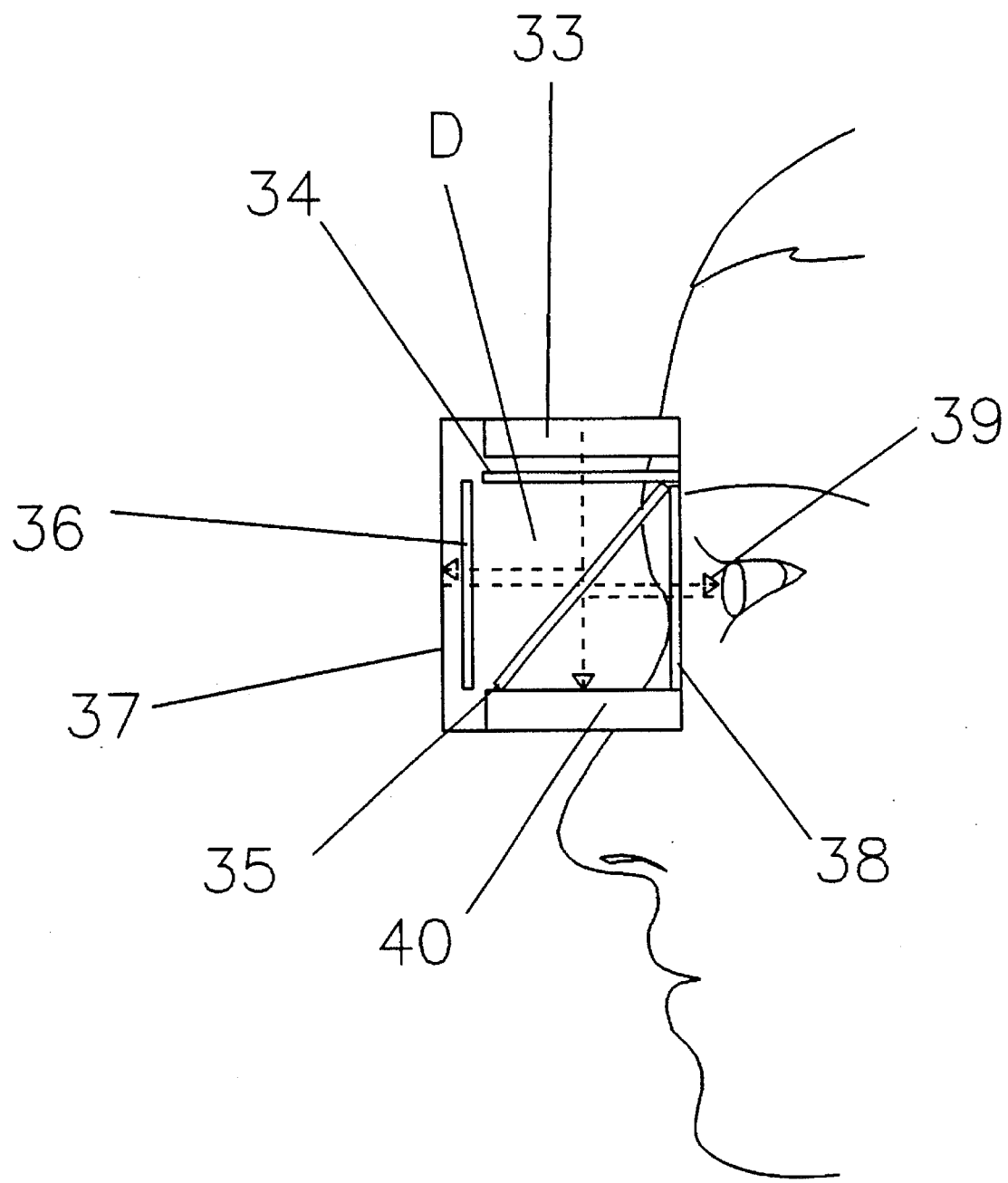
FIGS. 5a–c are drawings showing various configurations for the headset mounted optical device of the invention.
Figure 5B:
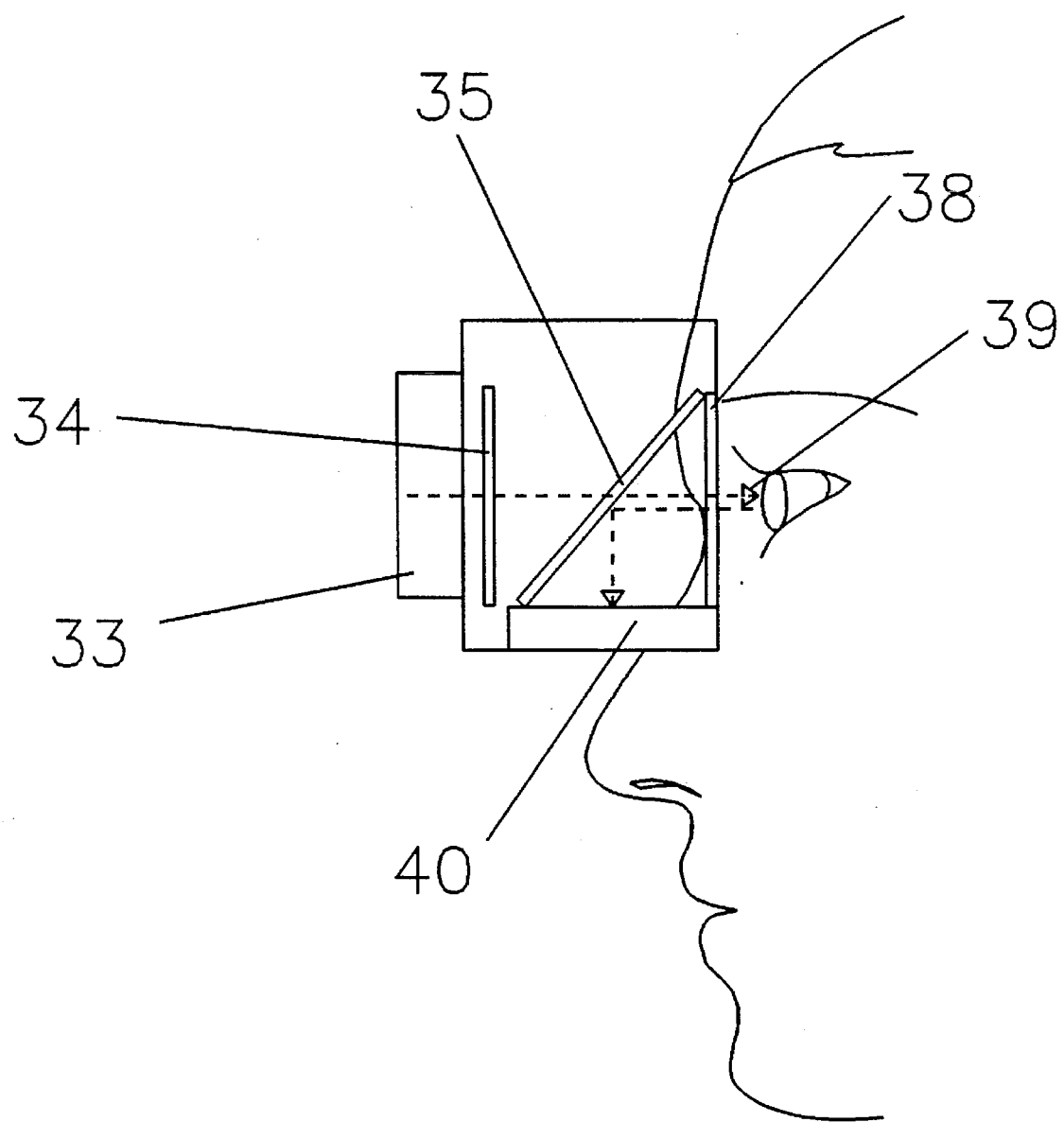
Figure 5C:
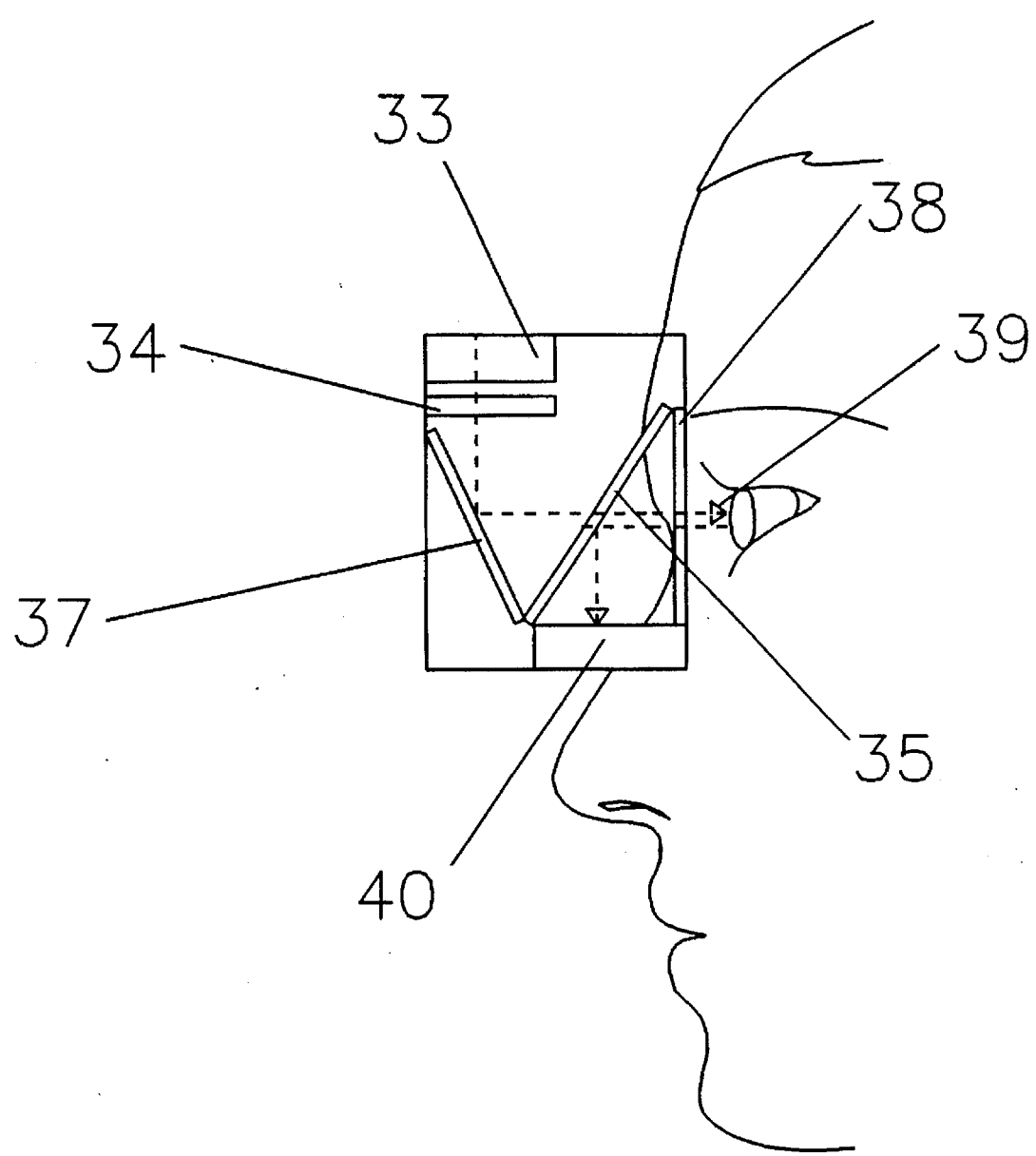

As shown in FIG. 5a, the video display 2a image light reflected from the user's eye is directed back to the periocular array of light sensors 2b of the optical device 2 by display optics D. The periocular array of light sensors 2b detects the display 2a generated light reflected from the cornea and inner structures of the user's eye. The particular optical design for the sensor array 2b is determined by the video display 2a design of which the sensor unit is a part. A virtual display 2a design shown in FIG. 5a employs an on-axis folded optical geometry. In this case, the light from video display 33 is focused through a dielectric polarizer 34 and folded at a semi-reflective mirror/splitter 35. The light then passes through a quarter-wave polarization rotator (wave plate) 36 to the front visor/combiner 37. The light reflected from the visor 37 passes back through the wave plate 36 and with the light's Electric-vector now rotated 90-degrees, passes back through the splitter 35, from which it passes through another wave plate 38 to the eye 39. The light reflected from the eye 39 passes back through the wave plate 38, and with the Electric-vector now rotated another 90-degrees, is folded by the mirror/splitter 35 onto the periocular array 40 of light sensors 2b. The array of light sensors 2b detects the display generated light reflected back from the cornea and internal components of the eye such as the crystalline lens and the iris surrounding the pupil. FIGS. 5b and 5c show several other designs for the optical device where similar comments apply to the optical geometry. In all designs, the light reflected from the eye 39 passes back through the wave plate 38, and is folded by the mirror/splitter 35 onto the periocular array 40 of light sensors 2b.

The light sensor array 2b uses a fiber-optics bundle probe to acquire an eye image. The output of the optics probe feeds a two-dimensional array of photo-transistors 3a. A spectral filter is used to ensure that only light of the appropriate wavelength from the display 2a is collected. The simple array of photo-transistors 3a instantaneously converts the reflected light to an electrical current. The photo-transistors 3a detect the corneal reflex (first Purkinje image) of the light source from the outer surface of the cornea. The incident light is specularly reflected from the spherical anterior surface of the cornea to create a virtual image of the source. The corneal reflex has a bell-shaped light distribution with the brightest part at the center of the image corresponding to the reflection point.

The sensor array 2b output is piped through the amplifier array 3a to an array of comparators 3b where the amplified output of each photo-detector 3a is compared to a threshold level. The threshold level is set to collect the brightest part of the image. The level is set above the system noise which is mainly due to optical reflections from the other sources, the photo-transistor dark noise, and the Schottky, Johnson, and flicker noises in the amplifiers. Comparator array 3b is interfaced to a matrix array static encoder 3c. A comparator voltage output above the threshold level forces the corresponding matrix address on the output lines of the encoder 3c. The encoder output code is latched for the remaining duration of the raster scan clock pulse 2c. In this way the electronic encoder 3c isolates the photo-transistor 3a with maximum response to the corneal reflex from the instantaneously excited light source 2a. The encoder latch is reset by the next raster scan clock pulse 2c; the reset is momentarily delayed to allow interaction with the digital processor 4.

The electrical output of the latched encoder 3c is the electrical input to the digital processor 4. On the raster scan clock pulse 2c from the video display 2a, the processor 4 writes the encoded address from the latch 3c for the light sensor 2b matrix address to a double buffered digital memory 4a shared with the digital computer 7. The vertical and horizontal matrix address of the corresponding video display 2a pixel element is determined by the display refresh order, which is indexed by the raster scan clock pulse 2c count. The process is repeated by processor 4 during the display refresh cycle, producing a digital memory table 4a of array matrix addresses for photo-transistor sensor 2b and light source 2a pairings, which is accessible by the digital computer 7 routines. The digital memory 4a is buffered and the raster scan clock pulse counter is reset to zero on the clocked field refresh pulse 2d.

The digital computer runs several processes which are released from hibernation upon receipt of the display field refresh clock pulse 2d from the video display 2a. These are routines to compute: the visual line of sight 8, the workspace line of sight 9, fixation status 10 and the gaze point 11 for each eye. The routine 8 computes the visual line of sight relative to the optical device 2. The routine 9 reads the headset position and orientation from sensor 6 and transforms the visual line of sight to that for the real or virtual workspace which the user views through visor 37 of optical device 2. Routine 10 maintains a running record of the line of sight and classifies the eye patterns as fixations, saccadic movements, or pursuit tracking. Finally, routine 11 groups the eye fixations into cognitive meaningful gaze points and movements. The binocular convergence point 12 is then computed for the dual eye system. The gaze points for both eyes determine the binocular point of convergence for the dual eye system.

Routine 8 is essential to the invention. Routine 8 is based on a three dimensional model of the eye derived from the corneal light reflections and pupil image data. The routine calls on a set of subroutines which computes the corneal center and surface reflection points 8a for the display refresh cycle 2d, the pupil center 8b, the optical origin and axis 8c, smoothing of the reflection points 8d, the median axes of the corneal surfaces 8e and the viewing origin and axis 8f. Subroutine 8a makes use of the memory sensor 2b-source 2a pairing table 4a and the optical device 2 geometry. The subroutine 8b uses the pupil centroid output of the processor 5b for the computations as well as the pairing table 4a. The optical origin and axis result from the corneal and pupil centers. Smoothing of the reflection points are required for the median axes computations. Finally, the visual line of sight is computed from the optical origin and the optical and corneal median axes.

The three dimensional model of the eye used in routine 8 is based on expert knowledge briefly described as follows. The adult human eye is about 25 millimeters in diameter and set in an orbital socket in the skull. It is connected to and held in place by external muscles, nerves, blood vessels, and tissues. The sclera an envelope of tough white tissue, holds the eye mechanisms. The cornea is a transparent shield over the front of the eye. Vision occurs when light entering the eye through the cornea, passes through the pupil defined by the iris, and is focused by the transparent lens onto the retina, a lining of light sensitive nerve elements at the back of the eye connected directly to the optic nerve.

The center of rotation of the eye is located approximately 13 millimeters behind the front surface of the cornea. For normal, unaided viewing, the comfort limit for eye rotation from straight ahead is approximately 40 degrees. The surfaces of the optical elements of the eye are not perfectly spherical but are somewhat flatter at the peripheral edges than at the optic center. However, the cornea is nearly spherical within the central 30 degrees. The radius of curvature of the anterior surface of the cornea is 7.8 millimeters for the normal human eye, and 6.8 millimeters for the posterior surface.

The cornea and crystalline lens have optical axes that do not quite coincide, and the optical axes of the eye does not coincide with the visual axis (the line connecting the fovea to the point of fixation) by 5 to 7 degrees. Despite this complexity, for practical purposes the eye can be regarded as having four major refracting surfaces: the anterior and posterior surfaces of the cornea, and the front and back surfaces of the transparent lens. These surfaces may be regarded as spherical, with a common axis, and indices of refraction may be taken as constant within any given optical element. The refractive index of the cornea is commonly about 1.377; that of the aqueous humor and vitreous body within the eye is normally about 1.337.

The digital computer routine 8 computes the center of the corneal anterior surface in the optical device 2 coordinate system from the sensor 2b-source 2a pairings listed in the memory table 4a. As part of this computation, the routine converts the pairing table to a mapping of the corneal surface locations of the reflection points and the corresponding corneal radii for the tabulated pairing 4a of sources and sensors. The routine has in permanent memory the locations and orientations of the sensors 2b and light sources 2a in the optical device 2 coordinate system referenced by the appropriate matrices addresses. For example, the data file for a virtual image head mounted video display system contains the directional cosines of the image light from the display elements in the coordinate system of the video device 2 housing. The directional cosines are determined by the display optics operating on the fixed matrix of display elements in the video display 2a. Furthermore, the location and directional cosines for the sensors 2b are fixed in the display coordinate system by the sensor optics. These locations and directional cosines are computed prior to usage and fixed in permanent memory for the routine.

Figure 3:
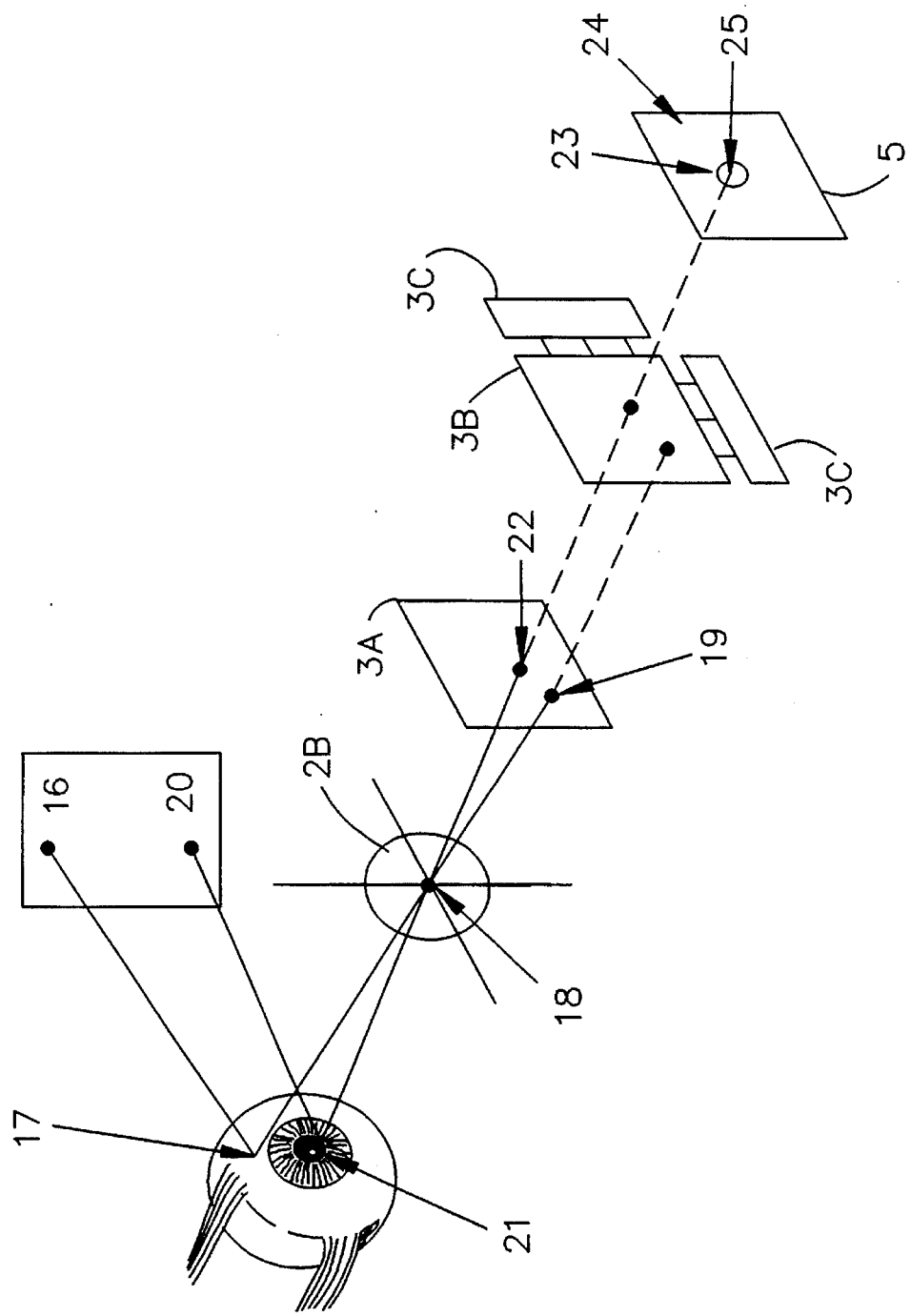
FIG. 3 is a schematic drawing of the invention showing the processing of the light reflected from the user's eye.

A set of five equations describes the relation between the center of the anterior spherical corneal surface and the orientation of the display light source 2a and the location and orientation of the sensor 2b paired at a corneal reflection point. The equations depend upon the type of video display 2a; the source position is specified for the direct view display, while the orientation of the source is specified for the virtual image display. Three of the equations relate the reflection point 17 to the corneal center, the source 16 orientation, and the sensor orientation 18 and location 19 as shown in FIG. 3. The application of Snell's law gives two more equations, one for the equality of the incident and reflection angles at the reflection point 17, and the other for the coplanar orientation of the source 16 ray, sensor 19 reflection ray 18, and the corneal surface normal at the reflection point 17. Another equation is given by the fact that the corneal surface normal has unit magnitude.

Tabulated data from three pairings 4a of emitting sources to sensors are needed for a solution; regression analysis techniques are applicable with data from more than three pairings. The equations are solved using numerical analysis techniques The output of the subroutine is the location of the corneal center in the coordinate system of the video device 2 housing for each display refresh cycle and the corneal radius and reflection point coordinates for each pairing in the table 4a during that cycle. The processor first solves for the directional cosines of the corneal surface normal at each paired reflection point using Snell's laws and the unit magnitude property; a unique solution is specified by the fact that the viewing direction is toward the display. The three equations relating the reflection point coordinates to the emitting source and receiving sensor are then solved for the corneal center and the reflection points radii using the data from three or more pairings.

Given the corneal center, the optical axis may be estimated from the difference between the center and the theoretical rotational point for the eye in the optical orbit of the skull. The rotational point may be assumed fixed in the head coordinate system and may be determined in calibration. However, in actuality, the eye rotational point will shift slightly in the optical orbit of the skull with muscular tension and rotational movements. These translational shifts can produce severe displacements in viewing direction; for example, a 0.1 millimeter shift in rotational point can produce a 1.4 degree shift in viewing direction. Furthermore, the eye will roll in the optical orbit to compensate for slight tilts in head orientation. These changes cause inaccuracies in the computation of the viewing direction based on just the corneal center.

For this reason, the tabulated mapping of the corneal surface locations of the reflection points for the paired sources and sensors and the associated corneal radii are used to determine key corneal features. The tabulated corneal radii are first smoothed by averaging over adjacent reflection points determined by a clustering algorithm based upon the proximity of angular separations about the corneal center. The table of smoothed radii are then searched for clusters with minimum, maximum, and average values. While the central 30-degrees of the corneal anterior surface is spherical in shape, the basilar surface is slightly astigmatic with two principal meridians perpendicular to each other. The corneal horizontal radius of curvature (normally 7.98 mm) is roughly equal to that of the optical center; however, the vertical radius is less (7.60 mm). Therefore, routine 8 first isolates minimum radii points that are separated by more than 30-degrees to define the vertical meridian. The surface point midway between the two minimum radii points defines the optical surface center; the corneal radius is the distance between the corneal center and the optic surface center. Finally, routine 8 searches for radii points equal to corneal radius that are separated by more than 30-degrees to define the horizontal meridian.

The optical axis is defined by the corneal center and the optic surface center; routine 8 computes the center and directional cosines for the optical axis in the display coordinates from these values. The roll of the eye is then computed in routine 8 to complete the specification of the optical orientation. The vertical and horizontal meridians are used to compute an orthogonal set of coordinate axes perpendicular to the optical axis.

The result is an accurate description of the optical axes and center in the display coordinate system for each display refresh cycle. However, the visual axis extends from the first Gaussian nodal point of the eye (normally near the center of curvature of the corneal anterior surface) and is commonly perpendicular to the cornea; it is generally directed 5 degrees inwards to the optical axis and 2 to 3 degrees upward. The visual axis is defined by an origin point in the optical axes coordinate system and three directional cosines determined in an initial calibration process. These parameters defining the visual axis are transformed into coordinates for the display coordinate system in routine 8 from the relations for the optical axes. The result is an accurate specification of the visual axis.

In some video device 2 designs, the corneal mapping computations may inadvertently include the corneal peripheral when the eye is rotated to the side; in this case the computations may be in error due to incorrect centering on the cornea. Several checks on the mapping computations are made based on the expert knowledge of the cornea derived from the calibration process. First, the angular separations between the optic surface center and the reflection points for the maximum and minimum radii as measured from the corneal center should be fixed values normally greater than 15-degrees and less than 45-degrees. Further, the optic center corneal radius should agree with that derived in calibration.

However, a further embodiment of the invention uses the computation of the pupil center in the video device 2 coordinate system to center the corneal computations and as a check on the determination of the optical axis. In this design, the output of the opto-transistor array 3a is piped to a CCD video accumulator 5a during the display refresh cycle. The device accumulates an image of the eye with the reflected light from the excitation and decayed states of the refreshed light sources over the display refresh cycle. The accumulated image is downloaded to an image frame grabber at the end of the cycle output and then piped to an image processing board 5b where the centroid of the pupil image is computed using a binarization and image brightness threshold technique. The center 25 and major and minor axes of the centroid 23 in the accumulator's image plane 24 coordinates as shown in FIG. 3, are computed and stored in memory accessible by routine 8. Finally, the pupil diameter is computed from the pupil image centroid major and minor axes and the optical axes.

The pupil optical center is computed in routine 8 using a variation of an ophthalmometrical ray tracing technique for determining the position of internal surfaces of the eye. The tabulated listing 4a of sensor to light source pairings is searched for a sensor set 22 overlapping the apparent pupil image center 25. The light ray from the optical pupil center is transmitted through the eye and refracted to the image plane 24 of the accumulator 5a, from the cornea at the reflection point 21 for the display light sources 20 paired to the sensor set 22. The transmitted ray is coplanar to the incident and reflected light from the set of paired display sources to the corresponding sensors, and the refracted ray is parallel to the reflected light. The location of the reflection point 21 on the anterior surface of the cornea is computed from the tabulated source orientations 20 and sensor 22 positions and orientations. The directional cosines for the transmitted ray is computed from the corneal index of refraction and Snell's law relating the angle of incidence to the angle of refraction. In turn, the optical pupil center is computed from the prior computation of the corneal center and the distance between these centers. Finally, the optical axis is computed from the locations of these two centers. The result is the computed center and directional cosines for the optical axis of the eye in the video display 2a coordinate system as a check on the computations made from the corneal reflection point table.

The accuracy of these computations is dependent upon an initial calibration step in which the user gazes in turn at a series of cue markers displayed on the video display 2a. The data collected is used to solve for characteristics of the user's eye such as the corneal radius of curvature and the separation distance between the pupil center and corneal center. The relation of the viewing axis to the optical axes is determined by solving for the axis origin and the directional cosines in the optical axes coordinate system.

In some applications, the user may be viewing through the visor 37, an external real or virtual workspace which is independent of optical device 2; we may wish to know which elements of the visual workspace are being viewed. In this case, the visual line of sight computed by routine 8, must be transformed to that for the external workspace. This is accomplished by first locating the headset in the workspace. A tracking system 6 is used to measure the position and orientation of the headset 1 holding the video device 2. The tracking system consists of a source 6a, sensor 6b, and electronics processor 6c. The source is mounted in the user's workspace; the sensor is mounted on the headset. The system allows continual tracking of the six degrees of spatial freedom; the processing unit continually computes the position and orientation of the sensor relative to the source, and controls the transmission of the output data. Tracking systems are available employing different sources: infrared, ultrasonic, optical, and magnetic fields.

The computer routine 9 computes the user's viewing origin and direction in his visual workspace from the viewing point and axis given in the optical device 2 coordinates and the position and orientation of the headset as measured by the tracking system 6. The viewed point in the user's visual workspace is then computed using computer graphics concepts and a computer memory data base listing the objects and their locations in the user's workspace. The routine 9 computes the point of intersection of the viewing direction with each workspace surface facing the user from the surface normal and the location of a vertex. The routine checks to ensure that the intersection point is within the edges containing the surface. The viewed point is the contained intersection point closest to the user's eye.

The positions and orientations of the surfaces of the objects in the user's visual workspace are listed in a digital memory computer data file 9a by the directional cosines of their surfaces normals and the coordinates of the vertices. The surfaces of the objects are described by a piece-wise net of planar segments for computational purposes. Note that the objects being viewed for a virtual workspace are those generated by the drawing file for the display driver of video display 2a; in this case, the digital memory computer data file 9a is defined by the virtual workspace used to set up the display driver. Similarly, the position coordinates and directional cosines of the orientation of the tracking system source 6a in the workspace are listed in the computer memory data file.

The computer routine 10 performs as an expert system, classifying the immediate visual state defined by the workspace viewing origin and direction, as fixation, saccade, pursuit or blink from an embedded expert knowledge base of these ocular states. An understanding of the visual process is necessary to understand how the electronic expert system functions. Three sets of extraocular muscles control the movement and positioning of the eye. These muscle pairs include the horizontal and vertical rectus muscles, the lateral and medial rectus muscles, and the inferior and superior oblique muscles. Each pair of muscles exerts effort in a different axis, so that the eye is capable of movement to an extremely large number of positions. Some of the movements are involuntary and involve compensatory responses to movements of the head or to stimulation of certain facial nerves.

When studying a static visual display, the eye is continually rotating and fixating different portions of the scene; for this reason, the eye gaze consists of sudden saccadic jumps with interposed slightly jittery fixations. The saccadic jumps which move the eye between fixations are sudden and rapid ballistic movements lasting about 30 to 120 milliseconds and transversing 15 to 40 degrees. The peak velocity for a 10 degree saccade can reach 450 degrees per second; the peak velocity for a 20 degree saccade can range from 290 to 400 degrees per second. Vision is suppressed during a saccade. A 200 millisecond refractory period is required for recovery before another saccade can be executed.

The fixation following a saccade is a brief period of relative stability which allows that portion of the scene within the foveal vision to be studied. The fixation period is typically from 200 to 600 milliseconds. Small jittery motions occur during a fixation; these motions are composed of slight drifts with amplitudes less than one degree, followed by microsaccadic corrections. A low amplitude, high frequency tremor is superimposed. The purpose of a saccade is to rotate the eye so that the image of a cue in the visual scene falls within the foveal vision. The image is then studied during the fixation; the microsaccadic movements induce changes in the image required for seeing. However, the eye seldom remains in one fixation for long.

On the other hand, pursuit movements are slow involuntary eye tracking movements which smoothly follow a moving object of interest in the visual field. Pursuit movements have an initial reaction time of 0.12 to 0.25 seconds and are limited to a maximum velocity of 25 to 30 degrees per second. While the saccadic control system acts as a position servomechanism directing the fovea of the eye to a target, the pursuit system acts as a velocity servomechanism rotating the eye at the same angular rate as a target. Finally, blinks start slightly before or simultaneously with upward directed saccades, but never after the eye movement. In contrast, blinks are sometimes initiated after the onset of downward directed saccades. It has been reported that only in less than one percent of blinks is there apparent eye movement. Blinks usually last from 20 to 200 milliseconds with the longest observed terminating smoothly around 300 milliseconds.

The routine 10 detects saccades and predicts fixation end points, as well as separates saccades from pursuit eye tracking of moving targets, and eye blinks. The routine uses an automatic fixation and saccade classification scheme operated in conjunction with a saccadic end point predictor. The classification scheme is a combination of these two methods: the position variance method 10a and the velocity detection method 10b, operated as parallel processing channels. The end point predictor 10c is derived from a knowledge base on the relation between saccade peak velocity and amplitude of movement. The position variance method 10a is based on the expert knowledge that a fixation is characterized by relative immobility with low variance in eye movement, while a saccade is distinguished by rapid change (high variance) in position. In this method, the means and variances are computed for a sliding window of time samples in eye position. The variance of the windowed samples for a fixation is lower than an empirically determined threshold level. When a saccade occurs the variance rises, reaches a peak and then subsides toward the fixation level again. The initiation and termination of a saccade is automatically detected by comparing the position variance to the threshold level determined in an initial calibration process. Furthermore, curve fitting to the variance function is used to make predictions about the future variance values and therefore the time and location of the next fixation. The method has a time lag attributable to the width of the sampling window.

The velocity detection method 10b operates in parallel. In this method, the eye movement speed is computed from the windowed samples by first smoothing with a low-pass digital filter to remove noise, and then numerically differentiating the filter output. The computed speed is compared to an empirically determined threshold level separating saccadic movements from fixations. A speed above the threshold is classified as saccadic while that less than the threshold is classified as fixation. The position variance and velocity methods give similar results. These two methods are combined to obtain a more reliable saccade discriminator. The combined method can be based on either the agreement between the separate threshold outputs, or more elaborately, upon saccade state-probability estimates derived from the magnitudes of the position variance and speed measurements. The saccadic end point predictor 10c is activated once a saccade has been detected. This method predicting the end point of the saccadic movement from the peak velocity, discriminates between saccades and pursuit tracking. The predictor is based on the expert knowledge that the eye-movement velocity function during a saccade is nearly symmetrical about a peak velocity located approximately half-way to the next fixation. In detail, the saccadic velocity function rises above the threshold detection level, accelerates to a peak velocity about half-way to the next fixation, and then decelerates below the threshold at the fixation point. Although it has been reported in the literature that a sine wave is a good fit for the velocity function, the function is in fact, more or less symmetrical depending upon the magnitude of the peak velocity. In actuality, the saccadal amplitude is related to the maximum velocity by an exponential function using curve fitting constants. A look up table contains empirically determined correction factors needed to adjust for the asymmetry in the velocity function. The correction factors are derived in the calibration process. Therefore, the processor by detecting the peak of the saccadal velocity, uses the relation to the saccadal amplitude to predict the termination time and location of the next fixation. A classification as saccadal movement that does not satisfy the end point predictor is reclassified as pursuit movement; these movements are less than 30 degrees per second. Blinks correspond to cases where no reflection points are detected due to obscuration of the cornea by the eyelid.

The computer routine 11 groups the fixation data into task related visual gaze points. The user will tend to view a task related visual element with a sequence of fixations all in the same display area connected by small saccades. These fixations grouped together form a single gaze point of regard that more closely approximates the user's cognitive functioning. The routine uses a retrospective algorithm to determine the start, continuation, and termination of each gaze point as follows:

(1) A 100 millisecond sequence of eye fixations within 0.5 degrees of each other defines the start of a gaze point; the gaze point center is the mean of the eye fixations. The algorithm delay of 100 milliseconds is undetectable to the user.

(2) The gaze point is continued as long as eye fixations remain within one degree of the current gaze point center. The gaze dwell time is the sum of the 100 millisecond start time and the current continuation time.

(3) A 50 millisecond sequence of eye positions that are beyond one degree of the current gaze point defines the termination of the present gaze. A blink up to 200 milliseconds is allowed without termination.

The routine 11 computes the gaze point as the visual viewing point of the eye as computed by routine 9 for pursuit tracking; initially pursuit tracking will consist of a saccade to acquire the target on the fovea followed by steady tracking. A rate varying target will be tracked with saccadic updating in tracking rate.

The routine 12 computes the convergence points of the left and right eye gaze directions for a dual eyetracker configuration. The convergence points are the points of closest approach between the two gaze lines; the line segment connecting the two lines at these points is perpendicular to both lines.

Appendix A is a computer program written in C-language which implements the computations of routines 8, 9, 10, 11 and 12 for an optical device 2 as described above. The computer program uses the tabulated display source-to-sensor pairing table 4a produced from digital processor 4 and the pupil image processing from image processor 5b. The program computes the separate gaze points for each eye and the binocular convergence point for a dual eye system.

The computer program calls on the subroutine "Initial__values()" to read in the calibration values and supporting data tables on the display source and sensor arrays, and the workspace panels. The program next enters a loop where it waits for a pulse trigger 2d from the display field refresh clock of the optical device 2. Following the interrupt, the program first calls on "Get_time()" and then for each eye in turn loads the working files from "Load_tables()" and calls for computation of the gaze point from "Update_gaze()". The program then saves the computations for that eye in "Collect_gaze()". Following computation of the gaze point for each eye, the program computes the dual eye convergence point with "Converge()", and outputs the results to the host computer from "Output_gaze()". The program then returns to the start of the loop to wait for the next interrupt.

The computer program performs the gaze point computations of routine 8, called for from "Update_gaze()", in accordance with the following mathematical relations described by equations represented in vector dot (.) and cross (x) product notation, and scalar multiplication (*) and division (/) notation. Vectors are in upper case and scalars in lower case. Subroutine "Corneal_ctn()" acting as 8a, computes the location of the corneal center and the corneal radii for the reflection points from the source to sensor pairing table 4a. Let Pr[xr,yr,zr] represent the location in the display space 2a Cartesian coordinates of the corneal anterior surface reflection point 17 of the source 16 as detected by the sensor element 19 at the location Pe[xe,ye,ze]. Similarly, the directional cosines of the source 16 are represented by Ns[as,bs,cs], those of the ray 18 from the reflection point 17 to the sensor 19 are Ne[ae,be,ce], while Nr[ar,br,cr] are those of the corneal anterior surface normal for the radius, rc, originating from the anterior center Pc[xc,yc,zc] to the reflection point 17. The three equations relating the locations of the corneal center Pc and point 19 via point 17 are given in vector notation by:

$$Pr = Pc + rc*Nr = Pe + re*Ne,$$

where re is the distance between the points 17 and 19. Snell's law equating the ray's incidence and reflection angles about the surface normal Nr at point 17 gives the equation:

$$Nr.(Ne+Ns)=0,$$

Similarly, the law requiring that the incident and reflected rays be coplanar with the surface normal gives the equation:

$$Nr.(Ne \times Ns)=0.$$

Finally, the unity requirement on the surface normal gives the equation: $Nr.Nr=1$. The unknowns (Pc[xc,yc,zc], Pr[xr,yr,zr], rc, re) are solved for from a set of 18 equations with 18 unknowns for three source to sensor pairings 4a assuming that the corneal center location Pc is the same for all pairings. These equations have a unique solution given the display direction and that the user is looking at the display 2a.

The routine "Chk_pupil_ctn()" acting as 8b, computes the pupil center from the pairing table 4a and the pupil image center. Consider the corneal surface reflection point 21 mapping to the pupil image center 25. The ray from the pupil center which is refracted at this point to the CCD accumulator 5a, coincides with the ray reflected from source 20 to the sensor 22. The reflection angle, ar, is equal to the inverse cosine of the dot product of the unit vectors for the surface normal at point 21, Nr, and the reflected ray, Ne, $$ar = \arccos (Nr.Ne).$$

In turn, the refraction angle, at, is computed from Snell's law by $$at = \arcsin (\sin (ar)/index),$$

where index is the effective optical index of refraction. The directional cosines of the refracted ray unit vector, Nt[at,bt,ct], from the pupil center to point 21 are next determined from three equations. The dot product of the unit vectors for the refracted ray, Nt, and the point 21 surface normal, Nr, is equal to the cosine of the refraction angle, $$Nt.Nr = \cos (ar).$$

Furthermore, the unit vectors for the refracted ray, Nt, is coplanar with those for the incident ray, Ns, and reflected ray, Ne, at point 21, $$Nt.(Ne \times Ns)=0.$$

Finally, the refracted ray unit vector has unit length and the corresponding dot product equals unity, $$Nt.Nt=1.$$

The distance, rt, along the refracted ray, Nt, from the point 21 to the pupil center is computed. The pupil center is the intersection point of the ray with a sphere centered on the corneal center, Pc, and with radius, rp, the distance between the corneal center and the pupil center, a parameter derived in calibration. The distance rt is given by—

$$rt=rc*\cos{(at)}-sqrt(rp*rp-(rc*\sin{(at)})*(rc*\sin{(at)})),$$

where rc is the corneal radius at point 21. The pupil center, Pp[xp,yp,zp], is computed as—

$$Pp=Pr-rt*Nt.$$

The pupil center is used to compute the optical axis from the relation Pp=Pc+rp*No between the corneal center and the optical unit vector in accordance with 8c.

The subroutine "Cluster_pts()" acting as 8d, smoothes the corneal radii by a clustering algorithm performed with the dot product of the corneal surface normals Nr[ar,br,cr] for all reflection point combinations. The dot product is equal to the cosine of the angle between the unit vectors of the surface normals, and the corneal radii for product values larger than a critical value are averaged together for smoothing. That is, given reflection point i, the corneal radii of all other reflection points j such that $$Nri.Nrj > \text{critical\_value},$$

are averaged with the radius of reflection point i to form a smoothed value for point i.

The subroutine "Get_optical_axes()" acting as 8e, computes the optical axes system from the smoothed corneal radii. The optical surface center lies near the optical axis. The routine searches the table for a reflection point k with minimum distance $$dk=|Prk-Pc-rk*No|$$

from this line, where rk=|Prk-Pc|. The corneal radius for the optical center is rco=rc[k]. The routine next computes the vertical axis by searching the pairing table for the occurrence of two minimal radii surface points separated by more than 30-degrees, as measured by the dot product of the corresponding surface normals, to define the end points of the vertical meridian of the cornea. The points must be each more than 15-degrees from the optical axis. Letting i and j be two surface points such that the corresponding corneal radii—

$$rci, rcj < (rck, \text{all k not equal i,j}),$$

and the dot product of the corresponding surface normals is—

$$Nri.Nrj < \cos{(30\text{-degrees})},$$

while that of each point with the optical axis is—

$$Nri.No < \cos{(15\text{-degrees})},$$

then the vertical meridian is connected by the chord with unit vector Nz[az,bz,cz]—

$$Nz=(Prj-Pri)/dz,$$

where dz=|Pri-Prj| is the straight line distance between the points.

Finally, the horizontal meridian is defined by two surface points which each more than 15-degrees from the optical axis, are separated by 30-degrees and with corneal radii close in value to the optic center value. That is two points i and j such that |rci,j-rck|<acceptable_error, and the dot product of the corresponding surface normals, $$Nri.Nrj < \cos{(30\text{-degrees})}, \text{ and}$$

$$Nri.No < \cos{(15\text{-degrees})},$$

The unit vector of the horizontal axis is defined by, $$Ny=(Prj-Pri)/(|Prj-Pri|).$$

As a check on the computations, the optical coordinate system is orthogonal and the dot products of the corresponding unit vectors must be zero, i.e., Ny.Nz=0, No.Nz=0, and No.Ny=0. Furthermore, the optic center corneal radius, rck, must be close to the value derived in calibration, rco, that is, |rck-rco|<acceptable_error.

The subroutine "View_axis" acting as 8f, computes the origin and unit vector for the viewing axis in the display 2a coordinate system from the optical axes computations and known parameters derived in calibration. These parameters include the location of the viewing origin and the angular orientation of the viewing axis in the optical coordinate system. The viewing origin, Pv[xv,yv,zv] is located a fixed distance rx along the optical axis No, a distance ry along the horizontal axis Ny, and a distance rz along the vertical axis Nz. The viewing axis Nv[av,bv,cv] is orientated at a fixed elevation, ev, to the vertical axis and an azimuth, av, to the optical axis in the plane defined by the optical and horizontal axis. The viewing origin, Pv, is given by—

$$Pv=Pc+rx*No+ry*Ny+rz*Nz,$$

and the unit vector for the viewing direction by—

$$Nv=No*\sin{(ev)}*\sin{(av)}+Ny*\sin{(ev)}*\cos{(av)}+Nz*\cos{(ev)}.$$

These two parameters determine the viewing direction in the display coordinate system.

The viewed point in the work space coordinate system is computed by the subroutine "View_point()" in accordance with routine 9 described above. The subroutine translates the viewing position and direction in the optical device 2 coordinates to that in the workspace using the headset sensor 6 position and orientation returns. The display 2a coordinate system is centered on the sensor position and aligned with the corresponding axes by design. The sensor returns give the sensor location Ps and the azimuth, as, pitch, bs, and roll, cs, of the sensor in the workspace coordinate system. The sensor Cartesian coordinate system is centered at Ps with the orthogonal axes Ixs[axs,bxs,cxs], Iys[ays,bys,cys], and Izs[azs,bzs,czs] unit vectors, where the corresponding directional cosines are given for Ixs by—

$$axs=\cos{(as)}*\cos{(bs)},$$

$$bxs=\sin{(as)}*\cos{(bs)},$$

$$cxs=-\sin{(bs)},$$

for Iys by—

$ays=\cos(as)*\sin(bs)*\sin(cs)-\sin(as)*\sin(cs),$ $bys=\sin(as)*\sin(bs)*\sin(cs)+\cos(as)*\cos(cs),$ $cys=\cos(bs)*\sin(cs),$ and for Izs by—

$azs=\cos(as)*\sin(bs)*\cos(cs)+\sin(as)*\sin(cs),$ $bzs=\sin(as)*\sin(bs)*\cos(cs)-\cos(as)*\sin(cs),$ $czs=\cos(bs)*\sin(cs),$ in terms of the orientation angles. The viewing point Pe[xe, ye,ze] in the workspace is given by—

$Pe=Ps+xv*Ixs+yv*Iys+zv*Izs,$ and the viewing direction Ne[ase,bse,cse] is—

$Ne=av*Ixs+bv*Iys+cv*Izs.$

A planar surface is located in the workspace by an origin Po[xo,yo,zo] and a surface normal Ndz[az,bz,cz]. The surface faces the user if the dot product of the viewing direction and surface normal is less than zero, i.e., Ne.Ndz<0. The distance, rs, between the viewing point and the surface along the viewing direction is given by—

$rs=Ndz.(Pe-Po)/(Ndz.Ne),$ and the intersection point Pi with the surface is Pi=Pe+ rs*Ne. The surface contains a convex polygonal panel described by a set of vertices {xcor,ycor} in the surface coordinate system defined by the orthogonal unit vectors Ndx[ax,bx,cx] and Ndy[ay,by,cy]. The intersection point Pi is transformed into surface coordinates Pd[xd,yd] by—

$xd=scx*ri*(Ndx.Ndi),$ and $yd=scy*ri*(Ndy.Ndi),$ where ri is the distance between the surface origin, Po, and the intersection point, Pi, ri=|Pi−Po|, Ndi is the corresponding unit vector, Ndi=(Pi−Po)/ri, and scx and scy are the appropriate coordinate scaling factors. The routine checks that the intersection point is within the polygonal borders by computing the directional cosines of the unit vector between the point and each vertex, and then summing the angles formed between consecutive vertices from the inverse cosine of the dot product of the corresponding unit vectors. The angles will sum to 180-degrees for an enclosed point and zero-degrees for a point outside of the polygon. The polygon that has the shortest viewing distance is seen by the user.

The subroutine "Fixation()" classifies the viewing fixation in accordance with the routine 10 described above. The routine keeps a running record of the azimuth and elevation viewing angles and the corresponding angular velocities. The routine "Get_vel()" computes the present velocities from the position record using numerical differentiation following lowpass filtering to remove noise. The routine then computes the variance and velocity and classifies the viewing as fixation if these are less than thresholds. The viewing is classified pursuit if the variance exceeds the threshold but the velocity while greater than that for fixation is less than that for saccade. Finally, the routine classifies the viewing as saccade if the all thresholds are exceeded; the routine "Predict_endpt()" predicts the saccadic endpoint by fitting the velocity record to a half-sine wave represented by a second order polynomial.

Subroutine "Gaze_point()" reduces the fixation record to a gaze point in accordance with routine 11. The routine keeps a running record of the fixation azimuth and elevation viewing angles and the time between samples. The routine tests the record for the occurrence of a gaze point.

The subroutine "Converge()" computes the convergence points of the left and right eye gaze directions for the dual eyetracker configuration in accordance with routine 12. The convergence points are the points of closest approach between the two gaze lines; the line segment connecting the two lines at these points are perpendicular to both lines. Let this closest approach-line segment joins the left gaze line, with origin Pvl[xvl,yvl,zvl] and unit vector Nvl[avl,bvl,cvl], at the left convergence point Pcl[xcl,ycl,zcl]. The segment joins the right gaze line, with origin Pvr[xvr,yvr,zvr] and unit vector Nvr[avr,bvr,cvr], at the right convergence point Pcr[xcr,ycr,zcr]. Since the line segment is orthogonal to the gaze lines, the dot products of the corresponding unit vectors must be zero—

$Nvr.(Pcr-Pcl)=0,$ and $Nvl.(Pcr-Pcl)=0.$

The distances rl and rr from the gaze line origins to the corresponding convergence points are computed from—

$rl=(b*c-a)/(1-c*c),$ and $rr=(b-a*c)/(1-c*c),$ where a=Nvl.(Pvl−Pvr), b=Nvr.(Pvl−Pvr), and c=Nvl.Nvr. The corresponding convergence points are given by—

$Pcl=Pvl+rl*Nvl,$ and $Pcr=Pcr+rr*Nvr.$

The gaze convergence point is the average of these two points.

Appendix B is a computer program written in C-language which is used for calibration of the invention. The program computes the corneal radius of curvature, the origin and directional cosines of the viewing direction in the corneal optical axes system, and the separation between the pupil center and the corneal center. The invention is auto-calibrating since the user can quickly and accurately go through the calibration procedure which correlates eye gaze position with eye line of sight.

The program "Calibrate()" controls the calibration process and computes the appropriate constants from the user's viewing response data. The program calls for the sequential display of a series of cue markers from "Draw_target()" for the user to look at. As each cue is displayed the program waits for the user's response from "Hold_response()" and then collects the response data for that marker. The routine "Get_gaze" computes the corneal center and optical axes for each cue marker by calling on the appropriate routines found in the main program of Appendix A. The cue markers are placed in the visual scene so that the eye is in full view to the sensor array. This ensures that the optical axes may be derived from the source to sensor pairing table as described for subroutine "Calib_optical_axes" above without reference to the pupil image. The location Pt[xt,yt,zt] of the cue marker in the display coordinates is related to the viewing point, Pv, and direction, Nv, by—

$Pt=Pv+rt*Nv,$ where rt is the straight line distance between the two points. In turn, the viewing point, Pv, is located a fixed distance, rx, along the optical axis, No, a distance, ry, along the horizontal axis, Ny, and a distance, rz, along the vertical axis, Nz, and is given by—

$$Pv=Pc+rx*No+ry*Ny+rz*Nz.$$

The viewing axis, Nv, is orientated at a fixed elevation, ev, to the vertical axis and an azimuth, av, to the optical axis in the plane defined by the optical and horizontal axis and is given by—

$$Nv=No*\sin(ev)*\sin(av)+Ny*\sin(ev)*\cos(av)+Nz*\cos(ev),$$

The fixed distances rx, ry, and rz, and the fixed angles av and ev are unknowns which are computed in the calibration. These equations are combined to form—

$$Pt-Pc=a*No+b*Ny+c*Nz,$$

where—

$$a=rx+rt*\sin(ev)*\sin(av),$$

$$b=ry+rt*\sin(ev)*\cos(av),$$

$$c=rz+rt*\cos(ev).$$

The above expression form a set of three equations in the three unknown a, b, and c, for each cue marker presentation. In turn, the solution of the parameters a, b, and c for three cue markers enables the solution of the parameters rx, ry, rz, av, ev, as well as the three marker to view point distances, rt1, rt2, and rt3.

The distance rp between the corneal center and the pupil center is computed in the calibration process. The routine "Get_pupil_ctn()" searches the pairing table 4a for a source reflection point that overlaps the pupil image center. In a manner similar to that for the routine "Chk_pupil_ctn()", consider the corneal surface reflection point 21 which is mapping to the pupil image center 25. The ray from the pupil center which is refracted at this point to the CCD accumulator 5a, coincides with the ray reflected from source 20 to the sensor 22. The reflection angle, ar, is equal to the inverse cosine of the dot product of the unit vectors for the surface normal at point 21, Nr, and the reflected ray, Ne, $$ar=\arccos(Nr.Ne).$$

In turn, the refraction angle, at, is computed from Snell's law by $$at=\arcsin(\sin(ar)/index),$$

where index is the effective optical index of refraction. In turn, the angle ao at the corneal center between the optical axis and the surface normal is given by the inverse cosine of the dot product of the corresponding unit vectors—

$$ao=\arccos(Nr.No).$$

The corneal center, Pc, the surface reflection point 21, and the pupil center Pp (assumed to lie on the optical axis) form a triangle with adjacent sides rp and rc, the corneal radius for the point 21, with opposite angles, at, and pi–ao–at, respectively. The distance rp between the corneal center and the pupil center is therefore given by—

$$rp=rc*\sin(at)/\sin(pi-ao-at),$$

in accordance with the trigonometric law of sines.

The invention can be used with video display 2a that are not head mounted but rather mounted in the workspace separate from the user such as panel mounted displays. The display illuminates the user's eye as he views the task related display elements. For example, a near infrared light source array can be positioned within the field of view of the task centered displays. In addition, the sensor system 2b need not be head mounted; rather the sensor system could be mounted in the workspace separate from the user. In this case, the sensor system must be continually oriented toward the reflected light from the eye. For this reason, some sort of head sensor 6 either head mounted or separate from the user must be used to located the eye and align the light sensor array 2b.

FIG. 8 is a schematic showing the invention used to control computerized machinery from video displays. The user of the invention is viewing a visual display 41 which has task related elements 41a pertaining to the control of the computerized machinery 15. The user controls the machinery by gazing at the task related display element 41a which corresponds to the desired control action. The instant invention by design serves as a peripheral to the host computer system 13. The invention determines the display 41 location being gazed and transmits this information by output to the host computer 13. The host computer 13 compares the gazed location to those of the display elements 41a. Once a match is made, the host computer 13 executes the appropriate task related routines updating the state of the controlled machinery 15 and correspondingly, that of the visual display elements 41a as feedback to the user.

The visual display 41 may be either a real visual display seen through the display 2a visor, or an apparent image generated in virtual reality by the head mounted electronics display 2a or a combination of both with the virtual image overlaid on the real. In the latter case, the display driver for the electronic video display 2a is under the control of the host computer 13 to provide virtual reality or overlaid display elements 41a as control cues and task critical information.

When the visual display 41 is generated by the video display 2a, the number of pixels activated in a refresh cycle will vary with the visual display 41 as dictated by the host computer 13 in response to the state of the machinery 15 and the user's control selections. The entire display 2a will be activated for such uses as television camera returns, night vision goggles, and virtual reality displays used in computer graphics visual simulations. In these cases, all display pixels are used as light sources. On the other hand, so as not to interfere with the external scene, a limited number of line structures may be activated to display task critical information in virtual image, heads-up helmet mounted displays used in aircraft and helicopters. However, these line structures are drawn in predetermined patterns. Light filters are incorporated with the visor in heads-up displays to reduce display washout from ambient lighting from the external scene and the other electronic video displays located within the visual workspace. Furthermore, the intensity and radiant spectrum of the display's activation pattern are distinct characteristics readily processed by signal treatment. This is particularly true for the CRT driven phosphorous emitter displays. Finally, the video display 2a may show no discernible image to the user at all; instead the video display 2a may be a sequential series of near infrared light sources used merely to track the user's eye. In this case, the video display 2a is independent of the visual task display 41 and not under the control of the host computer 13. For example, the display 2a may be a LCD driven by a glow lamp through an infrared filter. Or the display 2a may be a matrix of near infrared LEDs. Finally, the display 2a may be a special design including task centered visually discernible elements combined with infrared sources.

The invention output to the host computer 13 in real time is: (1) the eye status flag, (2) the eye pupil size, (3) the gaze status flag, (4) the current gaze point location, (5) the gaze dwell time, (6) a task interest flag, and (7) the head position and orientation from the output of processor 9. The eye status flag is the output of routine 10: fixation, saccade, pursuit, or blink. The gaze status flag indicates either the start of a gaze, continuation, or termination. The gaze location gives the point of regard in both workspace coordinates and workspace surface by surface identifier and surface location. The routine has an initial 100 millisecond delay in detecting the start of a gaze and a 50 millisecond in detecting the end. The gaze dwell time is an indication of the user's cognitive task related interest in the visual element being studied. The dwell times tend statistically to be on the average longer for elements of interest. The task interest flag is reset to "non-interest" when the dwell time is less than a lower threshold value determined in calibration, usually about 150 milliseconds. However, the flag is set to "interest" when the dwell time exceeds an upper bound, usually about 250 milliseconds. The gaze status flag indicates a "saccade" during the large saccades that occur between gazes and "failure" when the processor fails to determine an eye position for more than 200 milliseconds. A further embodiment of the invention is the simultaneous tracking of both eyes with a dual display having a pair of video displays 2a and sensor system 2b. This allows the computation by computer routine 12 of the binocular convergence point in the user's three dimensional workspace for either real or virtual stereographic viewing. The convergence point is defined as the workspace point where the viewing axes are closest. In this case, the above output is made for both eyes separately along with the convergence point in the workspace coordinates.

The host computer 13 upon receiving a set task interest flag compares the gaze point location to those listed for the visual display elements 41. Once a match is made, the host computer 13 executes the appropriate task related routines updating the state of the controlled machinery and correspondingly, that of the visual display elements as feedback to the user. However, in some cases, the selected decision may have critical implications for the task performance. An example is that of engaging hostile fire upon another vehicle in warfare. Note that the relation of gaze dwell time to task elements is a statistical process that may vary under stress as the task conditions change. For this reason, in the event of critical tasks, the host computer 13 as an intermediate control step, will highlight the matched display element 41 with a change in color, brightness, or shape as feedback to the user. The appropriate control routines are then implemented if the user executes a manual action 14 in confirmation of the choice selection. The highlighting for element 41 is dropped if the confirmation 14 is not received within a preset time-out period, say several seconds. The manual confirmation action 14 may be a button push by the user or voice command via an automatic speech recognizer. Of course, the control routine executed along with the accompanying display update is determined by the display element 41 selected and the host computer 13 and associated display driver programs.

The accuracy of the eyetracker may be limited by the angular size of the human fovea (+/− 0.5 degree); the visual scene is integrated in the visual cortex as ocular fixations occur about the scene. However, the operator of a computer driven tactical display may wish to select among display icons of display elements 41 that are closer than this in size and perhaps even overlap. For this reason, a companion display to the tactical display may be shown by toggle switch selection, either adjacent to or as an overlap showing the icons in order of designation separated at 0.5 degree increments. The operator then looks at the companion display to make the selection.

The eye status and pupil size are passed to the host computer 13 for human factors analysis; the gaze point and duration are all that is needed for display element 41 selection. However, there is evidence that pupil dilation and eye blinks are related to information processing stages and user's workload. These are factors which are important in controlling the rate and form of display element presentation by the host computer 13. For example, it has been shown that the pupil will dilate at the start of information processing reaching its maximum just before decision, and contract at the moment of decision making. The extent of the dilation is an inverse function of the intelligence of the viewer and direct function of the complexity of the problem to be solved. However, the pupil change is also a function of extraneous factors including ambient lighting and subject fatigue. For these reasons pupil dilation is a valid measure of the stages of information processing only in constant illumination displays for alert users.

Furthermore, blinks are reported to occur at transitions between stages of information processing. In particular, blinks appear to mark brief breaks that the brain takes at the end of each phase of a mental task, and in this way punctuate the sequence of mental events involved in acquiring and processing information. The occurrence of eye blinks may punctuate the appropriate moments to measure pupil dilation in information processing. Another factor to consider is the level of workload which the user is experiencing. Eye blink rate has been shown to be non-linearity dependent on mental workload. Blink rate and duration are related to boredom, anxiety, and fatigue. Blink rate increases with boredom, anxiety, or other sources of physical or psychological stress. Fatigue increases blink duration. Attention to tasks demanding visual activity decreases the blink frequency. Head movements performed in conjunction with eye movements greater than 12-degrees, are an additional measure of workload. For example, workload information would be needed for the proper functioning of a host computer controlling the display formats for the user of an electronics intelligent pilot-vehicle interface design.

APPENDIX A: Applications computer program used to compute the workspace gaze point of both eyes and the binocular convergence point.

APPENDIX A

```
/* *********************************************

Computation of Gaze Point
                      from
        Display Emitting Source to Sensor Pairing Table
                      and
              Pupil Image Processing.

********************************************* */

/*   includes :                    */
/* -------------------             */
#include <stdio.h>
#include <conio.h>
#include <process.h>
#include <fcntl.h>
#include <sys\types.h>
#include <sys\stat.h>
#include <io.h>
#include <stdlib.h>
#include <atldefs.c>
#include <atlerrs.c>
#include <math.h>
#include <sys/timeb.h>
#include <time.h>

/* &&&&&&&&&&&&&&&&&&&&&&&&&&&&&&&&&&&&&&&&&&&& */

/* dual eye reference tables                            */

/* ############################################# */
/* -------------------- */
/* display source:         */
/* -------------------- */
float xoez[2],yoez[2],zoez[2]; /* source array center      */
float xesz[2], yesz[2];        /* element array spacing    */
int nexz[2],neyz[2];           /* row and column elements  */
float aexz[2],bexz[2],cexz[2]; /* row directional cosines  */
float aeyz[2],beyz[2],ceyz[2]; /* column directional cosines */
float aenz[2],benz[2],cenz[2]; /* normal directional cosines */
```

```
    float fezz[2];              /* focal length                 */
/* -------------------- */
/* sensor array:           */
/* -------------------- */
    float xosz[2],yosz[2],zosz[2]; /* sensor array center      */
    float xssz[2], yssz[2];     /* element array spacing       */
    int nsxz[2],nsyz[2];        /* row and column elements     */
    float asxz[2],bsxz[2],csxz[2]; /* row directional cosines  */
    float asyz[2],bsyz[2],csyz[2]; /* column directional cosines */
    float asnz[2],bsnz[2],csnz[2]; /* normal directional cosines */
    float fszz[2];              /* focal length                 */
/* -------------------- */
/* alignment display to sensor: */
/* -------------------- */
    float alxz[2],alyz[2],alzz[2]   /* directional cosines of display */
         ,blxz[2],blyz[2],blzz[2]   /* axes to sensor axes            */
         ,clxz[2],clyz[2],clzz[2];
/* -------------------- */
/* source to sensor pairing tables: */
/* -------------------- */
    long int ndataz[2];     /* pairings accumulated in display update */
    long int i_vertz[2][100],i_hortz[2][100];/* source display coors */
    long int i_rowz[2][100],i_colz[2][100];  /* sensor array coors   */
/* -------------------- */
/* image processing:      */
/* -------------------- */
    long int imagez[2]          /* image processing success flag     */
         ,i_ctnz[2],j_ctnz[2];  /* image processing pupil image center */
/* -------------------- */
/* calibration constants:  */
/* -------------------- */
    float indexz[2];            /* index of refraction               */
    float rcpz[2];              /* distance pupil to corneal ctns    */
    float rviewz[2][3];         /* distance view point to corneal ctn */
    float azvz[2],elvz[2];      /* view axis azimuth & elevation angles */
/* -------------------- */
/* viewing position and direction: */
/* -------------------- */
    float xvoz[2],yvoz[2],zvoz[2]; /* workspace viewing point        */
    float avoz[2],bvoz[2],cvoz[2]; /* viewing axis directional cosines */
    float alzez[2],elzez[2];    /* viewing azimuth and elevation     */
/* -------------------- */
/* viewed point:          */
```

```
/* -------------------- */
int idzz[2];                    /* workspace viewed surface    */ float ixdzz[2],iydzz[2]         /* viewed surface point        */
     ,rszz[2];                  /* eye distance to point       */
/* -------------------- */
/* viewing state:       */
/* -------------------- */
float var_fixate                /* threshold fixation angular variance */
     , vel_fixate       /*        fixation radial velocity    */
     , vel_pursuit;     /*        pursuit radial velocity     */
int nfix;                       /* fixation history file       */
float xfix;
float afxz[2][10],efxz[2][10];  /* azimuth & elevation angles  */
float vafz[2][10],vefz[2][10];  /* azimuth & elevation radial vels */
float velz[2][10];              /* readial velocity history file */
char eyestatez[2]               /* fixation state flag         */
    ,classifyz[2]               /* classification flag         */
    ,recordz[2];                /* prior classification        */
int startz[2]                   /* fixation state start counter */
   ,endz[2]                     /* saccadic end prediction     */
   ,blinkz[2];                  /* blink duration              */
/* -------------------- */
/* gaze state:          */
/* -------------------- */
int fixflagz[2];                /* gaze fixation state         */
float fixdwellz[2];             /* fixation dwell time         */
float agz[2][20],egz[2][20]     /* gaze azimuth & elevation history */
     ,tgz[2][20];               /* gaze time history           */
/* -------------------- */
/* covergence points :  */
/* -------------------- */
float xicz[2],yicz[2],zicz[2];  /* workspace convergence point */

/* &&&&&&&&&&&&&&&&&&&&&&&&&&&&&&&&&&&&&&&&&&&&&& */

/* workspace panels in workspace coordinates      */

/* ############################################## */
int npanels;                    /* workspace panels            */
float xo[10],yo[10],zo[10]      /* panel origin coordinates    */
     ,ax[10],bx[10],cx[10]      /* panel face axes             */
```

```
    ,ay[10],by[10],cy[10]      /* directional cosines         */
    ,az[10],bz[10],cz[10]      /* panel face normal dir cosines */
    ,scx[10],scy[10];          /* panel scale face to workspace */
int ncor[10];                  /* panel corners               */
float xcor[10][5],ycor[10][5]; /* face coordinates of corners */

/* &&&&&&&&&&&&&&&&&&&&&&&&&&&&&&&&&&&&&&&&&& */

/* working files                                             */

/* ########################################### */
long int ndata;   /* pairings accumulated in display update */
long int i_vert[100],i_hort[100]; /* source display coordinates */
float xe[100],ye[100],ze[100]    /* emitting source position & */
     ,ae[100],be[100],ce[100];   /* directional cosines        */
long int i_row[100],i_col[100];  /* sensor array coordinates   */
float xs[100],ys[100],zs[100]    /* sensor position &          */
     ,as[100],bs[100],cs[100];   /* directional cosines        */
float xr[100],yr[100],zr[100]    /* corneal reflection point pos */
     ,ar[100],br[100],cr[100];   /* & directional cosines      */
  float xco,yco,zco              /* corneal center coordinates & */
       ,rco,rc[100];             /*    reflection points radii */
int kc,nc[30];                   /* reflection point clusters  */
float xrv[30],yrv[30],zrv[30];   /* central reflection point   */
float arv[30],brv[30],crv[30];   /* central directional cosines */
float rav[30];                   /* smoothed corneal radii     */
float xoe,yoe,zoe;               /* source display center      */
float xes, yes;                  /* source display spacing     */
int nex,ney;                     /* vertical & horizontal elements */
float aex,bex,cex;               /*vertical directional cosines */
float aey,bey,cey;               /* horizontal directional cosines */
float aen,ben,cen;               /* surface normal directional cos */
float fez;                       /* focal length               */
float xos,yos,zos;               /* sensor array center        */
float xss, yss;                  /* element array spacing      */
int nsx,nsy;                     /* row and column elements    */
float asx,bsx,csx;               /* row directional cosines    */
float asy,bsy,csy;               /* column directional cosines */
float asn,bsn,csn;               /* normal directional cosines */
float fsz;                       /* focal length               */
long int image,i_ctn,j_ctn;      /* pupil image center         */
float xpctn,ypctn,zpctn;         /* pupil center coordinates   */
```

```
float index;              /* corneal index of refraction    */
float rcp;                /* distance pupil to corneal ctns */
float rview[3];           /* dist view point to corneal ctn */
float xpo,ypo,zpo;        /* pupil center coordinates       */
float xco,yco,zco;        /* corneal center coordinates     */
float aco,bco,cco;        /* optical axis direction cosines */
float acy,bcy,ccy;        /* horiz axis directional cosines */
float acz,bcz,ccz;        /* vert axis directional cosines  */
float xvo,yvo,zvo;        /* viewing point                  */
float avo,bvo,cvo;        /* viewing axis direction cosines */
float azv,elv;            /* view axis azimuth & elev angs  */
float alx,aly,alz
      ,blx,bly,blz        /* dispaly axes direction cosines */
      ,clx,cly,clz;       /* in sensor coordinate system    */
float alzt,elzt;          /* workspace head orient az &el   */
float alze,elze;          /* workspace viewing orientation  */
int idz;                  /* workspace panel in view        */
float ixdz,iydz,rsz;      /* viewing point and distance     */
float afx[10],efx[10];    /* azimuth & elevation angles     */
float vaf[10],vef[10];    /* azimuth & elevation radial vels*/
float vel[10];            /* radial velocity history        */
char eyestate,classify,record; /* fixation state and class flags */
int start,end,blink;      /* fixation start & end counters  */
int fixflag;              /* gaze state flag                */
float fixdwell;           /* gaze fixation duration         */
float ag[20],eg[20],tg[20]; /* gaze history                 */
float time0,dtime;        /* processor time                 */

/* $$$$$$$$$$$$$$$$$$$$$$$$$$$$$$$$$$$$$$$$$$$$$$$$$$$$$$$$$$ */

/* Main Program                                               */

/* ########################################################## */ main()

{
int ieye;        /* eye designator flag   */ initial_values();  /* read in calibration values */ repeat:
```

```
hold_trigger();      /* wait for processor 5 service call   */ get_time();          /* time between samples                */ for ( ieye = 0; ieye < 1; ieye++ ) {/* for each eye:        */ load_tables(ieye);   /* set up working files with eye files */ update_gaze();       /* perform real time gaze calulations  */ collect_gaze(ieye);  /* transfer working results to eye results */

} converge();          /* compute convergence point for both eyes */ output_gaze();       /* output gaze results to host computer    */ goto repeat;

}

/* &&&&&&&&&&&&&&&&&&&&&&&&&&&&&&&&&&&&&&&&&&&& */

/* Supporting Subroutines                                    */

/* ############################################# */ initial_values()

{ /* read in calibration values and workspace files */
/* display source:         */
extern float xoez[2],yoez[2],zoez[2]; /* source array center    */
extern float xesz[2], yesz[2];        /* element array spacing  */
extern int nexz[2],neyz[2];           /* row and column elements */
 extern float aexz[2],bexz[2],cexz[2]; /* row directional cosines */
extern float aeyz[2],beyz[2],ceyz[2]; /* column direction cosines */
extern float aenz[2],benz[2],cenz[2]; /* normal directional cosines */
extern float fezz[2];                 /* focal length           */
```

```
/* sensor array:          */
extern float xosz[2],yosz[2],zosz[2]; /* sensor array center    */
extern float xssz[2], yssz[2];        /* element array spacing   */
extern int nsxz[2],nsyz[2];           /* row and column elements */
extern float asxz[2],bsxz[2],csxz[2]; /* row directional cosines */
extern float asyz[2],bsyz[2],csyz[2]; /* column direction cosines */
extern float asnz[2],bsnz[2],csnz[2]; /* normal directional cosines */
extern float fszz[2];                 /* focal length           */
/* alignment display to sensor: */
extern float alxz[2],alyz[2],alzz[2]  /* display direction cosines */
         ,blxz[2],blyz[2],blzz[2]     /* axes to sensor axes    */
         ,clxz[2],clyz[2],clzz[2];
/* calibration constants:  */
extern float indexz[2];               /* index of refraction    */
extern float rcpz[2];                 /* distance pupil to corneal ctns */
extern float rviewz[2][3];            /* dist view point to corneal ctn */
extern float azvz[2],elvz[2];         /* view axis azimuth & elev angles */
/* viewing state:          */
extern float var_fixate               /* threshold fixation ang variance */
         , vel_fixate                 /* fixation radial velocity */
         , vel_pursuit;               /* pursuit radial velocity */
extern int nfix;                      /* fixation history file  */
extern float xfix;
extern float afxz[2][10],efxz[2][10]; /* azimuth & elevation angs */
extern float vafz[2][10],vefz[2][10]; /* azimuth & elev radial vels */
extern float velz[2][10];             /* radial velocity history file */
 extern char eyestatez[2]             /* fixation state flag    */
         ,classifyz[2]                /* classification flag    */
         ,recordz[2];                 /* prior classification   */
extern int startz[2]                  /* fixation start counter */
         ,endz[2]                     /* saccadic end prediction */
         ,blinkz[2];                  /* blink duration         */
/* gaze state:             */
extern int fixflagz[2];               /* gaze fixation state    */
extern float fixdwellz[2];            /* fixation dwell time    */
extern float agz[2][20],egz[2][20]    /* gaze az & elev history */
         ,tgz[2][20];                 /* gaze time history      */
/* workspace panels */
extern int npanels;                   /* workspace panels       */
extern float xo[10],yo[10],zo[10]     /* panel origin coordinates */
         ,ax[10],bx[10],cx[10]        /* panel axes direction cos */
         ,ay[10],by[10],cy[10]
```

```
                    ,az[10],bz[10],cz[10]    /* panel normal dir cosines */
                    ,scx[10],scy[10];         /* panel scale in workspace */
extern int    ncor[10];                        /* panel corners            */
extern float xcor[10][5],ycor[10][5];  /* face corner coords       */
extern float time0;                            /* processor time           */
int i,j,k,ie;
FILE *fopen(), *in;

/* pointer to timeb.h structure */
struct timeb timebuffer;

/* -------------------- */
/* display source:         */
/* -------------------- */
in=fopen("eydis.dat","r");
if(in != NULL) {
for ( ie = 0; ie < 2; ie++ ) {
fscanf(in,"%f\n %f\n %f\n",&xoez[ie],&yoez[ie],&zoez[ie]);
fscanf(in,"%f\n %f\n %d\n %d\n",
&xesz[ie],&yesz[ie],&nexz[ie],&neyz[ie]);
 fscanf(in,"%f\n %f\n %f\n %f\n %f\n %f\n %f\n %f\n %f\n",
&aexz[ie],&bexz[ie],&cexz[ie],
&aeyz[ie],&beyz[ie],&ceyz[ie],
&aenz[ie],&benz[ie],&cenz[ie]);
fscanf(in,"%f\n",&fezz[ie]); }
fclose(in);    }
else printf("cannot open file eydis.dat\n");

/* -------------------- */
/* sensor array:           */
/* -------------------- */
in=fopen("eysor.dat","r");
if(in != NULL) {
for ( ie = 0; ie < 2; ie++ ) {
fscanf(in,"%f\n %f\n %f\n",&xosz[ie],&yosz[ie],&zosz[ie]);
fscanf(in,"%f\n %f\n %d\n %d\n",
&xssz[ie],&yssz[ie],&nsxz[ie],&nsyz[ie]);
fscanf(in,"%f\n %f\n %f\n %f\n %f\n %f\n %f\n %f\n %f\n",
&asxz[ie],&bsxz[ie],&csxz[ie],
&asyz[ie],&bsyz[ie],&csyz[ie],
&asnz[ie],&bsnz[ie],&csnz[ie]);
fscanf(in,"%f\n",&fszz[ie]); }
fclose(in);    }
```

```
else printf("cannot open file eysor.dat\n");

/* -------------------- */
/* alignment of 3space sensor to display */
/* -------------------- */
in=fopen("eyms.dat","r");
if(in != NULL) {
for ( ie = 0; ie < 2; ie++ ) {
fscanf(in,"%f\n %f\n %f\n %f\n %f\n %f\n %f\n %f\n %f\n"
,&alxz[ie],&alyz[ie],&alzz[ie]
,&blxz[ie],&blyz[ie],&blzz[ie]
,&clxz[ie],&clyz[ie],&clzz[ie]); }
fclose(in);    }
else printf("cannot open file eyms.dat\n");

/* -------------------- */
/* calibration constants:    */
/* -------------------- */
in=fopen("eycal.dat","r");
if(in != NULL) {
for ( ie = 0; ie < 2; ie++ ) {
fscanf(in,"%f\n %f\n %f\n %f\n"
,&indexz[ie],&rcpz[ie],&azvz[ie],&elvz[ie]);
for ( i = 0; i < 3; i++ ) {
fscanf(in,"%f\n",&rviewz[ie][i]); }
} fclose(in); }
else printf("cannot open file eycal.dat\n");

/* -------------------- */
/* fixation and gaze     */
/* -------------------- */
in=fopen("eyfix.dat","r");
if(in != NULL) {
fscanf(in,"%f\n %f\n %f\n %d\n"
,&var_fixate,&vel_fixate,&vel_pursuit,&nfix);
fclose(in);    }
else printf("cannot open file eyfix.dat\n");
xfix=nfix;
for ( ie = 0; ie < 2; ie++ ) {
eyestatez[ie]=' '; classifyz[ie]=' '; recordz[ie]=' ';
startz[ie]=0; endz[ie]=0; blinkz[ie]=0;
for (i = 0;i < 10; i++ ) {
afxz[ie][i]=1.57; efxz[ie][i]=1.57;
```

```
vafz[ie][i]=0.; vefz[ie][i]=0.;velz[ie][i]=0.; }
fixflagz[ie]=0; fixdwellz[ie]=0.;
for (i = 0;i < 20; i++ ) {
agz[ie][i]=1.57; egz[ie][i]=1.57; tgz[ie][i]=0.; }
}

/* -------------------- */
/* workspace panels in 3space source coordinates */
/* -------------------- */
in=fopen("hpif.dat","r");
if(in != NULL) {
fscanf(in,"%d\n",&npanels);
for (k = 0;k < npanels; k++ ) {
fscanf(in,"%f\n %f\n %f\n %f\n %f\n %f\n %f\n %f\n %f\n %f\n %f\n"
,&xo[k],&yo[k],&zo[k]
,&ax[k],&bx[k],&cx[k]
,&ay[k],&by[k],&cy[k]
,&az[k],&bz[k],&cz[k]);
fscanf(in,"%f %f\n",&scx[k],&scy[k]);
fscanf(in,"%d\n",&ncor[k]);
for(j = 0;j < ncor[k];j++ ) {
fscanf(in,"%f %f\n",&xcor[k][j],&ycor[k][j]); } }
fclose(in); }
else printf("cannot open file hpif.dat\n");
scx[npanels+1]=1.0; scy[npanels+1]=1.0;

/* initialize time calls       */
tzset();

/* time between samples */
ftime(&timebuffer);
time0=timebuffer.time+timebuffer.millitm/1000.;

} get_time()

{/* get time in milliseconds between samples */
extern float time0,dtime;
double time;
```

```
struct timeb timebuffer;

ftime(&timebuffer);
time=timebuffer.time+timebuffer.millitm/1000.;
dtime=(time-timeo)*1000.;
time0=time;

} load_tables(ie)

int ie; /* ----- eye flag ----- */
{/* load working files from dual eye tables */
extern float xoez[2],yoez[2],zoez[2]; /* source array center      */
extern float xesz[2], yesz[2];        /* element array spacing    */
extern int nexz[2],neyz[2];           /* row and column elements  */
extern float aexz[2],bexz[2],cexz[2]; /* row directional cosines  */
extern float aeyz[2],beyz[2],ceyz[2]; /* column direction cosines */
extern float aenz[2],benz[2],cenz[2]; /* normal directional cosines */
extern float fezz[2];                 /* focal length             */ extern float xoe,yoe,zoe;             /* source display center    */
extern float xes, yes;                /* source display spacing   */
extern int nex,ney;                   /* vert and horiz elements  */
extern float aex,bex,cex;             /*vert directional cosines  */
extern float aey,bey,cey;             /* horiz directional cosines */
extern float aen,ben,cen;             /* normal direction cosines */
extern float fez;                     /* focal length             */
extern float xosz[2],yosz[2],zosz[2]; /* sensor array center      */
extern float xssz[2], yssz[2];        /* element array spacing    */
extern int nsxz[2],nsyz[2];           /* row and column elements  */
extern float asxz[2],bsxz[2],csxz[2]; /* row directional cosines  */
extern float asyz[2],bsyz[2],csyz[2]; /* column direction cosines */
extern float asnz[2],bsnz[2],csnz[2]; /* normal directional cosines */
extern float fszz[2];                 /* focal length             */
extern float xos,yos,zos;             /* sensor array center      */
extern float xss, yss;                /* element array spacing    */
extern int nsx,nsy;                   /* row & column elements    */
extern float asx,bsx,csx;             /* row directional cosines  */
extern float asy,bsy,csy;             /* column direct cosines    */
```

```
extern float asn,bsn,csn;            /* normal direction cosines  */
extern float fsz;                    /* focal length              */
extern float alxz[2],alyz[2],alzz[2] /* display direction cosines */
       ,blxz[2],blyz[2],blzz[2]      /* axes to sensor axes       */
       ,clxz[2],clyz[2],clzz[2];
extern float alx,aly,alz             /* display axes directional  */
       ,blx,bly,blz                  /* cosines in sensor         */
       ,clx,cly,clz;                 /* coordinate system         */
extern long int ndataz[2];           /* pairings accumulated display update */
extern long int i_vertz[2][100],i_hortz[2][100]; /* source display */
extern long int i_rowz[2][100],i_colz[2][100];   /* sensor array   */
extern long int i_vert[100],i_hort[100];  /* source display coords */
extern long int i_row[100],i_col[100];    /* sensor array coords   */
extern long int imagez[2]            /* image processing success  */
       ,i_ctnz[2],j_ctnz[2];         /* pupil image center        */
extern long int image,i_ctn,j_ctn;   /* image processing pupil ctr */
extern float indexz[2];              /* index of refraction       */
 extern float rcpz[2];               /* distance pupil to corneal ctns */
extern float rviewz[2][3];           /* dist view point to corneal ctn */
extern float azvz[2],elvz[2];        /* view axis azimuth & elev angles */
extern float index;                  /* distance pupil to corneal ctns */
extern float rcp;                    /* distance pupil to corneal ctns */
extern float rview[3];               /* dist view point to corneal ctn */
extern float azv,elv;                /* view axis azimuth & elev angles */
extern int nfix;                     /* fixation history file     */
extern float afxz[2][10],efxz[2][10]; /* azimuth & elevation angles */
extern float vafz[2][10],vefz[2][10]; /* az & elev radial velocities */
extern float velz[2][10];            /* redial velocity history file */
extern char eyestatez[2]             /* fixation state flag       */
       ,classifyz[2]                 /* classification flag       */
       ,recordz[2];                  /* prior classification      */
extern int startz[2]                 /* fixation start counter    */
       ,endz[2]                      /* saccadic end prediction   */
       ,blinkz[2];                   /* blink duration            */
extern float afx[10],efx[10];        /* azimuth & elev angles     */
extern float vaf[10],vef[10];        /* az & elev radial vels     */
extern float vel[10];                /* radial velocity history   */
extern char eyestate,classify,record; /* fixation state flags     */
extern int start,end,blink;          /* fixation start & end counters */
extern int fixflagz[2];              /* gaze fixation state       */
extern float fixdwellz[2];           /* fixation dwell time       */
extern float agz[2][20],egz[2][20]   /* gaze az & elev history    */
       ,tgz[2][20];                  /* gaze time history         */
```

```
extern int fixflag;              /* gaze state flag        */
extern float fixdwell;           /* gaze fixation duration */
extern float ag[20],eg[20],tg[20]; /* gaze history         */
int i;

/* source tables */
xoe=xoez[ie]; yoe=yoez[ie]; zoe=zoez[ie];
xes=xesz[ie]; yes=yesz[ie];
nex=nexz[ie]; ney=neyz[ie];
aex=aexz[ie]; bex=bexz[ie]; cex=cexz[ie];
aey=aeyz[ie]; bey=beyz[ie]; cey=ceyz[ie];
aen=aenz[ie]; ben=benz[ie]; cen=cenz[ie];
fez=fezz[ie];

/* sensor tables */
xos=xosz[ie]; yos=yosz[ie]; zos=zosz[ie];
xss=xssz[ie]; yss=yssz[ie];
nsx=nsxz[ie]; nsy=nsyz[ie];
asx=asxz[ie]; bsx=bsxz[ie]; csx=csxz[ie];
asy=asyz[ie]; bsy=bsyz[ie]; csy=csyz[ie];
asn=asnz[ie]; bsn=bsnz[ie]; csn=csnz[ie];
fsz=fszz[ie];

/* alignment display to sensor axes */
alx=alxz[ie]; aly=alyz[ie]; alz=alzz[ie];
blx=blxz[ie]; bly=blyz[ie]; blz=blzz[ie];
clx=clxz[ie]; cly=clyz[ie]; clz=clzz[ie];

/* pairing tables */
ndata=ndataz[ie];
for ( i = 0; i < ndata; i++ ) {
i_vert[i]=i_vertz[ie][i]; i_hort[i]=i_hortz[ie][i];
i_row[i]=i_rowz[ie][i]; i_col[i]=i_colz[ie][i];      }

/* image processing */
image=imagez[ie]; i_ctn=i_ctnz[ie]; j_ctn=j_ctnz[ie];

/* calibration constants: */
index=indexz[ie]; rcp=rcpz[ie];
azv=azvz[ie]; elv=elvz[ie];
for ( i = 0; i < 3; i++ ) {
  rview[i]=rviewz[ie][i]; }
```

```
/* viewing state:           */
eyestate=eyestatez[ie]; classify=classifyz[ie]; record=recordz[ie];
start=startz[ie]; end=endz[ie]; blink=blinkz[ie];
for ( i = 0; i < nfix; i++ ) {
afx[i]=afxz[ie][i]; efx[i]=efxz[ie][i];
vaf[i]=vafz[ie][i]; vef[i]=vefz[ie][i];
vel[i]=velz[ie][i];                         }

/* gaze state:              */
fixflag=fixflagz[ie]; fixdwell=fixdwellz[ie];
for ( i = 0; i < nfix; i++ ) {
ag[i]=agz[ie][i]; eg[i]=egz[ie][i];
tg[i]=tgz[ie][i];              }

} update_gaze()

{
/* >>>> update routine called by display refresh interrupt <<<< */ corneal_ctn();   /* corneal ctr from emitter to sensor pairing table */ cluster_pts();   /* cluster corneal reflection pts to smooth radii   */ chk_pupil_ctn(); /* pupil center from pairing table and image        */ get_optical_axes(); /* optical axes from pupil ctr & corneal radii */ view_point();        /* viewing point in viewing space            */ fixation();          /* fixation status of viewing                */ gaze_point();        /* reduce to gaze point                      */

}
``` corneal_ctn()

```
{ /* compute corneal center from display emitting source to sensor
     pairings                                           */
extern long int ndata;  /* pairings accumulated in display update */
extern long int i_vert[100],i_hort[100]; /* source display coord  */
extern float xe[100],ye[100],ze[100]    /* emitting source pos &  */
             ,ae[100],be[100],ce[100];  /* directional cosines    */
extern long int i_row[100],i_col[100];  /* sensor array coords    */
extern float xs[100],ys[100],zs[100]    /* sensor position &      */
             ,as[100],bs[100],cs[100];  /* directional cosines    */
extern float xr[100],yr[100],zr[100]    /* corneal reflection pt  */
             ,ar[100],br[100],cr[100];  /* directional cosines    */
extern float xco,yco,zco                /* corneal center coords & */
             ,rco,rc[100];              /* reflection points radii */
int i,j,k,k0,k1,k2,kk,nv;
float xc,yc,zc,rc0,rc1,rc2,rs0,rs1,rs2,xcount,az[10][10],bz[10],rz [10];

for ( i = 0; i < ndata; i++ ) {
  get_source(i_vert[i],i_hort[i],&xe[i],&ye[i],&ze[i]
                   ,&ae[i],&be[i],&ce[i]);
  get_sensor(i_row[i],i_col[i],&xs[i],&ys[i],&zs[i]
                   ,&as[i],&bs[i],&cs[i]);
  get_reflect(i,&ar[i],&br[i],&cr[i]);                  } xco=0.0; yco=0.0; zco=0.0; rco=0.0;
/* set up gaussian numerical solution              */
/* solve for each successive set of three pairings
     and average                                   */
for ( i = 0; i < ndata-2; i++ ) {
for (j = 0; j < 9; j++) { bz[j]=0.0;
for (k = 0; k < 9; k++) { az[j][k]=0.0; } }
k0=i; k1=k0+1; k2=k1+1;
az[0][0]=1.0; az[3][0]=1.0; az[6][0]=1.0; /* xc */
az[1][1]=1.0; az[4][1]=1.0; az[7][1]=1.0; /* yc */
az[2][2]=1.0; az[5][2]=1.0; az[8][2]=1.0; /* xz */
az[0][3]=  ar[k0]; az[1][3]=  br[k0]; az[2][3]=  cr[k0]; /* rc0 */
az[0][4]= -as[k0]; az[1][4]= -bs[k0]; az[2][4]= -cs[k0];
az[3][5]=  ar[k1]; az[4][5]=  br[k1]; az[5][5]=  cr[k1]; /* rc1 */
az[3][6]= -as[k1]; az[4][6]= -bs[k1]; az[5][6]= -cs[k1];
az[6][7]=  ar[k2]; az[7][7]=  br[k2]; az[8][7]=  cr[k2]; /* rc2 */
az[6][8]= -as[k2]; az[7][8]= -bs[k2]; az[8][8]= -cs[k2];
```

```
bz[0]=xs[k0]; bz[1]=ys[k0]; bz[2]=zs[k0];
bz[3]=xs[k1]; bz[4]=ys[k1]; bz[5]=zs[k1];
 bz[6]=xs[k2]; bz[7]=ys[k2]; bz[8]=zs[k2];
nv=9;
get_soln(nv,az,bz,rz);
xc=rz[0]; yc=rz[1]; zc=rz[2];
rc0=rz[3]; rs0=rz[4];
rc1=rz[5]; rs1=rz[6];
rc2=rz[7]; rs2=rz[8];
xco=xco+xc; yco=yco+yc; zco=zco+zc; rco=rco+rc0;
xr[i]=xc+rc0*ar[i];
yr[i]=yc+rc0*br[i];
zr[i]=zc+rc0*cr[i];
rc[k0]=rc0; }
rc[k1]=rc1; rc[k2]=rc2;
xcount = ndata-2;
xco=xco/xcount;
yco=yco/xcount;
zco=zco/xcount;
rco=rco/xcount;

} get_source(i,j,x,y,z,a,b,c)

long int i,j;
float *x,*y,*z,*a,*b,*c;
{/* get position & directional cosines for source display emitter */
extern float xoe,yoe,zoe; /* source display center         */
extern float xes, yes;    /* source display spacing        */
extern int nex,ney;       /* vertical and horizontal elements */
extern float aex,bex,cex; /*vertical directional cosines    */
extern float aey,bey,cey; /* horizontal directional cosines */
extern float aen,ben,cen; /* surface normal directional cosines */
extern float fez;         /* focal length                  */
float xi,yj,xf,yf,zf,rz;

xi=(i-nex/2)*xes;         /* source displacement from display ctn */
yj=(i-ney/2)*yes;
*x=xoe+xi*aex+yj*aey; /* position in reference coord system    */
```

```
*y=yoe+xi*bex+yj*bey;
*z=zoe+xi*cex+yj*cey;
xf=xoe+fez*aen;        /* position of focal point along display    */  yf=yoe+fez*ben;
 /* surface normal                 */
zf=zoe+fez*cen;
/* distance from focal point to source display element */
rz=sqrt((*x-xf)*(*x-xf)+(*y-yf)*(*y-yf)+(*z-zf)*(*z-zf));
*a=(*x-xf)/rz;  /* directional cosines of emitted ray from source */
*b=(*y-yf)/rz;
*c=(*z-zf)/rz;

} get_sensor(i,j,x,y,z,a,b,c)

long int i,j;
float *x,*y,*z,*a,*b,*c;
{/* get position and directional cosines for sensor array element */
extern float xos,yos,zos; /* sensor array center          */
extern float xss, yss;   /* element array spacing        */
extern int nsx,nsy;      /* row and column elements      */
extern float asx,bsx,csx; /* row directional cosines      */
extern float asy,bsy,csy; /* column directional cosines */
extern float asn,bsn,csn; /* normal directional cosines */
extern float fsz;        /* focal length                 */
float xi,yj,xf,yf,zf,rz;

xi=(i-nsx/2)*xss;  /* element displacement from array ctn */
yj=(i-nsy/2)*yss;
*x=xos+xi*asx+yj*asy;   /* position in reference system   */  *y=yos+xi*bsx+yj*bsy;
/* coordinate system         */
*z=zos+xi*csx+yj*csy;
xf=xos+fsz*asn;         /* position of focal point along  */  yf=yos+fsz*bsn;
/* array surface normal      */
zf=zos+fsz*csn;
/* distance from focal point to sensor array element */
rz=sqrt((*x-xf)*(*x-xf)+(*y-yf)*(*y-yf)+(*z-zf)*(*z-zf));
*a=(*x-xf)/rz;          /* directional cosines of reflected */
*b=(*y-yf)/rz;          /* ray to sensor                   */
*c=(*z-zf)/rz;
```

} get_reflect(i,a,b,c)

int i;
float *a,*b,*c;
{/* corneal reflection point surface normal directional cosines */
extern float ae[100],be[100],ce[100]; /* display source dir cos */
extern float as[100],bs[100],cs[100]; /* sensor element dir cos */
float a1,b1,c1,a2,b2,c2,aa1,aa2,aa,ab,ca;

a1=as[i]+ae[i];
b1=bs[i]+be[i];
c1=cs[i]+ce[i];
a2=bs[i]*ce[i]-be[i]*cs[i];
b2=cs[i]*ae[i]-ce[i]*as[i];
c2=as[i]*be[i]-ae[i]*bs[i];
aa1=(a1*c2-a2*c1)/(c1*b2-c2*b1);
aa2=(a1*b2-a2*b1)/(c1*b2-c2*b1);
aa= 1.0/sqrt(1.0+aa1*aa1+aa2*aa2);   /* eye viewing pos x-axis */
ba= -a*aa1;
ca= -a*aa2;
*a=aa;
*b=ba;
*c=ca;

} cluster_pts()

{/* cluster adjacent corneal reflection points, as
    measured by closeness of direction cosines, to
    smooth corneal radii over the anterior surface */
extern long int ndata;  /* pairings accumulated in display update */
extern float xr[100],yr[100],zr[100]; /* corneal reflection pnt    */ extern float
ar[100],br[100],cr[100]; /* & directional cosines    */
extern float rc[100];                    /* reflection points radii    */

```
extern int kc,nc[30];      /* number of reflection point clusters */
extern float xrv[30],yrv[30],zrv[30]; /* cluster central reflect pnt */ extern float
arv[30],brv[30],crv[30]; /* central direction cosines */      extern float rav[30];
/* smoothed corneal radius for cluster */
float test;
int igrp[100];
 int i,j;
static float test_limit = 0.996; /* clustering factor 5-degrees   */

/* initialize cluster groups counters    */
kc=0; for ( i = 0; i < ndata; i++ ) {igrp[i]=0; } for ( i = 0; i < ndata; i++ ) {
if( igrp[i] == 0 ) {
/* if point not assigned start cluster test */
kc=kc+1;
nc[kc]=1;
igrp[i] =kc;
rav[kc]=rc[i];
arv[kc]=ar[i]; brv[kc]=br[i]; crv[kc]=cr[i];
xrv[kc]=xr[i]; yrv[kc]=yr[i]; zrv[kc]=zr[i];
/* test for cluster of remaining points */
for ( j = i+1; j < ndata; j++ ) {
test=ar[i]*ar[j]+br[i]*br[j]+cr[i]*cr[j];
if( test > test_limit) {
/* add to cluster if close to starting point */
igrp[j]=kc; nc[kc]=nc[kc]+1;
rav[kc]=rav[kc]+rc[j];
arv[kc]=arv[kc]+ar[j];
brv[kc]=brv[kc]+br[j];
crv[kc]=crv[kc]+cr[j];
xrv[kc]=xrv[kc]+xr[j];
yrv[kc]=yrv[kc]+yr[j];
zrv[kc]=zrv[kc]+zr[j]; } }
/* cluster complete & average values */
rav[kc]=rav[kc]/nc[kc];
arv[kc]=arv[kc]/nc[kc];
brv[kc]=brv[kc]/nc[kc];
crv[kc]=crv[kc]/nc[kc];
xrv[kc]=xrv[kc]/nc[kc];
yrv[kc]=yrv[kc]/nc[kc];
zrv[kc]=zrv[kc]/nc[kc]; } }
```

} chk_pupil_ctn()

{/* compute pupil center from emitter pairing table and image processing */
/* check optical axis by corneal center to pupil center          */
extern long int image,i_ctn,j_ctn;   /* pupil image center          */
extern long int ndata;  /* pairings accumulated in display update */
extern long int i_row[100],i_col[100]; /* sensor array  coords    */
extern float ae[100],be[100],ce[100]; /* source directioncosines */
extern float as[100],bs[100],cs[100]; /* sensor direction cosines */
extern float ar[100],br[100],cr[100]; /* corneal direction cosines */
extern float rc[100];        /* corneal reflection points radii   */
extern float index;          /* corneal index of refraction       */
extern float rcp;            /* distance pupil to corneal ctns    */
extern float xpo,ypo,zpo;    /* pupil center coordinates          */
int i,ic;
float rchkx, rchkz;
float ako,bko,cko;
float rcos,angr,tsin,angt,tcos,at,bt,ct,rt;
float a1,a2,a3,dd,ddd,ddz,b1,b2,b3,b4,c2,aa1,aa2,chk;
/* upper bound for reflection point to pupil image center */
static float check = 20.0;
/* acceptable tolerance between optical axes          */
static float chk_axis = 0.996;  /* 5-degrees */
if(image == 0)return;   /* check for image processing success  */
/* pupil image isolated from ccd return & ctn computed         */

/* find sensor element closest to pupil ctn in pairing table   */
rchkz=10000.; ic=0;
for (i = 0; i < ndata; i++ ) {
rchkx=sqrt((i_ctn-i_row[i])*(i_ctn-i_row[i])
        + (j_ctn-i_col[i])*(j_ctn-i_col[i]));
if(rchkx < rchkz) {
rchkz=rchkx; ic=i; }       }
/* ensure sensor within range of pupil image center */
if(rchkz > check) return;
/* compute pupil ctr from reflection pnt coords & surface normal */
/* ..... angle of refraction :                                  */
rcos=ar[ic]*as[ic]+br[ic]*bs[ic]+cr[ic]*cs[ic];

```
angr=acos(rcos);        /* angle of reflection      */
tsin=sin(angr)/index;   /* refraction from Snell's law */
angt=asin(tsin);
tcos=cos(angt);
/* ..... refraction directional cosines :           */
a1=bs[i]*ce[i]-be[i]*cs[i];
a2=as[i]*ce[i]-ae[i]*cs[i];
 a3=as[i]*be[i]-ae[i]*bs[i];
dd=ar[ic]*b2-c2*br[ic];
b1= tcos*b2/dd;
b2= (ar[ic]*a2-a1*br[ic])/dd;
b3= -tcos*a3/dd;
b4= -(ar[ic]*a3-a1*cr[ic])/dd;
ddd=1.0+b2*b2+b4*b4;
aa1=(b1*b2+b3*b4)/ddd;
aa2=(b1*b1+b3*b3-1.0)/ddd;
ddz=sqrt(aa1*aa1-aa2);
at=aa1-ddz;
if(at < 0.0)at=aa1+ddz;   /* eye view in positive x-direction */
bt=b3-at*b4;
ct=b1-at*b2;
/* ..... distance from reflection point to pupil center :     */
rt=rc[ic]*tcos-sqrt(rcp*rcp-(rc[ic]*tsin)*(rc[ic]*tsin));
/*...... pupil center coordinates :                 */
xpo=xr[ic]-at*rt;
ypo=yr[ic]-bt*rt;
zpo=zr[ic]-ct*rt;

/* check optical axis */
ako=(xpo-xco)/rcp;
bko=(ypo-yco)/rcp;
cko=(zpo-zco)/rcp;
chk=aco*ako+bco*bko+cco*cko;
if(chk < chk_axis) {
aco=ako; bco=bko; cco=cko; }

} get_optical_axes()
```

```
{/* get optical axes from pupil center & smoothed corneal radii */
extern int kc;              /* number of reflection point clusters */
extern float arv[30],brv[30],crv[30]; /* central direction cosines */      extern float
xrv[30],yrv[30],zrv[30]; /* cluster central reflect pnt */
extern float rav[30];       /* smoothed corneal radius for cluster */
extern float rco;           /* optic center corneal radius        */
extern float xco,yco,zco; /* corneal center coordinates           */
extern float aco,bco,cco; /* optical axis directional cosines     */
extern float acy,bcy,ccy; /* horizontal axis directional cosines  */
 extern float acz,bcz,ccz; /* vertical axis directional cosines   */
float xm,ym,zm,am,bm,cm,rm,dm,rk,dk,rz,acz,bcz,ccz,test,rcmin;
int i,ic,ik,im;
static float test_val = 0.8660; /* cosine 30-degrees */
static float test_val2= 0.9659; /* cosine 15-degrees */
static float tol = 0.01;        /* tolerance in radii difference */

/* find optic center point from optical axis */
dm=10000.; im=0;
for ( i = 0; i < kc; i++ ) {
rk=(xrv[i]-xco)*aco+(yrv[i]-yco)*bco+(zrv[i]-zco)*cco;
dk=sqrt((xrv[i]-xco-rk*aco)*(xrv[i]-xco-rk*aco)
       +(yrv[i]-yco-rk*bco)*(yrv[i]-yco-rk*bco)
       +(zrv[i]-zco-rk*cco)*(zrv[i]-zco-rk*cco));
if(dk < dm) { dm=dk; im=i; } }
rco=rav[im];

/* vertical axis */
/* find minimum radius point 15-degrees separation from center */
rcmin=10000.; ic=0;
for ( i = 0; i < kc; i++ ) {
if(rcmin > rav[i] ) {
test=acco*arv[i]+bco*brv[i]+cco*crv[i];
if(test < test_val2) {ic=i; } } }

/* find minimum radius point 30-degrees separation */
rcmin=10000.; ik=0;
for ( i = 0; i < kc; i++ ) {
if(i != ic) {
if(rcmin > rav[i] ) {
test=arv[ic]*arv[i]+brv[ic]*brv[i]+crv[ic]*crv[i];
if(test < test_val) { ik=i; } } } }

/* compute vertical axis */
```

```
rz=sqrt((xrv[ic]-xrv[ik])*(xrv[ic]-xrv[ik])
    +(yrv[ic]-yrv[ik])*(yrv[ic]-yrv[ik])
    +(zrv[ic]-zrv[ik])*(zrv[ic]-zrvik]));
acz=(xrv[ic]-xrv[ik])/rz;
bcz=(yrv[ic]-yrv[ik])/rz;
ccz=(zrv[ic]-zrv[ik])/rz;
if(zrv[ic] < zco)        /* check orientation                    */
{ acz= -acz; bcz= -bcz; ccz= -ccz; }

/* horizontal axis */
/* find radius point 15-degrees separation from center */
ic=0;
for ( i = 0; i < kc; i++ ) {
if(sqrt((rco-rav[i])*(rco-rav[i])) < tol) {
test=aco*arv[i]+bco*brv[i]+cco*crv[i];
if(test < test_val2) {ic=i; } } }

/* find radius point 30-degrees separation */
ik=0;
for ( i = 0; i < kc; i++ ) {
if(i != ic) {
if(sqrt((rco-rav[i])*(rco-rav[i])) < tol) {
test=arv[ic]*arv[i]+brv[ic]*brv[i]+crv[ic]*crv[i];
if(test < test_val) { ik=i; } } } }

/* compute horizontal axis */
rz=sqrt((xrv[ic]-xrv[ik])*(xrv[ic]-xrv[ik])
    +(yrv[ic]-yrv[ik])*(yrv[ic]-yrv[ik])
    +(zrv[ic]-zrv[ik])*(zrv[ic]-zrvik]));
acy=(xrv[ic]-xrv[ik])/rz;
bcy=(yrv[ic]-yrv[ik])/rz;
ccy=(zrv[ic]-zrv[ik])/rz;
if(yrv[ic] < yco)        /* check orientation                    */
{ acy= -acy; bcy= -bcy; ccy= -ccy; }

} view_axis()

{/* compute viewing direction from optical axis and roll axes    */
```

```
extern float xco,yco,zco;   /* corneal center coordinates       */
extern float aco,bco,cco;   /* optical axis directional cosines */
extern float acy,bcy,ccy;   /* horizontal axis directional cosines */
extern float acz,bcz,ccz;   /* vertical axis directional cosines */
extern float rview[3];      /* distance view point to corneal ctn */
extern float xvo,yvo,zvo;   /* viewing point                    */
extern float avo,bvo,cvo;   /* viewing axis directional cosines */
extern float azv,elv;       /* view axis azimuth & elevation angles */
float av,bv,cv;             /* from optical axes                */

/* viewing origin :    */
xvo=xco+rview[0]*aco+rview[1]*acy+rview[2]*acz;
yvo=yco+rview[0]*bco+rview[1]*bcy+rview[2]*bcz;
zvo=zco+rview[0]*cco+rview[1]*ccy+rview[2]*ccz;

/* viewing direction : */
av=cos(elv)*cos(azv);
bv=cos(elv)*sin(azv);
av=sin(elv);
avo=av*aco+bv*acy+cv*acz;
bvo=av*bco+bv*bcy+cv*bcz;
cvo=av*cco+bv*ccy+cv*ccz;

} view_point()

{/* viewing point in viewing space        */
/* viewing point in head supported system */
extern float xvo,yvo,zvo;  /* viewing point                    */
extern float avo,bvo,cvo;  /* viewing axis directional cosines */
/* workspace panels in workspace coordinates */
extern int npanels;        /* workspace panels                 */
extern float xo[10],yo[10],zo[10] /* panel origin coordinates  */
            ,ax[10],bx[10],cx[10] /* panel axes direction cosines */
            ,ay[10],by[10],cy[10]
            ,az[10],bz[10],cz[10] /* panel normal dir cosines  */
            ,scx[10],scy[10];     /* panel scaling to workspace */
extern int   ncor[10];            /* panel corners             */
extern float xcor[10][5],ycor[10][5]; /* panel corners coordinates */
```

```
extern float alzt,elzt;    /* workspace head orientation az &el  */
extern float alze,elze;    /* workspace viewing orientation       */
extern int idz;            /* workspace panel in view             */
extern float ixdz,iydz,rsz; /* viewing point and distance         */
extern float alx,aly,alz
             ,blx,bly,blz
             ,clx,cly,clz;
float xs,ys,zs,as,bs,cs;   /* sensor workspace position and angles */
float cosaz,sinaz,cosbz,sinbz,coscz,sincz;
float axsz,bxsz,cxsz       /* sensor workspace directional cosines */
      ,aysz,bysz,cysz
      ,azsz,bzsz,czsz;
float xe,ye,ze;            /* viewing point workspace coordinates  */
 float ase,bse,cse;         /* viewing direction directional cosines */
int ip,j,k,ik,it;
float ah,bh,ch,qs,rs,xi,yi,zi,ri,hk,ai,bi,ci;
float xd,yd,angchk,d0,a0,b0,a00,b00,d1,a1,b1,rchk;
float xdz[10],ydz[10],rdz[10];
int ipz[10];
static float pi=3.14159;

/* workspace head supported system position and orientation : */
get_hpi(&xs,&ys,&zs,&as,&bs,&cs);

/* convert viewing coordinates to workspace coordinates */
cosaz=cos(as);
sinaz=sin(as);
cosbz=cos(bs);
sinbz=sin(bs);
coscz=cos(cs);
sincz=sin(cs);

/* system sensor x-axis in workspace */
axsz=cosaz*cosbz;
bxsz=sinaz*cosbz;
cxsz=-sinbz;
/* system sensor y-axis in workspace */
aysz=cosaz*sinbz*sincz-sinaz*coscz;
bysz=sinaz*sinbz*sincz+cosaz*coscz;
cysz=cosbz*sincz;
/* system sensor z-axis in workspace */
azsz=cosaz*sinbz*coscz+sinaz*sincz;
bzsz=sinaz*sinbz*coscz-cosaz*sincz;
```

```
czsz=cosbz*coscz;

/* workspace position of viewing eye */
xe=xs+xvo*axsz+yvo*aysz+zvo*azsz;
ye=ys+xvo*bxsz+yvo*bysz+zvo*bzsz;
ze=zs+xvo*cxsz+yvo*cysz+zvo*czsz;

/* workspace head track direction */
ah=alx*axsz+aly*aysz+alz*azsz;
bh=alx*bxsz+aly*bysz+alz*bzsz;
ch=alx*cxsz+aly*cysz+alz*czsz;
alzt=atan2(ah,bh); elzt=acos(ch);

/* workspace viewing direction */
ase=(alx*axsz+aly*aysz+alz*azsz)*avo
   +(blx*axsz+bly*aysz+blz*azsz)*bvo
   +(clx*axsz+cly*aysz+clz*azsz)*cvo;
bse=(alx*bxsz+aly*bysz+alz*bzsz)*avo
   +(blx*bxsz+bly*bysz+blz*bzsz)*bvo
   +(clx*bxsz+cly*bysz+clz*bzsz)*cvo;
cse=(alx*cxsz+aly*cysz+alz*czsz)*avo
   +(blx*cxsz+bly*cysz+blz*czsz)*bvo
   +(clx*cxsz+cly*cysz+clz*czsz)*cvo;
 alze=atan2(ase,bse); elze=acos(cse);

/* view intersection point with workspace surfaces */
ip=0;
for (k = 0;k < npanels;k++ )
{  chk=ase*az[k]+bse*bz[k]+cse*cz[k];
  if(chk < 0.0) { /* panel faces observer       */
/*     distance to intersection point        */
  qs=az[k]*ase+bz[k]*bse+cz[k]*cse;
  rs=az[k]*(xo[k]-xe)+bz[k]*(yo[k]-ye)+cz[k]*(zo[k]-ze);
  if(qs == 0.)qs=1.0; rs=rs/qs;
  /* directional cosines to intersection point
     from observer                      */
  xi=rs*ase; yi=rs*bse; zi=rs*cse;
  /* difference between coordinates of intersection point
     on display surface and display origin     */
   xi=xi+xe-xo[k]; yi=yi+ye-yo[k]; zi=zi+ze-zo[k];
   /* distance from display origin to intersection point */
   ri=sqrt(xi*xi+yi*yi+zi*zi); if(ri < 0.01)ri=1.0;
   /* and directional cosines in viewing 3space
```

```
            coordinates                      */
       ai=xi/ri; bi=yi/ri; ci=zi/ri;
       /* intersection point in display screen coordinates */
       xd=ri*(ax[k]*ai+bx[k]*bi+cx[k]*ci);
       yd=ri*(ay[k]*ai+by[k]*bi+cy[k]*ci);
       /* convert display point from cms to rasters    */
       xd=xd*scx[k]; yd=yd*scy[k];
       /* check that intersection point within panel bounds */
       angchk=0.;
       d0=sqrt((xd-xcor[k][0])*(xd-xcor[k][0])
           +(yd-ycor[k][0])*(yd-ycor[k][0]));
       a0=(xcor[k][0]-xd)/d0; b0=(ycor[k][0]-yd)/d0;
       a00=a0; b00=b0;
       for (j = 1;j < ncor[k];j++ ) {
       d1=sqrt((xd-xcor[k][j])*(xd-xcor[k][j])
           +(yd-ycor[k][j])*(yd-ycor[k][j]));
       a1=(xcor[k][j]-xd)/d1; b1=(ycor[k][j]-yd)/d1;
       angchk=angchk+acos(a0*a1+b0*b1);
       a0=a1; b0=b1;             }
       a1=a00;b1=b00;
       angchk=angchk+acos(a0*a1+b0*b1);
       if(angchk >= (2.*pi-.01)) {
       /* inside point */
       xdz[ip]=xd;
       ydz[ip]=yd;
       rdz[ip]=rs;
       ipz[ip]=k;
       ip=ip+1;         }
    }
    }
    /* find closest panel                    */
    if(ip == 0)goto nopanel;
    rchk=rdz[0]; it=0;
     for(ik = 0;ik < ip;ik++ ) {
      if(rchk > rdz[ik])  {
      rchk=rdz[ik]; it=ik; }  }
    ixdz=xdz[it];
    iydz=ydz[it];
    rsz=rdz[it];
    idz=ipz[it];
     return;

nopanel:
```

```
/* no panel found and return default values        */
ixdz=999.9; iydz=999.9; rsz=999.9; idz=99;

} get_hpi(xs,ys,zs,as,bs,cs)

float *xs,*ys,*zs,*as,*bs,*cs;
{/* retrive head position and azimuth, pitch, & roll orientation */

/* particular to 3space tracking system */

} fixation()

{/* classify fixation status of viewing update */
extern long int image;   /* image processing success          */
extern float alze,elze;  /* workspace viewing orientation     */
extern int nfix;         /* fixation history file             */
extern float xfix;
extern float afx[10],efx[10];  /* azimuth & elevation angle   */
extern float vaf[10],vef[10];  /* azimuth & elevation velocities */
extern float vel[10];
extern float var_fixate   /* thresholds                       */
         , vel_fixate
         , vel_pursuit;
extern char eyestate,classify,record;
extern int start,end,blink;
float anz, anq, enz, enq, var,vmax;
int i;

/* compute angular velocity and update history files */
 for ( i = 0; i < nfix; i++ ) {
afx[nfix-i]=afx[nfix-1-i];
efx[nfix-i]=efx[nfix-1-i];
vaf[nfix-i]=vaf[nfix-1-i];
```

```
vef[nfix-i]=vef[nfix-1-i];
vel[nfix-i]=vel[nfix-1-i]; }
afx[0]=alze; efx[0]=elze;
get_vel(&vaf[0],nfix,afx);
get_vel(&vef[0],nfix,efx);

/* check for lost image */
if(image == 0){ /* lost image */
afx[0]=afx[1];   /* retain previous values */
efx[0]=efx[1];
vel[0]=vel[1];
start=start+1;
classify ='b';  /* blink */
if(record != classify)
{record=classify;
blink=0;
return;        }
blink=blink+1;
return;         }

/* check for saccade   */
/* .... variance method */
anz=0.; anq=0.; enz=0.; enq=0.;
for ( i = 0; i < nfix; i++ ) {
anz=anz+afx[i];
anq=anq+afx[i]*afx[i];
enz=enz+efx[i];
enq=enq+efx[i]*efx[i];      }
var=sqrt((anq-anz*anz/xfix)
        +(enq-enz*enz/xfix));

/* .... velocity method */
vel[0]=sqrt(vaf[0]*vaf[0]+vef[0]*vef[0]);

/* classify */
if(var< var_fixate && vel[0] < vel_fixate)
{/* fixation */
classify = 'f';
if(record != classify)
{record = classify; }
if(eyestate != classify)
{eyestate=classify;
start=0;
```

```
return;            }
start=start+1;
return;            } if(vel[0] < vel_pursuit)
{/* pursuit */
classify = 'p';
if(record != classify)
 {record = classify;  }
if(eyestate != classify)
{eyestate=classify;
start=0;
return;            }
start=start+1;
return;            }

/* saccade  */
classify = 's';
if(record != classify)
{record = classify;  }
if(eyestate != classify)
{eyestate=classify;
start=0;
return;            }
start=start+1;
predict_endpt(vel,&vmax,start,&end);
if(start > end)
{classify = 'pt';
if(record != classify)
{record = classify;  }
if(eyestate != classify)
{eyestate=classify;
start=end+1;
return;            }
}

} get_vel(vf,nf,fx)
```

```
int nf;
float fx[10],*vf;
{/* compute velocity from position history
    using numerical differentiation techniques
    5-pt formula fixed interval interpolation */
float sm[10]; /* smoothed values */
int i;
static int lowpass = 2; float smooth = 2.;
static float factor  = 12.0*.010; /* 100 Hz sampling frequency */

/* lowpass filter to remove noise */
for ( i = 0; i < nf-lowpass+1; i++ ) {
sm[i] =(fx[i]+fx[i+1])/smooth;    }   /* moving average */

/* numerical differentiation */
*vf = ( -25.*sm[0]
       + 48.*sm[1]
       -36.*sm[2]
       +16.*sm[3]
       - 3.*sm[4] )/factor;

} predict_endpt(vel,vmax,start,end)

float vel[10],*vmax;
int start,*end;
{/* predict saccade end point from velocity record */
float ar[10][10],br[10],a1,a2,a3;
int i;

/* .... curve fit 2nd order polynomial to positive half sine wave
        p[0:1] = -4.12251*x[0:1]*x[0:1]+4.12251*x[0:1]-.050465 */
for ( i = 0; i < start; i++ ) {
ar[0][i]=1.0;
ar[1][i]= -0.050465;
ar[2][i]= 4.12251*i;
ar[3][i]= -vel[start-1-i];
br[i]=    8.24502*i*i;      }
regress_analy(start,ar,br,&a1,&a2,&a3);
```

```
/* .... max vel */
*vmax=a1/a3;

/* .... end point */
*end=a2;

} regress_analy(nr,ar,br,a1,a2,a3)

int nr;
float ar[10][10],br[10],*a1,*a2,*a3;
{/* set up regression analysis
        for gaussian solution */
float am[10][10],bm[10],rz[10];
int i,j,k;
static int mz=4;

for ( i = 0; i <= mz; i++ ) {
for ( j = 0; j <= mz; j++ ) {
am[i][j]=0.0; } } for ( i = 0; i <= mz; i++ ) {
for ( j = 0; j <= mz; j++ ) {
for ( k = 0; k < nr; k++ ) {
 am[i][j]=am[i][j]+ar[i][k]*ar[j][k]; } } } for ( i = 0; i <= mz; i++ ) {
bm[i]=0.0;
for ( k = 0; k < nr; k++ ) {
bm[i]=bm[i]+br[k]*ar[i][k]; } } get_soln(mz,am,bm,bz);

*a1=bz[1];
*a2=bz[2];
*a3=bz[3];

}
```

```
get_soln(m,am,bm,bs)

double am[10][10],bm[10],bs[10];
int m;
{/* gaussian elimination and backwards substitution
     for solution of linear system of equations     */
double a[10][10],b[10],x[10];
int i,j;

for ( i = 0;i <= m; i++ ) {
b[i+1]=bm[i];
for ( j = 0;j <= m; j++ ) {
a[i+1][j+1]=am[i][j]; } } find_dce(m+1,a,b,x);

for (i = 0;i <= m; i++ ) {
bs[i]=x[i+1]; }

} find_dce(n,a,b,x)

double a[10][10],b[10],x[10];
int n;
{ /* gaussian elimination with
       backward substitution */
double ab[11][11],xm[11][11],as;
int ic[11];
int nm,i,j,jp,k,i1,n1,ij,ij1;
/* form augmented matrix from
   system matrix and inhomogeneous
   vector                    */
nm=n+1;
for (i = 1;i <= n; i++ ) {
for (j = 1;j <= n; j++ ) {
ab[i][j]=a[i][j]; } }
for (i = 1;i <= n; i++ ) {
```

```
ab[i][nm]=b[i]; }

/* start elimination process */
n1=n-1;
for (i = 1;i <= n1; i++ ) {
for (jp = i;jp <= n; jp++ ) {
if(ab[jp][i] != 0.0)goto label3; }
singular_err();
label3: ;
ic[i]=jp;
if(jp == i)goto label5;
for (j = 1;j <= nm; j++ ) {
as=ab[jp][j];
ab[jp][j]=ab[i][j];
ab[i][j]=as; }
label5: ;
i1=i+1;
for (j = i1;j <= n; j++ ) {
xm[j][i]=ab[j][i]/ab[i][i];
for (k = 1;k <= nm; k++ ) {
ab[j][k]=ab[j][k]-xm[j][i]*ab[i][k]; } }
}

/* start backward substitution */
if(ab[n][n] == 0.0)singular_err();
x[n]=ab[n][nm]/ab[n][n];
for (i = 1;i <= n1; i++ ) {
ij=n-i;
x[ij]=ab[ij][nm];
ij1=ij+1;
for (j = ij1;j <= n; j++ ) {
x[ij]=x[ij]-ab[ij][j]*x[j]; }
x[ij]=x[ij]/ab[ij][ij];    }

} singular_err()

{ /* singualr matrix */
printf("singular matrix\n");
``` exit();

} gaze_point()

```
{/* reduce fixation record to gaze point */
extern float dtime;
extern float ag[20],eg[20],tg[20];
extern float alze,elze;
extern float fixdwell;
extern int fixflag;
float fixchk,agz,egz,tgz;
float xnz;
int i,j;
/* start fixation 200 millisecs within 1/2 deg */
static float fixstart=200.;
static float fixang=0.5*3.14159/180.; /* 1/2 degree */
static float chkang=1.0*3.14159/180.; /* 1 degree */
/* end fixation 50 millisecs outside 1 deg    */
static float fixend=50.;
static int nf=20;

/* update array */
for (i = 0;i < nf-1;i++) {
ag[i]=ag[i+1];
eg[i]=eg[i+1];
tg[i]=tg[i+1]; }
ag[nf-1]=alze;
eg[nf-1]=elze;
tg[nf-1]=dtime;

if(fixflag == 0)goto start;
if(fixflag == 1)goto contin;
return;

start: /* check for start of fixation */
agz=0.; egz=0.; tgz=0.;
for ( i = 0; i < nf; i++ ) {
agz=agz+ag[nf-1-i];
```

```
egz=egz+eg[nf-1-i];
tgz=tgz+tg[nf-1-i];
if(tgz > fixstart)goto label10; }
label10:
xnz=i+1; if(xnz < 1.0)xnz=1.0; agz=agz/xnz; egz=egz/xnz;
for ( j = 0; j <= i; j++ ) {
if(fabs(ag[nf-1-j] - agz) > fixang ||
   fabs(eg[nf-i-j] - egz) > fixang)return; }
/* start of fixation */
fixflag=1; fixchk=0.;
fixdwell=tgz;
return;

contin: /* check for continuation of fixation */
fixdwell=fixdwell+dtime;
if(fabs(ag[nf-1] - agz) > chkang ||
   fabs(eg[nf-1] - egz) > chkang)goto label20;
fixchk=0.;
return;

label20:
/* gaze point out of check & fixation check */
fixchk=fixchk+dtime;
if(fixchk < fixend)return;

label30:
/* end fixation */
fixflag=0;
fixdwell=0.0;

} collect_gaze(ie)

int ie; /* ----- eye flag ----- */
{/* collect working files results into dual eye reference files    */
extern float xvoz[2],yvoz[2],zvoz[2]; /* workspace viewing point    */
extern float avoz[2],bvoz[2],cvoz[2]; /* viewing axis direct cos    */
extern float alzez[2],elzez[2]; /* viewing azimuth and elevation    */
extern int idzz[2];              /* workspace viewed surface        */
```

```
extern float ixdzz[2],iydzz[2]   /* viewed surface point         */
              ,rszz[2];          /* eye distance to point        */
extern float xvo,yvo,zvo;        /* viewing point                */
extern float avo,bvo,cvo;  /* viewing axis directional cosines   */
extern float alze,elze;    /* workspace viewing orientation      */
extern int idz;            /* workspace panel in view            */
extern float ixdz,iydz,rsz; /* viewing point and distance        */
extern int nfix;           /* fixation history file              */
extern float afxz[2][10],efxz[2][10]; /* azimuth & elev angles   */
extern float vafz[2][10],vefz[2][10]; /* az & elev radial velocities */
extern float velz[2][10];        /* radial velocity history file */
extern char eyestatez[2]         /* fixation state flag          */
            ,classifyz[2]        /* classification flag .        */
            ,recordz[2];         /* prior classification         */
extern int startz[2]             /* fixation state start counter */
            ,endz[2]             /* saccadic end prediction      */
            ,blinkz[2];          /* blink duration               */
extern float afx[10],efx[10];    /* azimuth & elevation angles   */
extern float vaf[10],vef[10];    /* az & elev radial velocities  */
extern float vel[10];            /* radial velocity history      */
extern char eyestate,classify,record; /* fixation state    flags */
extern int start,end,blink;      /* fixation start & end counters */
extern int fixflagz[2];          /* gaze fixation state          */
extern float fixdwellz[2];       /* fixation dwell time          */
extern float agz[2][20],egz[2][20] /* gaze az & elev history     */
            ,tgz[2][20];         /* gaze time history            */
extern int fixflag;              /* gaze state flag              */
extern float fixdwell;           /* gaze fixation duration       */
extern float ag[20],eg[20],tg[20]; /* gaze history               */
int i;

/* viewing position and direction: */
xvoz[ie]=xvo; yvoz[ie]=yvo; zvoz[ie]=zvo;
avoz[ie]=avo; bvoz[ie]=bvo; cvoz[ie]=cvo;
alzez[ie]=alze; elzez[ie]=elze;

/* viewed point:        */
idzz[ie]=idz; ixdzz[ie]=ixdz; iydzz[ie]=iydz; rszz[ie]=rsz;

/* viewing state:       */
eyestatez[ie]=eyestate; classifyz[ie]=classify; recordz[ie]=record;
startz[ie]=start; endz[ie]=end; blinkz[ie]=blink;
```

```
for ( i = 0; i < nfix; i++ ) {
afxz[ie][i]=afx[i]; efxz[ie][i]=efx[i];
vafz[ie][i]=vaf[i]; vefz[ie][i]=vef[i];
velz[ie][i]=vel[i];              }
/* gaze state:             */
 fixflagz[ie]=fixflag; fixdwellz[ie]=fixdwell;
for ( i = 0; i < nfix; i++ ) {
agz[ie][i]=ag[i]; egz[ie][i]=eg[i];
tgz[ie][i]=tg[i];           }

} converge()

{/* convergence point line segment
    orthogonal to both lines of sight */
extern float xvoz[2],yvoz[2],zvoz[2]; /* workspace viewing point  */
extern float avoz[2],bvoz[2],cvoz[2]; /* viewing axis direct cos   */
extern float xicz[2],yicz[2],zicz[2]; /* convergence point         */
float rr[2],a,b,c,d;
int i;

/* equation constants */
a=avoz[0]*(xvoz[0]-xvoz[1])
  +bvoz[0]*(yvoz[0]-yvoz[1])
  +cvoz[0]*(zvoz[0]-zvoz[1]);
b=avoz[1]*(xvoz[0]-xvoz[1])
  +bvoz[1]*(yvoz[0]-yvoz[1])
  +cvoz[1]*(zvoz[0]-zvoz[1]);
c=avoz[0]*avoz[1]+bvoz[0]*bvoz[1]+cvoz[0]*cvoz[1];
d=1.0-c*c;

/* distance from viewing eye to convergence point */
rr[0]=(b*c-a)/d;
rr[1]=(b-a*c)/d;

/* convergence point each eye */
for ( i = 0; i < 1; i++)  {
xicz[i]=xvoz[i]+avoz[i]*rr[i];
yicz[i]=yvoz[i]+bvoz[i]*rr[i];
```

```
zicz[i]=zvoz[i]+cvoz[i]*rr[i]; }

} output_gaze()

{/* output gaze parameters to host computer */
extern float dtime;            /* ms time between samples    */
extern float xicz[2],yicz[2],zicz[2];  /* convergence point       */
extern float xvoz[2],yvoz[2],zvoz[2]; /* workspace viewing pnt   */ extern float alzez[2],elzez[2]; /* viewing azimuth and elevation */
extern float alzt,elzt;        /* head orientation           */
extern int idzz[2];            /* workspace viewed surface   */ extern float ixdzz[2],iydzz[2] /* viewed surface point       */
         ,rszz[2];             /* eye distance to point      */
extern char eyestate,classify; /* fixation state flags       */
extern int fixflagz[2];        /* gaze fixation state        */

/* particular to host computer data transfer communications */
output();

}
```

APPENDIX B: Calibration computer program used to calibrate the invention for the user.

APPENDIX B

```
/***********************************************

Calibration Routine for Viewing Point and Orientation
    Constants needed for Gaze Point Computations

*********************************************** */ calibrate()

{
/* calibration from display targets */
extern int ntgts;              /* display target number            */
extern float xtgt[10],ytgt[10],ztgt[10]; /* location display coords */
extern float xco,yco,zco;      /* corneal center coordinates       */
extern float rco;              /* corneal radius                   */
extern float aco,bco,cco;      /* optical axis directional cosines */
extern float acy,bcy,ccy;      /* horizontal axis directional cosines */
extern float acz,bcz,ccz;      /* vertical axis directional cosines */
extern float rview[3];         /* distance view point to corneal ctn */
extern float azv,elv;          /* view axis azimuth & elev angles  */
float xntgts;
float ar[10][10],br[10],zr[10];
float az,azo,el,elo,dx,dxo,dy,dyo,dz,dzo,dp,dpo;
float a1,b1,c1,a2,b2,c2,a3,b3,c3,rs,av,bv,cv,at,bt,ct,bq,cq;
int i;
FILE *fopen(), *in;
static float index=1.337; /* normial index of refraction */

/* first calibration target */
draw_target(0);    /* draw display target   */
hold_response();   /* hold for target fixation */
get_gaze();        /* get gaze for target   */
br[0]=xtgt[0]-xco; ar[0][0]=aco; ar[1][0]=acy; ar[2][0]=acz;
br[1]=ytgt[0]-yco; ar[0][1]=bco; ar[1][1]=bcy; ar[2][1]=bcz;
br[2]=ztgt[0]-zco; ar[0][2]=cco; ar[1][2]=ccy; ar[2][2]=ccz;
get_soln(3,ar,br,zr);
a1=zr[0]; b1=zr[1]; c1=zr[2];

/* second calibration target */
 draw_target(1);   /* draw display target   */
```

```
hold_response();    /* hold for target fixation */
get_gaze();         /* get gaze for target      */
br[0]=xtgt[1]-xco; ar[0][0]=aco; ar[1][0]=acy; ar[2][0]=acz;
br[1]=ytgt[1]-yco; ar[0][1]=bco; ar[1][1]=bcy; ar[2][1]=bcz;
br[2]=ztgt[1]-zco; ar[0][2]=cco; ar[1][2]=ccy; ar[2][2]=ccz;
get_soln(3,ar,br,zr);
a2=zr[0]; b2=zr[1]; c2=zr[2];

azo=0.; elo=0.; dxo=0.; dyo=0.; dzo=0.; dpo=0.;
/* remaining calibration targets */
for ( i = 2; i < ntgts; i++ ) {
draw_target(i);    /* draw display target      */
hold_response();   /* hold for target fixation */
get_gaze();        /* get gaze for target      */
get_pupil_ctn(&dp);
br[0]=xtgt[i]-xco; ar[0][0]=aco; ar[1][0]=acy; ar[2][0]=acz;
br[1]=ytgt[i]-yco; ar[0][1]=bco; ar[1][1]=bcy; ar[2][1]=bcz;
br[2]=ztgt[i]-zco; ar[0][2]=cco; ar[1][2]=ccy; ar[2][2]=ccz;
get_soln(3,ar,br,zr);
a3=zr[0]; b3=zr[1]; c3=zr[2];
az=atan2(b1-b2,a1-a2);
el=atan2(b1-b2,(c1-c2)*sin(az));
av=sin(el)*sin(az);
bv=sin(el)*cos(az);
cv=cos(el);
at=a1+a2+a3;
bt=b1+b2+b3;
ct=c1+c2+c3;
bq=av*at+bv*bt+cv*ct;
cq=at*at+bt*bt+ct*ct-9.0*(rco*rco);
cq=sqrt(bq*bq-cq);
rs=bq-cq;
dx=(at-av*rs)/3.0;
dy=(bt-bv*rs)/3.0;
dz=(ct-cv*rs)/3.0;
azo=azo+az; elo=elo+el;
dxo=dxo+dx; dyo=dyo+dy;
dzo=dzo+dz; dpo=dpo+dp;
a1=a2; b1=b2; c1=c2;
a2=a3; b2=b3; c2=c3;  }
xntgts=ntgts-2;
azv=azo/xntgts;
elv=elo/xntgts;
rview[0]=dxo/xntgts;
```

```
rview[1]=dyo/xntgts;
rview[2]=dzo/xntgts;
rcp=dpo/xntgts; }

/* save calibration constants */
in=fopen("eycal.dat","w");
if(in != NULL) {
fprintf(in,"%f\n %f\n %f\n %f\n %f\n %f\n %f\n",
index,rcp,azv,elv,rview[0],rview[1],rview[2]);
fclose(in); }
else
printf("cannot open file eycal.dat\n");

} draw_target(i)

int i;
{/* display driver for target cue */

} hold_response()

{/* hold for locating target and gazing */

} get_gaze()

{/* compute corneal center and corneal optical and roll axes
    for display target                                       */ corneal_ctn(); /* corneal ctr from emitter to sensor pairing table */
``` cluster_pts(); /* cluster corneal reflection pnts to smooth radii */ calib_optical_axes(); /* optical axis from corneal and pupil ctrs */

} get_pupil_ctn(dp)

float *dp;
{/* compute pupil center from emitter pairing table and image processing
                    */
extern long int image,i_ctn,j_ctn; /* pupil image center       */
extern long int ndata; /* pairings accumulated in display update */
extern long int i_row[100],i_col[100];/* sensor array coordinates */
extern float as[100],bs[100],cs[100]; /* sensor direction cosines */
extern float ar[100],br[100],cr[100]; /* corneal direction cosines */
extern float aco,bco,cco;      /* optical axis directional cosines */
extern float rc[100];          /* corneal radius              */
extern float index;            /* corneal index of refraction */
int i,ic;
float rchkx, rchkz;
float rcos,angr,tsin,angt,ocos,ango;
/* upper bound for reflection point to pupil image ctn */
static float check = 20.0;
static float pi = 3.14159;

if(image == 0)return; /* check for image processing success   */
/* pupil image isolated from ccd return & ctn computed        */

/* find sensor element closest to pupil ctn in pairing table  */
rchkz=10000.; ic=0;
for (i = 0; i < ndata; i++ ) {
rchkx=sqrt((i_ctn-i_row[i])*(i_ctn-i_row[i])
       + (j_ctn-i_col[i])*(j_ctn-i_col[i]));
if(rchkx < rchkz) {
rchkz=rchkx; ic=i; }       }
/* ensure sensor within range of pupil image center */
if(rchkz > check) return;

/* compute pupil center from reflection point coordinates & surface normal
                    */

```
/* ..... angle of refraction :                                    */
rcos=ar[ic]*as[ic]+br[ic]*bs[ic]+cr[ic]*cs[ic];
angr=acos(rcos);          /* angle of reflection          */
tsin=sin(angr)/index;     /* refraction from Snell's law  */
angt=asin(tsin);

/* ..... refraction internal angles :                             */
ocos=aco*ar[ic]+bco*br[ic]+cco*cr[ic];
ango=acos(ocos);

/* pupil center to corneal center distance                        */
*dp=rc[ic]*sin(angt)/sin(pi-angt-ango);

} calib_optical_axes()

{/* compute optical axes from smoothed corneal radii */
extern int kc;              /* number of reflection point clusters */
extern float arv[30],brv[30],crv[30]; /* central direction cosines */      extern float
xrv[30],yrv[30],zrv[30]; /* cluster central reflect pnt */
extern float rav[30];       /* smoothed corneal radius for cluster */
extern float rco;           /* optic center corneal radius         */
extern float xco,yco,zco;   /* corneal center coordinates          */
extern float aco,bco,cco;   /* optical axis directional cosines    */
extern float acy,bcy,ccy;   /* horizontal axis directional cosines */
extern float acz,bcz,ccz;   /* vertical axis directional cosines   */
float xm,ym,zm,am,bm,cm,rm,dm,rk,dk,rz,acz,bcz,ccz,test,rcmin;
int i,ic,ik,im;
static float test_val = 0.8660; /* cosine 30-degrees */
static float test_val2= 0.9659; /* cosine 15-degrees */
static float tol = 0.01;        /* tolerance in radii difference */

/* find minimum radius point */
rcmin=10000.; ic=0;
for ( i = 0; i < kc; i++ ) {
if(rcmin > rav[i] ) {
ic=i; rcmin=rav[i];         } }

/* find minimum radius point 30-degrees separation */
rcmin=10000.; ik=0;
```

```
for ( i = 0; i < kc; i++ ) {
if(i != ic) {
if(rcmin > rav[i]) {
test=arv[ic]*arv[i]+brv[ic]*brv[i]+crv[ic]*crv[i];
if(test < test_val) {
 ik=i; rcmin=rav[i]; } } } }

/* find vertical axis */
rz=sqrt((xrv[ic]-xrv[ik])*(xrv[ic]-xrv[ik])
       +(yrv[ic]-yrv[ik])*(yrv[ic]-yrv[ik])
       +(zrv[ic]-zrv[ik])*(zrv[ic]-zrvik]));
acz=(xrv[ic]-xrv[ik])/rz;
bcz=(yrv[ic]-yrv[ik])/rz;
ccz=(zrv[ic]-zrv[ik])/rz;

/* find optic center point */
xm=xrv[ik]+rz*acz/2.;
ym=yrv[ik]+rz*bcz/2.;
zm=zrv[ik]+rz*ccz/2.;
rm=sqrt((xm-xco)*(xm-xco)
       +(ym-yco)*(ym-yco)
       +(zm-zco)*(zm-zco));
am=(xm-xco)/rm;
bm=(ym-yco)/rm;
cm=(zm-zco)/rm;
dm=10000.; im=0;
for ( i = 0; i < kc; i++ ) {
rk=(xrv[i]-xco)*am+(yrv[i]-yco)*bm+(zrv[i]-zco)*cm;
dk=sqrt((xrv[i]-xco-rk*am)*(xrv[i]-xco-rk*am)
       +(yrv[i]-yco-rk*bm)*(yrv[i]-yco-rk*bm)
       +(zrv[i]-zco-rk*cm)*(zrv[i]-zco-rk*cm));
if(dm > dk) { dm=dk; im=i; } }
rco=rav[im];

if(zrv[ic] < zco)        /* check orientation          */
{ acz= -acz; bcz= -bcz; ccz= -ccz; }

/* compute optical axis */
rz=sqrt((xrv[im]-xco)*(xrv[im]-xco)
       +(yrv[im]-yco)*(yrv[im]-yco)
       +(zrv[im]-zco)*(zrv[im]-zco));
axo= (xrv[im]-xco)/rz;
bxo= (yrv[im]-yco)/rz;
cxo= (zrv[im]-zco)/rz;
```

```
/* horizontal axis */
/* find radius point 15-degrees separation from center */
ic=0;
for ( i = 0; i < kc; i++ ) {
if(sqrt((rco-rav[i])*(rco-rav[i])) < tol) {
test=aco*arv[i]+bco*brv[i]+cco*crv[i];
if(test < test_val2) {ic=i; } } }

/* find radius point 30-degrees separation */
ik=0;
for ( i = 0; i < kc; i++ ) {
if(i != ic) {
if(sqrt((rco-rav[i])*(rco-rav[i])) < tol) {
test=arv[ic]*arv[i]+brv[ic]*brv[i]+crv[ic]*crv[i];
 if(test < test_val) {
ik=i; } } } }

/* compute horizontal axis */
rz=sqrt((xrv[ic]-xrv[ik])*(xrv[ic]-xrv[ik])
       +(yrv[ic]-yrv[ik])*(yrv[ic]-yrv[ik])
       +(zrv[ic]-zrv[ik])*(zrv[ic]-zrvik]));
acy=(xrv[ic]-xrv[ik])/rz;
bcy=(yrv[ic]-yrv[ik])/rz;
ccy=(zrv[ic]-zrv[ik])/rz;
if(yrv[ic] < yco)        /* check orientation         */
{ acy= -acy; bcy= -bcy; ccy= -ccy; }

}
```

What is claimed is:

1. An apparatus for measuring the ocular gaze points of regard and fixation durations and binocular convergence point of a viewer, comprising:

a) a headset;
 b) a position and orientation sensor having an electrical output, wherein said sensor is constructed so as to connect to said headset, said position and orientation sensor comprising means to determine position and orientation of said headset on head of said viewer;
 c) an optical unit constructed so as to provide a clocked raster-scan pulse electrical output and further constructed so as to provide a clocked display field refresh pulse electrical output having an optical output, said optical unit is constructed so as to connect to said headset so as to display a visual image onto eyes of said viewer, and further constructed so as to optically output cornea and pupil reflections of the viewer's eyes;
 d) an opto-electronic device constructed so as to receive an optical input, said optical input connected to said optical output of said optical unit, said opto-electronic device further constructed so as to receive a clocked raster scan pulse electrical input from said optical unit, said opto-electronic device further constructed so as to provide an analog electrical output, said opto-electronic device further constructed so as to provide a digital electrical output for transmitting an electrical signal said opto-electronic device further comprising means for electronically representing spatially optical corneal reflection transmitted from said optical unit;
 e) a digital processor constructed so as to receive a clocked raster-scan pulse electrical input from said optical unit, said digital processor further constructed so as to receive an electrical digital input, said electrical digital input connected to the digital output from said opto-electronic device, said processor further constructed to read an output from said opto-electronic device on each clock-pulse and further constructed to write said output from said opto-electronic device to a double-buffered digital memory;
 f) an image processor constructed so as to receive an electrical analog input, said electrical analog input connected to said analog output of said opto-electronic device, said image processor further constructed so as to receive a clocked display field refresh pulse input from said optical unit, said image processor further constructed so as to provide a memory mapped digital output of pupil image coordinates and principal axes following each of a clocked field refresh pulse;
 g) a digital computer, constructed so as to receive an input connected to the output of said position and orientation sensor, said digital computer comprising means to access an output of said double-buffered digital memory of said digital processor, said digital computer constructed so as to access the memory mapped output of said image processor, said digital computer further constructed so as to receive a clocked display field refresh pulse input, said digital computer further constructed so as to provide a digital output for each of calibration, computed gaze points of regard and fixation durations, and binocular convergence point of the viewer, following said each clocked field refresh pulse, during application.

2. The apparatus as recited in claim 1, wherein said headset further comprises:

a) head and hat bands each having contact pads, said contact pads constructed to be positioned on load bearing portions of the viewer's face and head, said load bearing portions comprising at least one of cheek bones, temporal regions, top of the head, back of the head, and inion budge at rear of skull;
 b) said hat bands further comprising an additional contact pad constructed so as to force the hat bands to stand off of the viewer's forehead, said pad further constructed so as to prevent eyebrow movement from disturbing said headset;
 c) a nose bridge in front and pivot joints at the sides of the said hat bands, said nose bridge further constructed so as to support said optical unit.

3. The apparatus as recited in claim 1, wherein said optical unit further comprises:

a) a video display unit, constructed so as to provide a clocked raster scan pulse electrical output and a clocked display field refresh pulse electrical output;
 b) a dielectric polarizer disposed in path of light emanating from said video display, said polarizer constructed so as to polarize light emanating from said video display;
 c) an optical system said optical system constructed so as to direct and focus light emanating from said video display onto eyes of the viewer;
 d) a quarter-waveplate, positioned in path of polarized light reaching the eyes of the viewer from said optical system and further positioned in path of light reflected back from the eyes, said quarter-waveplate further constructed so as to rotate polarized light one-half wavelength;
 e) a semi-reflective mirror positioned in path of polarized light reflected back from the eyes of the viewer through said waveplate, said mirror constructed so as to reflect polarized light in a direction away from the eyes of the viewer;
 f) an optical lens system, having an optical output, positioned in path of light reflecting from the eyes of the viewer after light reflecting from the eyes has passed through said waveplate and reflected from the said semi-reflective mirror, said lens system constructed so as to optically filter and focus corneal and pupil reflections of the eyes of the viewer in response to illumination caused by said video display.

4. The apparatus as recited in claim 2, wherein said video display further comprises:

a) an array of light emitting elements wherein said elements are selected from the group consisting of active emitter, passive emitter including active matrix, light emitting diode, or a combination thereof;
 b) an electronic display driver wherein said driver is constructed so as to excite said display elements sequentially in accordance with a specific display refresh order, such that an initial flare of illumination common to all said emitter elements occurs as each display element is refreshed said display driver is further constructed such that display element refresh signal from said display driver is synchronized with said clocked raster-scan pulse electrical output from said video display, to said opto-electronic device and said digital processor;

said display driver is further constructed so as to synchronize with said clocked display field refresh pulse electrical output from said video display to said digital processor and said digital computer.

5. The apparatus as recited in claim 1, wherein said opto-electronic device further comprises:

a) a two-dimensional array of electronic opto-transistors said transistors further constructed so as to receive optical input from said optical lens system; said transistors further constructed so as to provide electrical analog outputs;

b) an array of electronic comparators, said comparators constructed so as to match electrical analog input one-to-one to output of said array of opto-transistors and electrical digital output wherein output of each said comparators is constructed to be set when output of corresponding said opto-transistor exceeds a threshold level and further constructed to be reset when said opto-transistor remains below said threshold level, wherein the threshold level is less than electrical voltage generated by initial refresh illumination from a display element of said video display, but greater than the voltage generated by extraneous visual reflections and electronic noise;

c) an electronic encoder constructed so as to receive electrical digital inputs from said comparators and electrical digital output giving the array address of the said set comparator; and d) an electronic latch which latches and holds the digital address output of the said encoder as output until reset by the clocked raster-scan pulse electrical output from said display driver of claim 4, where the reset is momentarily delayed to allow operation of the digital processor of claim 1 as described below.

6. The apparatus as recited in claim 1, wherein said digital processor further comprises:

a) means for reading latched address output of the opto-electronic device on said each clocked raster-scan pulse electrical output from said display driver, and means for writing address to a doubled-buffered digital memory, said means for writing further constructed so as to form a digital data table of comparator addresses as a function of clocked pulse count;

b) said digital data table further constructed so as to serve as a reference list of said sensor activated by excited light element, for said each clocked raster-scan pulse count, so as to serve as a source-to-sensor pairing table for the clocked display field refresh cycle; and c) wherein, memory of said digital processor is buffered by the clocked display field refresh pulse output from said display driver and the clocked raster-scan pulse count is reset to zero.

7. The apparatus as recited in claim 1, wherein said image processor further comprises:

a) a charge coupled device array having electrical analog input from the analog output of the opto-transistor array such that electronic digitization of eye image is enabled over the clocked display field refresh cycle of said display driver;

b) means for isolating the viewer's pupil image by binarization and thresholding of the accumulated digital eye image, said means further constructed so as to enable an action executed at receipt of the clocked display field refresh pulse output from said display driver; and c) means for computing binary image centroid, principal axes and memory mapped electrical digital output of the image processor.

8. A method for computing, by digital computer using a digital computer program, the gaze point of regard and fixation duration for each eye, and the binocular convergence point for both eyes of a viewer, said method comprising the steps of:

(a) responding through an interrupt service routine operating in response to a clocked display field refresh pulse output from a display driver;

(b) reading the position and orientation of headset sensor;

(c) computing corneal center of said each eye from a three dimensional model of corneal reflections, and further computing cornea surface point locations of the reflections from a source-to-sensor pairing table and embedded memory tables of geometries for a light array and a sensor array;

(d) smoothing the computed corneal reflections for said each eye by clustering together surface points with similar orientation relative to the respective corneal center;

(e) computing pupil center for said each eye from the respective said corneal center of said each eye, further computing memory mapped pupil image center and source to sensor pairing table;

(f) computing optical origin and axis for said each eye from the corresponding corneal and pupil centers;

(g) computing median axes for cornea of said each eye from a corresponding said optical axis and from data obtained on said smoothed corneal reflection;

(h) computing viewing origin and axis for said each eye from the corresponding said optical origin and axis and median axes;

(i) converting viewing origin and axis for said each eye to the viewer's workspace from a headset position and orientation sensor reading;

(j) classifying viewing status of said each eye as saccadic, fixation, or pursuit from data obtained in steps (a) through (i);

(k) classifying gaze status of said each eye by grouping local fixations, and computing the gaze point of regard in the viewer's workspace and fixation duration, from the respective viewing origin and axis, and an embedded memory table of workspace geometry; and (l) computing the binocular convergence point from the viewing origins and axes of both of said eyes for the viewer's workspace.

9. A method as recited in claim 8, said method further comprising:

(a) determining certain optical constants for developing said routines, sequentially displaying a calibration marker at a set of predetermined locations within a visual field of a viewer, and directing the viewer's gaze at said marker locations;

(b) obtaining a digital output for step a;

(c) displaying said calibration marker within said field of the viewer using a video display;

(d) sending a digital instruction to said display driver and displaying said calibration marker at a predetermined location within said visual field of the viewer, said sending step further comprises using a computer program with a display prompting routine;

(e) fixating said viewer's gaze on a target;

(f) establishing an interrupt service routine in response to a clocked display field refresh pulse output from the display driver;

(g) establishing a routine for reading position and orientation of a headset sensor when said calibration display is not attached to the headset;

(h) establishing a routine using said three dimensional model of corneal reflections for computing the cornea center of said eye and surface locations of the corneal reflections, from a source-to-sensor pairing table and embedded memory tables of geometries for light array and a sensor array;

(i) establishing a routine for smoothing the computed corneal reflections for each eye by clustering together surface points with nearly the same orientation relative to the corresponding corneal center;

(j) establishing a routine for computing the optical origin and axis, and the median axes for cornea of each eye from said corneal center and smoothed corneal reflection data;

(k) computing a routine once three such calibration markers have been presented at separate locations, said routine computes using the marker location and headset position and orientation, a set of constant parameters for each eye relating the viewing origin and orientation to the optical origin and the optical and median axes;

(l) establishing a routine for computing, once three such calibration markers have been presented at separate locations, using pupil image centroid, interocular corneal center to pupil center distance, a constant parameter for each eye; and (m) establishing a routine called by said display prompting routine following the display of the calibration marker at all locations, said routine computing best estimate to said optical constants and saving values of said constants in a memory file for reference.

10. A method for determining optical constants for developing routines for the gaze point of regard and fixation duration for each eye, and the binocular convergence point for both eyes of a viewer, said method further comprising:

(a) sequentially displaying a calibration marker at a set of predetermined locations within a visual field of a viewer, and directing the viewer's gaze at said marker locations;

(b) obtaining a digital output for step a;

(c) displaying said calibration marker within said field of the viewer using a video display;

(d) sending a digital instruction to said display driver and displaying said calibration marker at a predetermined location within said visual field of the viewer, said sending step further comprises using a computer program with a display prompting routine;

(e) fixating said viewer's gaze on a target and releasing said target from hibernation;

(f) establishing an interrupt service routine in response to a clocked display field refresh pulse output from the display driver;

(g) establishing a routine for reading position and orientation of a headset sensor when said calibration display is not attached to the headset;

(h) establishing a routine using said three dimensional model of corneal reflections, from a source-to-sensor pairing table and embedded memory tables of geometries for light array and a sensor array;

(i) establishing a routine for smoothing the computed corneal reflections for each eye by clustering together surface points with nearly the same orientation relative to the corresponding corneal center;

(j) establishing a routine for computing the optical origin and axis, and the median axes for cornea of each eye from said corneal center and smoothed corneal reflection data;

(k) computing a routine once three such calibration markers have been presented at separate locations, said routine computes using the marker location headset position and orientation, a set of constant parameters for each eye relating the viewing origin and orientation to the optical origin and the optical and median axes;

(l) establishing a routine for computing, once three such calibration markers have been presented at separate locations, using pupil image centroid, interocular corneal center to pupil center distance, a constant parameter for each eye; and (m) establishing a routine called by said display prompting routine following the display of the calibration marker at all locations, said routine computing best estimate to said optical constants and saving values of said constants in a memory file for reference.

* * * * *